US006410586B1

(12) United States Patent
Møller et al.

(10) Patent No.: US 6,410,586 B1
(45) Date of Patent: Jun. 25, 2002

(54) MODULATORS OF PROTEIN TYROSINE PHOSPHATASES (PTPASES)

(75) Inventors: Niels Peter Hundahl Møller, Copenhagen; Henrik Sune Andersen, Lyngby; Lars Fogh Iversen, Holte; Ole Hvilsted Olsen, Brønshøj; Sven Branner, Lyngby, all of (DK); Daniel Dale Holsworth; Farid Bakir, both of San Diego, CA (US); Luke Milburn Judge, La Jolla, CA (US); Frank Urban Axe, Escondido, CA (US); Todd Kevin Jones, Solana Beach, CA (US); William Charles Ripka, San Diego, CA (US); Yu Ge, San Diego, CA (US); Roy Teruyuki Uyeda, San Diego, CA (US)

(73) Assignees: Novo Nordisk A/S, Bagsvaerd (DK); Ontogen Corporation, Carlsbad, CA (US)

(*) Notice: Subject to any disclaimer, the term of this patent is extended or adjusted under 35 U.S.C. 154(b) by 0 days.

(21) Appl. No.: 09/810,266

(22) Filed: Mar. 16, 2001

Related U.S. Application Data

(62) Division of application No. 09/268,490, filed on Mar. 11, 1999.
(60) Provisional application No. 60/082,915, filed on Apr. 24, 1998, provisional application No. 60/093,525, filed on Jul. 21, 1998, and provisional application No. 60/108,747, filed on Nov. 17, 1998.

(30) Foreign Application Priority Data

Mar. 12, 1998 (DK) ............................................. 0344/98
Apr. 3, 1998 (DK) ......................................... 1998 00480
Jul. 15, 1998 (DK) ......................................... 1998 00938
Oct. 28, 1998 (DK) ......................................... 1998 01385
Dec. 7, 1998 (DK) ......................................... 1998 01612

(51) Int. Cl.⁷ ..................... A61K 31/381; A61K 31/35; C07D 409/04
(52) U.S. Cl. ........................ 514/443; 549/396; 549/49; 549/50; 514/438; 514/453; 514/456
(58) Field of Search ........................... 548/250, 452, 548/454; 549/49, 396, 50; 514/438, 443, 453, 456

(56) References Cited

U.S. PATENT DOCUMENTS

| 3,627,766 A | 12/1971 | Eichenberger et al. ...... 544/250 |
| 4,016,276 A | 4/1977 | Kobayakawa et al. ...... 424/256 |
| 4,550,106 A | 10/1985 | Schneider et al. .......... 514/212 |
| 4,920,043 A | 4/1990 | Ohashi et al. .............. 430/611 |
| 5,049,559 A | 9/1991 | Braquet et al. ............. 514/219 |
| 5,049,560 A | 9/1991 | Esanu et al. ................ 514/219 |
| 5,189,054 A | 2/1993 | Salituro et al. ............. 514/419 |
| 5,221,671 A | 6/1993 | Kazuo et al. ............... 514/219 |
| 6,225,329 B1 * | 5/2001 | Richter et al. .............. 514/359 |

FOREIGN PATENT DOCUMENTS

| DE | 25 09 457 | 9/1975 |
| DE | 3112164 A1 | 10/1982 |
| DE | 3328438 A1 | 2/1984 |
| EP | 0 348 872 | 1/1990 |
| WO | WO 91/16325 | 10/1991 |

OTHER PUBLICATIONS

Chemical Abstracts, vol. 116, No. 9, Mar. 2, 1992, The Abstract No. 83486a, Bioorg. Med., Chem Lett. 1991 (9), 455–460.

* cited by examiner

*Primary Examiner*—Alan L. Rotman
*Assistant Examiner*—Rita Desai
(74) *Attorney, Agent, or Firm*—Reza Green, Esq.; Peter J. Waibel, Esq.

(57) ABSTRACT

The present invention provides novel compounds, novel compositions, methods of their use, and methods of their manufacture, where such compounds are pharmacologically useful inhibitors of Protein Tyrosine Phosphatases (PTPase's) such as PTP1B, CD45, SHP-1, SHP-2, PTPα, LAR and HePTP or the like. The compounds are useful in the treatment of type I diabetes, type II diabetes, impaired glucose tolerance, insulin resistance, obesity, immune dysfunctions including autoimmunity diseases with dysfunctions of the coagulation system, allergic diseases including asthma, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimer's disease and schizophrenia, and infectious diseases.

7 Claims, No Drawings

MODULATORS OF PROTEIN TYROSINE PHOSPHATASES (PTPASES)

CROSS-REFERENCE TO RELATED APPLICATIONS

This application is a divisional of U.S. application Ser. No. 09/268,490 filed on Mar. 11, 1999, and claims priority under 35 U.S.C. 119 of U.S. provisional application Ser. Nos. 60/082,915, 60/093,525 and 60/108,747 filed Apr. 24, 1998, Jul. 21, 1998 and Nov. 17, 1998, respectively, and of Danish application nos. 0344/98, PA 1998 00480, PA 1998 00938, PA 1998 01385 and PA 1998 01612 filed Mar. 12, 1998, Apr. 3, 1998, Jul. 15, 1998, Oct. 28, 1998 and Dec. 7, 1998, the contents of which are fully incorporated herein by reference.

FIELD OF THE INVENTION

The present invention relates to novel compounds, to methods for their preparation, to compositions comprising the compounds, to the use of these compounds as medicaments and their use in therapy, where such compounds of Formula 1 are pharmacologically useful inhibitors of Protein Tyrosine Phosphatases (PTPases) such a PTP1B, CD45, SHP-1, SHP-2, PATα, LAR and HePTP or the like,

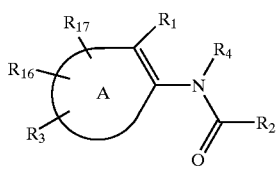

Formula 1 wherein A, $R_1$, $R_2$, $R_3$, $R_4$, $R_{16}$ and $R_{17}$ are defined more fully below.

It has been found that PTPases plays a major role in the intracellular modulation and regulation of fundamental cellular signaling mechanisms involved in metabolism, growth, proliferation and differentiation (Flint et al., The EMBO J. 12:1937–46 (1993); Fischer et al, Science 253:401–6 (1991)). Overexpression or altered activity of tyrosine phosphatases can also contribute to the symptoms and progression of various diseases (Wiener, et al., J. Natl. cancer Inst. 86:372–8 (1994); Hunter and Cooper, Ann. Rev. Biochem, 54:897–930 (1985)). Furthermore, there is increasing evidence which suggests that inhibition of these PTPases may help treat certain types of diseases such as diabetes type I and II , autoimmune disease, acute and chronic inflammation, osteoporosis and various forms of cancer.

BACKGROUND OF THE INVENTION

Protein phosphorylation is now well recognized as an important mechanism utilized by cells to transduce signals during different stages of cellular function (Fischer et al, Science 253:401–6 (1991); Flint et al., The EMBO J. 12:1937–46 (1993)). There are at least two major classes of phosphatases: (1) those that dephosphorylate proteins (or peptides) that contain a phosphate group(s) on a serine or threonine moiety (termed Ser/Thr phosphatases) and (2) those that remove a phosphate group(s) from the amino acid tyrosine (termed protein tyrosine phosphatases or PTPases).

The PTPases are a family of enzymes that can be classified into two groups: a) intracellular or nontransmembrane PTPases and b) receptor-type or transmembrane PTPases.

Intracellular PTPases: Most known intracellular type PTPases contain a single conserved catalytic phosphatase domain consisting of 220–240 amino acid residues. The regions outside the PTPase domains are believed to play important roles in localizing the intracellular PTPases subcellularly (Mauro, L. J. and Dixon, J. E. TIBS 19: 151–155 (1994)). The first intracellular PTPase to be purified and characterized was PTP1B which was isolated from human placenta (Tonks et al., J. Biol. Chem. 263: 6722–6730 (1988)). Shortly after, PTP1B was cloned (Charbonneau et al, Proc. Natl. Acad. Sci. USA 86: 5252–5256 (1989); Chernoff et al, Proc. Natl. Acad. Sci. USA 87: 2735–2789 (1989)). Other examples of intracellular PTPases include (1) T-cell PTPase (Cool et al. Proc. Natl. Acad. Sci. USA 86: 5257–5261 (1989)), (2) rat brain PTPase (Guan et al., Proc. Natl. Acad. Sci. USA 87:1501–1502 (1990)), (3) neuronal phosphatase STEP (Lombroso et al., Proc. Natl. Acad. Sci. USA 88: 7242–7246 (1991)), (4) ezrin-domain containing PTPases: PTPMEG1 (Guet al., Proc. Natl. Acad. Sci. USA 88: 5867–57871 (1991)), PTPH1 (Yang and Tonks, Proc. Natl. Acad. Sci. USA 88: 5949–30 5953 (1991)), PTPD1 and PTPD2 (Møller et al., Proc. Natl. Acad. Sci. USA 91: 7477–7481 (1994)), FAP-1/BAS (Sato et al., Science 268: 411–415 (1995); Banville et al., J. Biol. Chem. 269: 22320–22327 (1994); Maekawa et al., FEBS Letters 337: 200–206 (1994)), and SH2 domain containing PTPases: PTP1C/SH-PTP1/SHP-1 (Plutzky et al., Proc. Natl. Acad. Sci. USA 89:1123–1127 (1992); Shen et al., Nature Lond. 352: 736–739 (1991)) and PTP1 D/Syp/SH-PTP2/SHP-2 (Vogel et al, Science 259: 1611–1614 (1993); Feng et al., Science 259: 1607–1611 (1993); Bastein et al., Biochem. Biophys. Res. Comm. 196: 124–133 (1993)).

Low molecular weight phosphotyrosine-protein phosphatase (LMW-PTPase) shows very little sequence identity to the intracellular PTPases described above. However, this enzyme belongs to the PTPase family due to the following characteristics: (i) it possesses the PTPase active site motif: Cys-Xxx-Xxx-Xxx-Xxx-Xxx-Arg (Cirri et al., Eur. J. Biochem. 214: 647–657 (1993)); (ii) this Cys residue forms a phospho-intermediate during the catalytic reaction similar to the situation with 'classical' PTPases (Cirri et al, supra; Chiarugi et al., FEBS Left. 310: 9–12 (1992)); (iii) the overall folding of the molecule shows a surprising degree of similarity to that of PTP1B and Yersinia PTP (Su et al., Nature 370: 575–578 (1994)).

Receptor-type PTPases consist of a) a putative ligand-binding extracellular domain, b) a transmembrane segment, and c) an intracellular catalytic region. The structures and sizes of the putative ligand-binding extracellular domains of receptor-type PTPases are quite divergent. In contrast, the intracellular catalytic regions of receptor-type PTPases are very homologous to each other and to the intracellular PTPases. Most receptor-type PTPases have two tandemly duplicated catalytic PTPase domains.

The first receptor-type PTPases to be identified were (1) CD45/LCA (Ralph, S. J., EMBO J. 6: 1251–1257 (1987)) and (2) LAR (Streuli et al., J. Exp. Med. 168: 1523–1530 (1988)) that were recognized to belong to this class of enzymes based on homology to PTP1B (Charbonneau et al., Proc. Natl. Acad. Sci. USA 86: 5252–5256 (1989)). CD45 is a family of high molecular weight glycoproteins and is one of the most abundant leukocyte cell surface glycoproteins and appears to be exclusively expressed upon cells of the hematopoietic system (Trowbridge and Thomas, Ann. Rev. Immunol. 12: 85–116 (1994)).

The identification of CD45 and LAR as members of the PTPase family was quickly followed by identification and cloning of several different members of the receptor-type PTPase group. Thus, 5 different PTPases, (3) PTPα, (4)

PTPβ, (5) PTPδ, (6) PTPε, and (7) PTPζ, were identified in one early study (Krueger et al, *EMBO J.* 9: 3241–3252 (1990)). Other examples of receptor-type PTPases include (8) PTPγ (Barnea et al, *Mol. Cell. Biol.* 13:1497–1506 (1995)) which, like PTPζ (Krueger and Saito, *Proc. Natl. Acad. Sci. USA* 89: 7417–7421 (1992)) contains a carbonic anhydrase-like domain in the extracellular region, (9) PTPμ (Gebbink et at, *FEBS Letters* 290: 123–130 (1991)), (10) PTPKκ (Jiang et al., *Mol. Cell. Biol.* 13: 2942–2951 (1993)). Based on structural differences the receptor-type PTPases may be classified into subtypes (Fischer et al., *Science* 253: 401–406 (1991)): (I) CD45; (II) LAR, PTPd, (11) PATσ; (III) PTPb, (12) SAP-1 (Matozaki et al., *J. Biol. Chem.* 269: 2075–2081 (1994)), (13) PTP-U2/GLEPP1 (Seimiya et al., *Oncogene* 10: 1731–1738 (1995); Thomas et al., *J. Biol. Chem.* 269:19953–19962 (1994)), and (14) DEP-1; (IV) PTPa,_PTPe. All receptor-type PTPases except Type IV contain two PTPase domains. Novel PTPases are continuously identified, and it is anticipated that more than 500 different species will be found in the human genome, i.e. close to the predicted size of the protein tyrosine kinase superfamily (Hanks and Hunter, *FASEB J.* 9: 576–596 (1995)).

PTPases are the biological counterparts to protein tyrosine kinases (PTKs). Therefore, one important function of PTPases is to control, down-regulate, the activity of PTKs. However, a more complex picture of the function of PTPases now emerges. Several studies have shown that some PTPases may actually act as positive mediators of cellular signalling. As an example, the SH2 domain-containing PTP1D seems to act as a positive mediator in insulin-stimulated Ras activation (Noguchi et al., *Mol. Cell. Biol.* 14: 6674–6682 (1994)) and of growth factor-induced mitogenic signal transduction (Xiao et al., *J. Biol. Chem.* 269: 21244–21248 (1994)), whereas the homologous PTP1C seems to act as a negative regulator of growth factor-stimulated proliferation (Bignon and Siminovitch, *Clin.Immunol. Immunopathol.* 73:168–179 (1994)). Another example of PTPases as positive regulators has been provided by studies designed to define the activation of the Src-family of tyrosine kinases. In particular, several lines of evidence indicate that CD45 is positively regulating the activation of hematopoietic cells, possibly through dephosphorylation of the C-terminal tyrosine of Fyn and Lck (Chan et al., *Annu. Rev. Immunol.* 12: 555–592 (1994)).

Dual specificity protein tyrosine phosphatases (dsPTPases) define a subclass within the PTPases family that can hydrolyze phosphate from phosphortyrosine as well as from phosphor-serine/threonine. dsPTPases contain the signature sequence of PTPases: His-Cys-Xxx-Xxx-Gly-Xxx-Xxx-Arg. At least three dsPTPases have been shown to dephosphorylate and inactivate extracellular signal-regulated kinase (ERKs)/mitogen-activated protein kinase (MAP K): MAPK phosphatase (CL100, 3CH134) (Charles et al., *Proc. Natl. Acad. Sci. USA* 90: 5292–5296 (1993)); PAC-1 (Ward et al, *Nature* 367: 651–654 (1994)); rVH6 (Mourey et al., *J. Biol. Chem.* 271: 3795–3802 (1996)). Transcription of dsPTPases are induced by different stimuli, e.g. oxidative stress or heat shock (Ishibashi et al., *J. Biol. Chem.* 269: 29897–29902 (1994); Keyse and Emslie, *Nature* 359: 644–647 (1992)). Further, they may be involved in regulation of the cell cycle: cdc25 (Millar and Russell, *Cell* 68: 407–410 (1992)); KAP (Hannon et al., *Proc. Natl. Acad. Sci. USA* 91: 1731–1735 (1994)). Interestingly, tyrosine dephosphorylation of cdc2 by a dual specific phosphatase, cdc25, is required for induction of mitosis in yeast (review by Walton and Dixon, *Annu. Rev. Biochem.* 62:101–120 (1993)).

PTPases were originally identified and purified from cell and tissue lysates using a variety of artificial substrates and therefore their natural function of dephosphorylation was not well known. Since tyrosine phosphorylation by tyrosine kinases is usually associated with cell proliferation, cell transformation and cell differentiation, it was assumed that PTPases were also associated with these events. This association has now been proven to be the case with many PTPases. PTP1B, a phosphatase whose structure was recently elucidated (Barford et al., Science 263:1397–1404 (1994)) has been shown to be involved in insulin-induced oocyte maturation (Flint et al., The EMBO J. 12:193746 (1993)) and recently it has been suggested that the overexpression of this enzyme may be involved in p185$^{c\text{-}erb}$ $_{B2}$-associated breast and ovarian cancers (Wiener, et al., J. Natl. cancer Inst. 86:372–8 (1994); Weiner et al., Am. J. Obstet. Gynecol. 170:1177–883 (1994)). The insulin-induced oocyte maturation mechanism has been correlated with the ability of PTP1B to block activation of S6 kinase. The association with cancer is recent evidence which suggests that overexpression of PTP1B is statistically correlated with increased levels of p185$^{c\text{-}erb\ B2}$ in ovarian and breast cancer. The role of PTP1B in the etiology and progression of the disease has not yet been elucidated. Inhibitors of PTP1B may therefore help clarify the role of PTP1B in cancer and in some cases provide therapeutic treatment for certain forms of cancer.

The activity of a number of other newly discussed phosphatases are currently under investigation. Two of these: SHP-1 and Syp/PTP1D/SHPTP2/PTP2C/SHP-2 have recently been implicated in the activation of Platelet Derived Growth Factor and Epidermal Growth Factor induced responses (Li et al., Mole. Cell. Biol. 14:509–17 (1994)). Since both growth factors are involved in normal cell processing as well as disease states such as cancer and arteriosclerosis, it is hypothesized that inhibitors of these phosphatases would also show therapeutic efficacy. Accordingly, the compounds of the present invention which exhibit inhibitory activity against various PTPases, are indicated in the treatment or management of the foregoing diseases.

PTPases: The Insulin Receptor Signalling Pathway/Diabetes

Insulin is an important regulator of different metabolic processes and plays a key role in the control of blood glucose. Defects related to its synthesis or signalling lead to diabetes mellitus. Binding of insulin to its receptor causes rapid (auto)phosphorylation of several tyrosine residues in the intracellular part of the b-subunit. Three closely positioned tyrosine residues (the tyrosine-1150 domain) must all be phosphorylated to obtain full activity of the insulin receptor tyrosine kinase (IRTK) which transmits the signal further downstream by tyrosine phosphorylation of other cellular substrates, including insulin receptor substrate-1 (IRS-1) (Voilden et al., J. Biol. Chem. 267:16660–16668 (1992); Myers and White, Diabetes 42: 643–650 (1993); Lee and Pilch, Am. J. Physiol. 266: C319–C334 (1994); White et al., J. Biol. Chem. 263: 2969–2980 (1988)). The structural basis for the function of the tyrosine-triplet has been provided by recent X-ray crystallographic studies of IRTK that showed tyrosine-1150 to be autoinhibitory in its unphosphorylated state (Hubbard et al., Nature 372: 746–754 (1994)).

Several studies clearly indicate that the activity of the auto-phosphorylated IRTK can be reversed by dephosphorylation in vitro (reviewed in Goldstein, Receptor3: 1–15 (1993); Mooney and Anderson, J. Biol. Chem. 264: 6850–6857 (1989)), with the tri-phosphorylated tyrosine-1150 domain being the most sensitive target for protein-tyrosine phosphatases (PTPases) as compared to the di- and mono-phosphorylated forms (King et al., *Biochem. J.* 275: 413–418 (1991)). It is, therefore, tempting to speculate that this tyrosine-triplet functions as a control switch of IRTK activity. Indeed, the IRTK appears to be tightly regulated by PTP-mediated dephosphorylation in vivo (Khan et al., *J. Biol. Chem.* 264: 12931–12940 (1989); Faure et al.,*J. Biol. Chem.* 267: 11215–11221 (1992); Rothenberg et al., *J. Biol. Chem.* 266: 8302–8311 (1991)). The intimate coupling of PTPases to the insulin signalling pathway is further evidenced by the finding that insulin differentially regulates PTPase activity in rat hepatoma cells (Meyerovitch et al., *Biochemistry* 31: 10338–10344 (1992)) and in livers from alloxan diabetic rats (Boylan et al., *J. Clin. Invest.* 90: 174–179 (1992)).

Relatively little is known about the identity of the PTPases involved in IRTK regulation. However, the existence of PTPases with activity towards the insulin receptor can be demonstrated as indicated above. Further, when the strong PTPase-inhibitor pervanadate is added to whole cells an almost full insulin response can be obtained in adipocytes (Fantus et al., *Biochemistry* 28: 8864–8871 (1989); Eriksson et al., *Diabetologia* 39: 235–242 (1995)) and skelet al muscle (Leighton et al., *Biochem. J.* 276: 289–292 (1991)). In addition, recent studies show that a new class of peroxovanadium compounds act as potent hypoglycemic compounds in vivo (Posner et al.,supra). Two of these compounds were demonstrated to be more potent inhibitors of dephosphorylation of the insulin receptor than of the EGF-receptor.

It was recently found that the ubiquitously expressed SH2 domain containing PTPase, PTP1D (Vogel et al., 1993, supra), associates with and dephosphorylates IRS-1, but apparently not the IR itself (Kuhnéet al.,*J. Biol. Chem.* 268: 11479–11481 (1993); (Kuhne et al., *J. Biol. Chem.* 269: 15833–15837 (1994)).

Previous studies suggest that the PTPases responsible for IRTK regulation belong to the class of membrane-associated (Faure et al., *J. Biol. Chem.* 267: 11215–11221 (1992)) and glycosylated molecules (Häring et al., *Biochemistry* 23: 3298–3306 (1984); Sale, *Adv. Prot Phosphatases* 6: 159–186 (1991)). Hashimoto et al. have proposed that LAR might play a role in the physiological regulation of insulin receptors in intact cells (Hashimoto et al., *J. Biol. Chem.* 267: 13811–13814 (1992)). Their conclusion was reached by comparing the rate of dephosphorylation/inactivation of purified IR using recombinant PTP1B as well as the cytoplasmic domains of LAR and PTPa. Antisense inhibition was recently used to study the effect of LAR on insulin signalling in a rat hepatoma cell line (Kulas et al., *J. Biol. Chem.* 270: 2435–2438 (1995)). A suppression of LAR protein levels by about 60 percent was paralleled by an approximately 150 percent increase in insulin-induced autophosphorylation. However, only a modest 35 percent increase in IRTK activity was observed, whereas the insulin-dependent phosphatidylinositol 3-kinase (PI 3-kinase) activity was significantly increased by 350 percent. Reduced LAR levels did not alter the basal level of IRTK tyrosine phosphorylation or activity. The authors speculate that LAR could specifically dephosphorylate tyrosine residues that are critical for PI 3-kinase activation either on the insulin receptor itself or on a downstream substrate.

While previous reports indicate a role of PTPa in signal transduction through src activation (Zheng et al., *Nature* 359: 336–339 (1992); den Hertog et al., *EMBO J.* 12: 3789–3798 (1993)) and interaction with GRB-2 (den Hertog et al., *EMBO J.* 13: 3020–3032 (1994); Su et al., *J. Biol. Chem.* 269: 18731–18734 (1994)), a recent study suggests a function for this phosphatase and its close relative PTPe as negative regulators of the insulin receptor signal (Møller et al., 1995 supra). This study also indicates that receptor-like PTPases play a significant role in regulating the IRTK, whereas intracellular PTPases seem to have little, if any, activity towards the insulin receptor. While it appears that the target of the negative regulatory activity of PTPases a and e is the receptor itself, the downmodulating effect of the intracellular TC-PTP seems to be due to a downstream function in the IR-activated signal. Although PTP1B and TC-PTP are closely related, PTP1B had only little influence on the phosphorylation pattern of insulin-treated cells. Both PTPases have distinct structural features that determine their subcellular localization and thereby their access to defined cellular substrates (Frangione et al., *Cell* 68: 545–560 (1992); Faure and Posner, *Glia* 9: 311–314 (1993)). Therefore, the lack of activity of PTP1B and TC-PTP towards the IRTK may, at least in part, be explained by the fact that they do not co-localize with the activated insulin receptor. In support of this view, PTP1B and TC-PTP have been excluded as candidates for the IR-associated PTPases in hepatocytes based on subcellular localization studies (Faure et al., *J. Biol. Chem.* 267: 11215–11221 (1992)).

The transmembrane PTPase CD45, which is believed to be hematopoietic cell-specific, was in a recent study found to negatively regulate the insulin receptor tyrosine kinase in the human multiple myeloma cell line U266 (Kulas et al.,*J. Biol. Chem.* 271: 755–760 (1996)).

PTPases: Somatostatin

Somatostatin inhibits several biological functions including cellular proliferation (Lamberts et al., *Molec. Endocrinol.* 8: 1289–1297 (1994)). While part of the antiproliferative activities of somatostatin are secondary to its inhibition of hormone and growth factor secretion (e.g. growth hormone and epidermal growth factor), other antiproliferative effects of somatostatin are due to a direct effect on the target cells. As an example, somatostatin analogs inhibit the growth of pancreatic cancer presumably via stimulation of a single PTPase, or a subset of PTPases, rather than a general activation of PTPase levels in the cells (Liebow et al., *Proc. Natl. Acad. Sci. USA* 86: 2003–2007 (1989); Colas et al., *Eur. J. Biochem.* 207: 1017–1024 (1992)). In a recent study it was found that somatostatin stimulation of somatostatin receptors SSTR1, but not SSTR2, stably expressed in CHO-K1 cells can stimulate PTPase activity and that this stimulation is pertussis toxin-sensitive. Whether the inhibitory effect of somatostatin on hormone and growth factor secretion is caused by a similar stimulation of PTPase activity in hormone producing cells remains to be determined.

PTPases: The Immune System/Autoimmunity

Several studies suggest that the receptor-type PTPase CD45 plays a critical role not only for initiation of T cell activation, but also for maintaining the T cell receptor-mediated signalling cascade. These studies are reviewed in: (Weiss A., *Ann. Rev. Genet.* 25: 487–510 (1991); Chan et al., *Annu. Rev. Immunol.* 12: 555–592 (1994); Trowbridge and Thomas, *Annu. Rev. Immunol.* 12: 85–116 (1994)).

CD45 is one of the most abundant of the cell surface glycoproteins and is expressed exclusively on hemopoetic cells. In T cells, it has been shown that CD45 is one of the critical components of the signal transduction machinery of lymphocytes. In particular, evidence has suggested that CD45 phosphatase plays a pivotal role in antigen-stimulated proliferation of T lymphocytes after an antigen has bound to the T cell receptor (Trowbridge, *Ann. Rev. Immunol*, 12:85–116 (1994)). Several studies suggest that the PTPase activity of CD45 plays a role in the activation of Lck, a lymphocyte-specific member of the Src family protein-tyrosine kinase (Mustelin et al., Proc. Natl. Acad. Sci. USA 86: 6302–6306 (1989); Ostergaard et al., Proc. Natl. Acad. Sci. USA 86: 8959–8963 (1989)). These authors hypothesized that the phosphatase activity of CD45 activates Lck by dephosphorylation of a C-terminal tyrosine residue, which may, in turn, be related to T-cell activation. In a recent study it was found that re-combinant p56lck specifically associates with recombinant CD45 cytoplasmic domain protein, but not to the cytoplasmic domain of the related PTPa (Ng et al., *J. Biol. Chem.* 271: 1295–1300 (1996)). The p56lck-CD45 interaction seems to be mediated via a non-conventional SH2 domain interaction not requiring phosphotyrosine. In mature B cells, another member of the Src family protein-tyrosine kinases, Fyn, seems to be a selective substrate for CD45 compared to Lck and Syk (Katagiri et al., *J. Biol. Chem.* 270: 27987–27990 (1995)).

Studies using transgenic mice with a mutation for the CD45-exon6 exhibited lacked mature T cells. These mice did not respond to an antigenic challenge with the typical T cell mediated response (Kishihara et al., *Cell* 74:143–56 (1993)). Inhibitors of CD45 phosphatase would therefore be very effective therapeutic agents in conditions that are associated with autoimmune disease.

CD45 has also been shown to be essential for the antibody mediated degranulation of mast cells (Berger et al., *J. Exp. Med.* 180:471–6 (1994)). These studies were also done with mice that were CD45-deficient. In this case, an IgE-mediated degranulation was demonstrated in wild type but not CD45-deficient T cells from mice. These data suggest that CD45 inhibitors could also play a role in the symptomatic or therapeutic treatment of allergic disorders.

Another recently discovered PTPase, an inducible lymphoid-specific protein tyrosine phosphatase (HePTP) has also been implicated in the immune response. This phosphatase is expressed in both resting T and B lymphocytes, but not non-hemopoetic cells. Upon stimulation of these cells, mRNA levels from the HePTP gene increase 10–15 fold (Zanke et al., *Eur. J. Immunol.* 22:235–239 (1992)). In both T and B cells HePTP may function during sustained stimulation to modulate the immune response through dephosphorylation of specific residues. Its exact role, however remains to be defined.

Likewise, the hematopoietic cell specific PTP1C seems to act as a negative regulator and play an essential role in immune cell development.In accordance with the above-mentioned important function of CD45, HePTP and PTP1C, selective PTPase inhibitors may be attractive drug candidates both as immunosuppressors and as immunostimulants. One recent study illustrates the potential of PTPase inhibitors as immunmodulators by demonstrating the capacity of the vanadium-based PTPase inhibitor, BMLOV, to induce apparent B cell selective apoptosis compared to T cells (Schieven et al., *J. Biol. Chem.* 270: 20824–20831 (1995)).

PTPases: Cell-cell Interactions/Cancer

Focal adhesion plaques, an in vitro phenomenon in which specific contact points are formed when fibroblasts grow on appropriate substrates, seem to mimic, at least in part, cells and their natural surroundings. Several focal adhesion proteins are phosphorylated on tyrosine residues when fibroblasts adhere to and spread on extracellular matrix (Gumbiner, *Neuron* 11, 551–564 (1993)). However, aberrant tyrosine phosphorylation of these proteins can lead to cellular transformation. The intimate association between PTPases and focal adhesions is supported by the finding of several intracellular PTPases with ezrin-like N-terminal domains, e.g. PTPMEG1 (Gu et al., *Proc. Natl. Acad. Sci. USA* 88: 5867–5871 (1991)), PTPH1 (Yang and Tonks, *Proc. Natl. Acad. Sci. USA* 88: 5949–5953 (1991)) and PTPD1 (Møller et al., *Proc. Natl. Acad. Sci. USA* 91: 7477–7481 (1994)). The ezrin-like domain show similarity to several proteins that are believed to act as links between the cell membrane and the cytoskeleton. PTPD1 was found to be phosphorylated by and associated with c-src in vitro and is hypothesized to be involved in the regulation of phosphorylation of focal adhesions (Møller et al., supra).

PTPases may oppose the action of tyrosine kinases, including those responsible for phosphorylation of focal adhesion proteins, and may therefore function as natural inhibitors of transformation. TC-PTP, and especially the truncated form of this enzyme (Cool et al., *Proc. Natl. Acad. Sci. USA* 87: 7280–7284 (1990)), can inhibit the transforming activity of v-erb and v-fms (Lammers et al., *J. Biol. Chem.* 268:22456–22462 (1993); Zander et al., *Oncogene* 8: 1175–1182 (1993)). Moreover, it was found that transformation by the oncogenic form of the HER2/neu gene was suppressed in NIH 3T3 fribroblasts overexpressing PTP1B (Brown-Shimer et al., *Cancer Res.* 52:478482 (1992)).

The expression level of PTP1B was found to be increased in a mammary cell line transformed with neu (Zhay et al., *Cancer Res.* 53: 2272–2278 (1993)). The intimate relationship between tyrosine kinases and PTPases in the development of cancer is further evidenced by the recent finding that PTPe is highly expressed in murine mammary tumors in transgenic mice over-expressing c-neu and v-Ha-ras, but not c-myc or int-2 (Elson and Leder, *J. Biol. Chem.* 270:26116–26122 (1995)). Further, the human gene encoding PTPg was mapped to 3p21, a chromosomal region which is frequently deleted in renal and lung carcinomas (LaForgia et al., *Proc. Natl. Acad. Sci. USA* 88: 5036–5040 (1991)).

In this context, it seems significant that PTPases appear to be involved in controlling the growth of fibroblasts. In a recent study it was found that Swiss 3T3 cells harvested at high density contain a membrane-associated PTPase whose activity on an average is 8-fold higher than that of cells harvested at low or medium density (Pallen and Tong, *Proc. Natl. Acad. Sci. USA* 88: 6996–7000 (1991)). It was hypothesized by the authors that density-dependent inhibition of cell growth involves the regulated elevation of the activity of the PTPase(s) in question. In accordance with this view, a novel membrane-bound, receptor-type PTPase, DEP-1, showed enhanced (>=10-fold) expression levels with increasing cell density of WI-38 human embryonic lung fibroblasts and in the AG1518 fibroblast cell line (Östman et at, *Proc. Natl. Acad. Sci. USA* 91: 9680–9684 (1994)).

Two closely related receptor-type PTPases, PTPκ and PTPμ, can mediate homophilic cell-cell interaction when expressed in non-adherent insect cells, suggesting that these PTPases might have a normal physiological function in cell-to-cell signalling (Gebbink et al., *J. Biol. Chem.* 268:16101–16104 (1993); Brady-Kalnay et al., *J. Cell Biol.* 122: 961–972 (1993); Sap et al., *Mol. Cell. Biol.* 14: 1–9 (1994)). Interestingly, PTPk and PTPμ do not interact with each other, despite their structural similarity (Zondag et al., *J. Biol. Chem.* 270: 14247–14250 (1995)). From the studies described above it is apparent that PTPases may play an important role in regulating normal cell growth. However, as pointed out above, recent studies indicate that PTPases may also function as positive mediators of intracellular signalling and thereby induce or enhance mitogenic responses. Increased activity of certain PTPases might therefore result in cellular transformation and tumor formation. Indeed, in one study over-expression of PATα was found to lead to transformation of rat embryo fibroblasts (Zheng, supra). In addition, a novel PTP, SAP-1, was found to be highly expressed in pancreatic and colorectal cancer cells. SAP-1 is mapped to chromosome 19 region q13.4 and might be related to carcinoembryonic antigen mapped to 19q13.2 (Uchida et al., *J. Biol. Chem.* 269:12220–12228 (1994)). Further, the dsPTPase, cdc25, dephosphorylates cdc2 at Thr14fTyr-15 and thereby functions as positive regulator of mitosis (reviewed by Hunter, *Cell* 80: 225–236 (1995)). Inhibitors of specific PTPases are therefore likely to be of significant therapeutic value in the treatment of certain forms of cancer.

PTPases: Platelet Aggregation

Recent studies indicate that PTPases are centrally involved in platelet aggregation. Agonist-induced platelet activation results in calpain-catalyzed cleavage of PTP1B with a concomitant 2-fold stimulation of PTPase activity (Frangioni et al., *EMBO J.* 12:4843–4856 (1993)). The cleavage of PTP1B leads to subcellular relocation of the enzyme and correlates with the transition from reversible to irreversible platelet aggregation in platelet-rich plasma. In addition, the SH2 domain containing PTPase, SHP-1, was found to translocate to the cytoskeleton in platelets after thrombin stimulation in an aggregation-dependent manner (Li et al., *FEBS Lett.* 343: 89–93 (1994)).

Although some details in the above two studies were recently questioned there is over-all agreement that PTP1B and SHP-1 play significant functional roles in platelet aggregation (Ezumi et al., *J. Biol. Chem.* 270:11927–11934 (1995)). In accordance with these observations, treatment of platelets with the PTPase inhibitor pervanadate leads to significant increase in tyrosine phosphorylation, secretion and aggregation (Pumiglia et al., *Biochem. J.* 286: 441–449 (1992)).

PTPases: Osteoporosis

The rate of bone formation is determined by the number and the activity of osteoblasts, which in term are determined by the rate of proliferation and differentiation of osteoblast progenitor cells, respectively. Histomorphometric studies indicate that the osteoblast number is the primary determinant of the rate of bone formation in humans (Gruber et al., *Mineral Electrolyte Metab.* 12: 246–254 (1987); reviewed in Lau et al., *Biochem. J.* 257: 23–36 (1989)). Acid phosphatases/PTPases may be involved in negative regulation of osteoblast proliferation. Thus, fluoride, which has phosphatase inhibitory activity, has been found to increase spinal bone density in osteoporotics by increasing osteoblast proliferation (Lau et al., supra). Consistent with this observation, an osteoblastic acid phosphatase with PTPase activity was found to be highly sensitive to mitogenic concentrations of fluoride (Lau et al., *J. Biol. Chem.* 260: 4653–4660 (1985); Lau et al., *J. Biol. Chem.* 262: 1389–1397 (1987); Lau et al., *Adv. Protein Phosphatases* 4: 165–198 (1987)). Interestingly, it was recently found that the level of membrane-bound PTPase activity was increased dramatically when the osteoblast-like cell line UMR 106.06 was grown on collagen type-I matrix compared to uncoated tissue culture plates. Since a significant increase in PTPase activity was observed in density-dependent growth arrested fibroblasts (Pallen and Tong, *Proc. Natl. Acad. Sci.* 88: 6996–7000 (1991)), it might be speculated that the increased PTPase activity directly inhibits cell growth. The mitogenic action of fluoride and other phosphatase inhibitors (molybdate and vanadate) may thus be explained by their inhibition of acid phosphatases/PTPases that negatively regulate the cell proliferation of osteoblasts. The complex nature of the involvement of PTPases in bone formation is further suggested by the recent identification of a novel parathyroid regulated, receptor-like PTPase, OST-PTP, expressed in bone and testis (Mauro et al., *J. Biol. Chem.* 269: 30659–30667 (1994)). OST-PTP is up-regulated following differentiation and matrix formation of primary osteoblasts and subsequently down-regulated in the osteoblasts which are actively mineralizing bone in culture. It may be hypothesized that PTPase inhibitors may prevent differentiation via inhibition of OST-PTP or other PTPases thereby leading to continued proliferation. This would be in agreement with the above-mentioned effects of fluoride and the observation that the tyrosine phosphatase inhibitor orthovanadate appears to enhance. osteoblast proliferation and matrix formation (Lau et al., *Endocrinology* 116: 2463–2468 (1988)). In addition, it was recently observed that vanadate, vanadyl and pervanadate all increased the growth of the osteoblast-like cell line UMR106. Vanadyl and pervanadate were stronger stimulators of cell growth than vanadate. Only vanadate was able to regulate the cell differentiation as measured by cell alkaline phosphatase activity (Cortizo et al., *Mol. Cell. Biochem.* 145: 97–102 (1995)).

PTPases: Microorganisms

Dixon and coworkers have called attention to the fact that PTPases may be a key element in the pathogenic properties of Yersinia (reviewed in Clemens et al. *Molecular Microbiology* 5: 2617–2620 (1991)). This finding was rather surprising since tyrosine phosphate is thought to be absent in bacteria. The genus Yersinia comprises 3 species: *Y. pestis* (responsible for the bubonic plague), *Y. pseudoturberculosis* and *Y. enterocolitica* (causing enteritis and mesenteric lymphadenitis). Interestingly, a dual-specificity phosphatase, VH1, has been identified in Vaccinia virus (Guan et al., *Nature* 350: 359–263 (1991)). These observations indicate that PTPases may play critical roles in microbial and parasitic infections, and they further point to PTPase inhibitors as a novel, putative treatment principle of infectious diseases.

SUMMARY OF THE INVENTION

The present invention relates to compounds of the general formula I, wherein A, $R_1$, $R_2$, $R_3$, $R_4$, $R_{16}$, and $R_{17}$ are as defined in the detailed part of the present description, wherein such compounds are pharmacologically useful inhibitors of Protein Tyrosine Phosphatases (PTPases) such as PTP1B, CD45, SHP-1, SHP-2, PATα, LAR and HePTP or the like.

The present compounds are useful for the treatment, prevention, elimination, alleviation or amelioration of an indication related to type I diabetes, type II diabetes, impaired glucose tolerance, insulin resistance, obesity, immune dysfunctions including autoimmunity and AIDS, diseases with dysfunctions of the coagulation system, allergic diseases including asthma, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimer's disease and schizophrenia, and infectious diseases.

In another aspect, the present invention includes within its scope pharmaceutical compositions comprising, as an active ingredient, at least one of the compounds of the general formula I or a pharmaceutically acceptable salt thereof together with a pharmaceutically acceptable carrier or diluent.

In another aspect of the present invention there is provided a method of treating type I diabetes, type II diabetes, impaired glucose tolerance, insulin resistance, obesity, immune dysfunctions including autoimmunity and AIDS, diseases with dysfunctions of the coagulation system, allergic diseases including asthma, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimer's disease and schizophrenia, and infectious diseases.

The method of treatment may be described as the treatment, prevention, elimination, alleviation or amelioration of one of the above indications, which comprises the step of administering to the said subject a neurologically effective amount of a compound of the invention, or a pharmaceutically acceptable salt thereof.

A further aspect of the invention relates to the use of a compound of the present invention for the preparation of a pharmaceutical composition for the treatment of all type I diabetes, type II diabetes, impaired glucose tolerance, insulin resistance, obesity, immune dysfunctions including autoimmunity and AIDS, diseases with dysfunctions of the coagulation system, allergic diseases including asthma, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimer's disease and schizophrenia, and infectious diseases.

DESCRIPTION OF THE INVENTION

The present invention relates to Compounds of the Formula 1 wherein A, $R_1$, $R_2$, $R_3$, $R_4$, $R_{16}$ and $R_{17}$ are defined below;

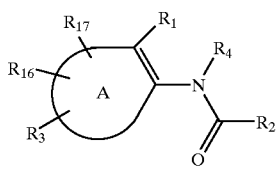

Formula 1

In the above Formula 1

A is together with the double bond in Formula 1 indolyl, benzo[b]thiophenyl, benzo[b]furanyl, indazolyl, benzo[b]isoxazolyl, benzimidazolyl, benzthiazolyl, benzoxazolyl, 9H-thieno[2,3-c]chromenyl, 4,5,6,7-tetrahydro-benzo[b]thiophenyl, 4,5,6,7-tetrahydro-thieno[2,3-b]pyridyl, 4,5,6,7-tetrahydro-thieno[2,3-c]pyridyl, 4,5,6,7-tetrahydro-thieno[3,2-c]pyridyl, 4,5,6,7-tetrahydro-thieno[3,2-b]pyridyl, 4,7-dihydro-5H-thieno[2,3-c]pyridyl, 4,7-dihydro-5H-thieno[2,3-c]thiopyranyl or 4,5,6,7-tetrahydro-4,7-ethanon-thieno[2,3-b]pyridyl;

$R_1$ is hydrogen, $COR_5$, $OR_6$, $CF_3$, nitro, cyano, $SO_3H$, $SO_2NR_7R_8$, $PO(OH)_2$, $CH_2PO(OH)_2$, $CHFPO(OH)_2$, $CF_2PO(OH)_2$, $C(=NH)NH_2$, $NR_7R_8$ or selected from the following 5-membered heterocycles:

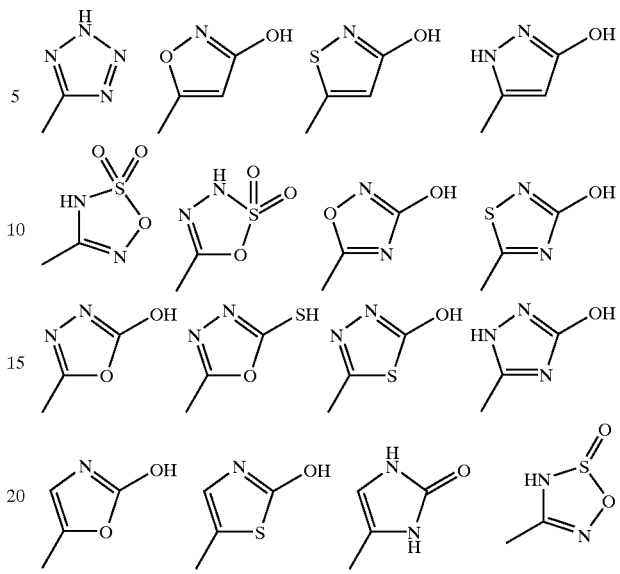

or R, is

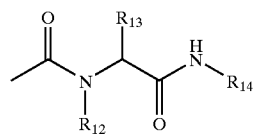

wherein $R_{12}$, $R_{13}$, and $R_{14}$ are independently hydrogen, $C_1-C_6$alkyl, aryl, aryl$C_1-C_6$alkyl and the alkyl and aryl groups are optionally substituted;

$R_2$ is $COR_5$, $OR_6$, $CF_3$, nitro, cyano, $SO_3H$, $SO_2NR_7R_8$, $PO(OH)_2$, $CH_2PO(OH)_2$, $CHFPO(OH)_2$, $CF_2PO(OH)_2$, $C(=NH)NH_2$, $NR_7R_8$, or selected from the following 5-membered heterocycles:

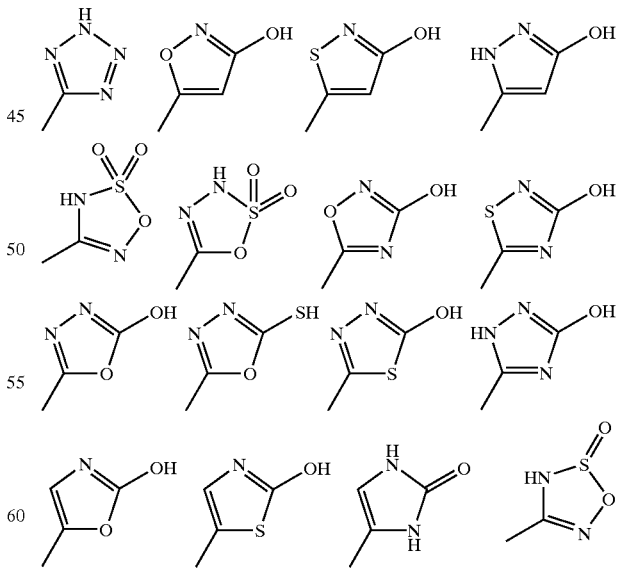

$R_3$, $R_{16}$ and $R_{17}$ are independently hydrogen, halo, nitro, cyano, trihalomethyl, $C_1-C_6$alkyl, aryl, aryl$C_1-C_6$alkyl, hydroxy, oxo, carboxy, carboxy$C_1-C_6$alkyl, $C_1-C_6$alkyloxycarbonyl, aryloxycarbonyl, arylC$_1$–C$_6$alkyloxycarbonyl, C$_1$–C$_6$alkyloxy, C$_1$–C$_6$alkyloxyC$_1$–C$_6$alkyl, aryloxy, arylC$_1$–C$_6$alkyloxy, arylC$_1$–C$_6$alkyloxyC$_1$–C$_6$alkyl, thio, C$_1$–C$_6$alkylthio, C$_1$–C$_6$alkylthioC$_1$–C$_6$alkyl, arylthio, arylC$_1$–C$_6$alkylthio, arylC$_1$–C$_6$alkylthioC$_1$–C$_6$alkyl, NR$_7$R$_8$, C$_1$–C$_6$alkylaminoC$_1$–C$_6$alkyl, arylC$_1$–C$_6$alkylaminoC$_1$–C$_6$alkyl, di(arylC$_1$–C$_6$alkyl)aminoC$_1$–C$_6$alkyl, C$_1$–C$_6$alkylcarbonyl, C$_1$–C$_6$alkylcarbonyl-C$_1$–C$_6$alkyl, arylC$_1$–C$_6$alkylcarbonyl, arylC$_1$–C$_6$alkylcarbonylC$_1$–C$_6$alkyl, C$_1$–C$_6$alkylcarboxy, C$_1$–C$_6$alkylcarboxyC$_1$–C$_6$-alkyl, arylcarboxy, arylcarboxyC$_1$–C$_6$alkyl, arylC$_1$–C$_6$alkylcarboxy, arylC$_1$–C$_6$alkylcarboxyC$_1$–C$_6$alkyl, C$_1$–C$_6$alkylcarbonylamino, C$_1$–C$_6$alkylcarbonylaminoC$_1$–C$_6$alkyl, -carbonylNR$_7$C$_1$–C$_6$alkylCOR$_{11}$, arylC$_1$–C$_6$alkylcarbonylamino, arylC$_1$–C$_6$alkylcarbonylaminoC$_1$–C$_6$alkyl, CONR$_7$R$_8$, or C$_1$–C$_6$alkylCONR$_7$R$_8$ wherein the alkyl and aryl groups are optionally substituted and R$_{11}$ is NR$_7$R$_8$, or C$_1$–C$_6$alkylNR$_7$R$_8$; or R$_3$ is

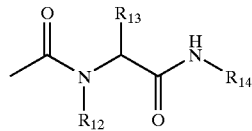

wherein R$_{12}$, R$_{13}$, and R$_{14}$ are independently hydrogen, C$_1$–C$_6$alkyl, aryl, arylC$_1$–C$_6$alkyl and the alkyl and aryl groups are optionally substituted;

R$_4$ is hydrogen, hydroxy, C$_1$–C$_6$alkyl, aryl, arylC$_1$–C$_6$alkyl, NR$_7$R$_8$, C$_1$–C$_6$alkyloxy; wherein the alkyl and aryl groups are optionally substituted;

R$_5$ is hydroxy, C$_1$–C$_6$alkyl, aryl, arylC$_1$–C$_6$alkyl, C$_1$–C$_6$alkyloxy, C$_1$–C$_6$alkyl-oxyC$_1$–C$_6$alkyloxy, aryloxy, arylC$_1$–C$_6$alkyloxy, CF$_3$, NR$_7$R$_8$; wherein the alkyl and aryl groups are optionally substituted;

R$_6$ is hydrogen, C$_1$–C$_6$alkyl, aryl, arylC$_1$–C$_6$alkyl; wherein the alkyl and aryl groups are optionally substituted;

R$_7$ and R$_8$ are independently selected from hydrogen, C$_1$–C$_6$alkyl, aryl, arylC$_1$–C$_6$alkyl, C$_1$–C$_6$alkylcarbonyl, arylcarbonyl, arylC$_1$–C$_6$alkylcarbonyl, C$_1$–C$_6$alkylcarboxy or arylC$_1$–C$_6$alkylcarboxy wherein the alkyl and aryl groups are optionally substituted; or R$_7$ and R$_8$ are together with the nitrogen to which they are attached forming a saturated, partially saturated or aromatic cyclic, bicyclic or tricyclic ring system containing from 3 to 14 carbon atoms and from 0 to 3 additional heteroatoms selected from nitrogen, oxygen or sulfur, the ring system can optionally be substituted with at least one C$_1$–C$_6$alkyl, aryl, arylC$_1$–C$_6$alkyl, hydroxy, oxo, C$_1$–C$_6$alkyloxy, arylC$_1$–C$_6$alkyloxy, C$_1$–C$_6$alkyloxyC$_1$–C$_6$alkyl, NR$_9$R$_{10}$ or C$_1$–C$_6$alkylamino-C$_1$–C$_6$alkyl, wherein R$_9$ and R$_{10}$, are independently selected from hydrogen, C$_1$–C$_6$alkyl, aryl, arylC$_1$–C$_6$alkyl, C$_1$–C$_6$alkylcarbonyl, arylcarbonyl, arylC$_1$–C$_6$alkylcarbonyl, C$_1$–C$_6$alkylcarboxy or arylC$_1$–C$_6$alkylcarboxy; wherein the alkyl and aryl groups are optionally substituted; or R$_7$ and R$_8$ are independently a saturated or partial saturated cyclic 5,6 or 7 membered amine, imide or lactam;

or a salt thereof with a pharmaceutically acceptable acid or base, or any optical isomer or mixture of optical isomers, including a racemic mixture, or any tautomeric forms.

DEFINITIONS

Signal transduction is a collective term used to define all cellular processes that follow the activation of a given cell or tissue. Examples of signal transduction, which are not intended to be in any way limiting to the scope of the invention claimed, are cellular events that are induced by polypeptide hormones and growth factors (e.g. insulin, insulin-like growth factors I and II, growth hormone, epidermal growth factor, platelet-derived growth factor), cytokines (e.g. interleukins), extracellular matrix components, and cell-cell interactions.

Phosphotyrosine recognition unitsityrosine phosphate recognition units/pTyr recognition units are defined as areas or domains of proteins or gly-coproteins that have affinity for molecules containing phosphorylated tyrosine residues (pTyr). Examples of pTyr recognition units, which are not intended to be in any way limiting to the scope of the invention claimed, are: PTPases, SH2 domains and PTB domains.

PTPases are defined as enzymes with the capacity to dephosphorylate pTyr-containing proteins or glycoproteins. Examples of PTPases, which are not intended to be in any way limiting to the scope of the invention claimed, are: 'classical' PTPases (intracellular PTPases (e.g. PTP1B, TC-PTP, PTP1C, PTP1D, PTPD1, PTPD2) and receptor-type PTPases (e.g. PATα, PTPε, PTPβ, PTPγ, CD45, PTPκ, PTPμ), dual specificty phosphatases (VH1, VHR, cdc25), LMW-PTPases or acid phosphatases.

SH2 domains (Src homology 2 domains) are non-catalytic protein modules that bind to pTyr (phosphotyrosine residue) containing proteins, i.e. SH2 domains are pTyr recognition units. SH2 domains, which consist of ~100 amino acid residues, are found in a number of different molecules involved in signal transduction processes. The following is a non-limiting list of proteins containing SH2 domains: Src, Hck, Lck, Syk, Zap70, SHP-1, SHP-2, STATs, Grb-2, Shc, p85/PI3K, Gap, vav (see Russell et al., *FEBS Lett.* 304:15–20 (1992); Pawson, *Nature* 373: 573–580 (1995); Sawyer, Biopolymers (Peptide Science) 47: 243–261 (1998); and references herein).

As used herein, the term "attached" or "–" (e.g. —COR$_{11}$ which indicates the carbonyl attachment point to the scaffold) signifies a stable covalent bond, certain preferred points of attachment points being apparent to those skilled in the art. The terms "halogen" or "halo" include fluorine, chlorine, bromine, and iodine. The term "alkyl" includes C$_1$–C$_6$ straight chain saturated, methylene and C$_2$–C$_6$ unsaturated aliphatic hydrocarbon groups, C$_1$–C$_6$ branched saturated and C$_2$–C$_6$ unsaturated aliphatic hydrocarbon groups, C$_3$–C$_6$ cyclic saturated and C$_5$–C$_6$ unsaturated aliphatic hydrocarbon groups, and C$_1$–C$_6$ straight chain or branched saturated and C$_2$–C$_6$ straight chain or branched unsaturated aliphatic hydrocarbon groups substituted with C$_3$–C$_5$ cyclic saturated and unsaturated aliphatic hydrocarbon groups having the specified number of carbon atoms. For example, this definition shall include but is not limited to methyl (Me), ethyl (Et), propyl (Pr), butyl (Bu), pentyl, hexyl, heptyl, ethenyl, propenyl, butenyl, penentyl, hexenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cyclopentenyl, cyclohexenyl, methylcyclopropyl, ethylcyclohexenyl, butenylcyclopentyl, and the like.

The term "substituted alkyl" represents an alkyl group as defined above wherein the substitutents are independently selected from halo, cyano, nitro, trihalomethyl, carbamoyl, hydroxy, oxo, $COR_5$, $C_1$–$C_6$alkyl, $C_1$–$C_6$alkyloxy, aryloxy, aryl$C_1$–$C_6$alkyloxy, thio, $C_1$–$C_6$alkylthio, arylthio, aryl$C_1$–$C_6$alkylthio, $NR_7R_8$, $C_1$–$C_6$alkylamino, arylamino, aryl$C_1$–$C_6$alkylamino, di(aryl$C_1$–$C_6$alkyl)amino, $C_1$–$C_6$alkylcarbonyl, aryl$C_1$–$C_6$alkylcarbonyl, $C_1$–$C_6$alkylcarboxy, arylcarboxy, aryl$C_1$–$C_6$alkylcarboxy, $C_1$–$C_6$alkylcarbonyl-amino, —$C_1$–$C_6$alkylamino$COR_{11}$, aryl$C_1$–$C_6$alkylcarbonylamino, tetrahydrofuranyl, morpholinyl, piperazinyl, —$CONR_7R_8$, —$C_1$–$C_6$alkyl-$CONR_7R_8$, or a saturated or partial saturated cyclic 5, 6 or 7 membered amine, imide or lactam; wherein $R_{11}$ is hydroxy, $C_1$–$C_6$alkyl, aryl, aryl$C_1$–$C_6$alkyl, $C_1$–$C_6$alkyloxy, aryloxy, aryl$C_1$–$C_6$alkyloxy and $R_5$ is defined as above or $NR_7R_8$, wherein $R_7$, $R_8$ are defined as above.

The term "saturated, partially saturated or aromatic cyclic, bicyclic or tricyclic ring system" represents but are not limit to aziridinyl, pyrrolyl, pyrrolinyl, pyrrolidinyl, imidazolyl, 2-imidazolinyl, imidazolidinyl, pyrazolyl, 2-pyrazolinyl, 1,2,3-triazolyl, 1,2,4-triazolyl, morpholinyl, piperidinyl, thiomorpholinyl, piperazinyl, indolyl, isoindolyl, 1,2,3,4-tetrahydro-quinolinyl, 1,2,3,4-tetrahydro-isoquinolinyl, 1,2,3,4-tetrahydro-quinoxalinyl, indolinyl, indazolyl, benzimidazolyl, benzotriazolyl, purinyl, carbazolyl, acridinyl, phenothiazinyl, phenoxazinyl, iminodibenzyl, iminostilbenyl.

The term "alkyloxy" (e.g. methoxy, ethoxy, propyloxy, allyloxy, cyclohexyloxy) represents an "alkyl" group as defined above having the indicated number of carbon atoms attached through an oxygen bridge. The term "alkyloxyalkyl" represents an "alkyloxy" group attached through an alkyl group as defined above having the indicated number of carbon atoms.

The term "alkyloxyalkyloxy" represents an "alkyloxyalkyl" group attached through an oxygen atom as defined above having the indicated number of carbon atoms.

The term "aryloxy" (e.g. phenoxy, naphthyloxy and the like) represents an aryl group as defined below attached through an oxygen bridge.

The term "arylalkyloxy" (e.g. phenethyloxy, naphthylmethyloxy and the like) represents an "arylalkyl" group as defined below attached through an oxygen bridge.

The term "arylalkyloxyalkyl" represents an "arylalkyloxy" group as defined above attached through an "alkyl" group defined above having the indicated number of carbon atoms.

The term "arylthio" (e.g. phenylthio, naphthylthio and the like) represents an "aryl" group as defined below attached through an sulfur bridge.

The term "alkyloxycarbonyl" (e.g. methylformiat, ethylformiat and the like) represents an "alkyloxy" group as defined above attached through a carbonyl group.

The term "aryloxycarbonyl" (e.g. phenylformiat, 2-thiazolylformiat and the like) represents an "aryloxy" group as defined above attached through a carbonyl group.

The term "arylalkyloxycarbonyl" (e.g. benzylformiat, phenyletylformiat and the like) represents an "arylalkyloxy" group as defined above attached through a carbonyl group.

The term "alkyloxycarbonylalkyl" represents an "alkyloxycarbonyl" group as defined above attached through an "alkyl" group as defined above having the indicated number of carbon atoms.

The term "arylalkyloxycarbonylalkyl" represents an "arylalkyloxycarbonyl" group as defined above attached through an "alkyl" group as defined above having the indicated number of carbon atoms.

The term "alkylthio" (e.g. methylthio, ethylthio, propylthio, cyclohexenylthio and the like) represents an "alkyl" group as defined above having the indicated number of carbon atoms attached through a sulfur bridge.

The term "arylalkylthio" (e.g. phenylmethylthio, phenylethylthio, and the like) represents an "arylalkyl" group as defined above having the indicated number of carbon atoms attached through a sulfur bridge.

The term "alkylthioalkyl" represents an "alkylthio" group attached through an alkyl group as defined above having the indicated number of carbon atoms.

The term "arylalkylthioalkyl" represents an "arylalkylthio" group attached through an alkyl group as defined above having the indicated number of carbon atoms.

The term "alkylamino" (e.g. methylamino, diethylamino, butylamino, N-propyl-N-hexylamino, (2-cyclopentyl) propylamino, hexenylamino, pyrrolidinyl, piperidinyl and the like) represents one or two "alkyl" groups as defined above having the indicated number of carbon atoms attached through an amine bridge. The two alkyl groups may be taken together with the nitrogen to which they are attached forming a saturated, partially saturated or aromatic cyclic, bicyclic or tricyclic ring system containing 3 to 14 carbon atoms and 0 to 3 additional heteroatoms selected from nitrogen, oxygen or sulfur, the ring system can optionally be substituted with at least one $C_1$–$C_6$alkyl, aryl, aryl$C_1$–$C_6$alkyl, hydroxy, oxo, $C_1$–$C_6$alkyloxy, $C_1$–$C_6$alkyloxy$C_1$–$C_6$alkyl, $NR_9R_{10}$, $C_1$–$C_6$alkylamino$C_1$–$C_6$alkyl substituent wherein the alkyl and aryl groups are optionally substituted as defined in the definition section and $R_9$ and $R_{10}$ are defined as above.

The term "arylalkylamino" (e.g. benzylamino, diphenylethylamino and the like) represents one or two "arylalkyl" groups as defined above having the indicated number of carbon atoms attached through an amine bridge. The two "arylalkyl" groups may be taken together with the nitrogen to which they are attached forming a saturated, partially saturated or aromatic cyclic, bicyclic or tricyclic ring system containing 3 to 14 carbon atoms and 0 to 3 additional heteroatoms selected from nitrogen, oxygen or sulfur, the ring system can optionally be substituted with at least one $C_1$–$C_6$alkyl, aryl, aryl$C_1$–$C_6$alkyl, hydroxy, oxo, $C_1$–$C_6$alkyloxy, $C_1$–$C_6$alkyloxy$C_1$–$C_6$alkyl, $NR_9R_{10}$, $C_1$–$C_6$alkylamino$C_1$–$C_6$alkyl substituent wherein the alkyl and aryl groups are optionally substituted as defined in the definition section and $R_9$ and $R_{10}$ are defined as above.

The term "alkylaminoalkyl" represents an "alkylamino" group attached through an alkyl group as defined above having the indicated number of carbon atoms.

The term "arylalkylaminoalkyl" represents an "arylalkylamino" group attached through an alkyl group as defined above having the indicated number of carbon atoms.

The term "arylalkyl" (e.g. benzyl, phenylethyl) represents an "aryl" group as defined below attached through an alkyl having the indicated number of carbon atoms or substituted alkyl group as defined above.

The term "alkylcarbonyl" (e.g. cyclooctylcarbonyl, pentylcarbonyl, 3-hexenylcarbonyl) represents an "alkyl" group as defined above having the indicated number of carbon atoms attached through a carbonyl group.

The term "arylcarbonyl" (benzoyl) represents an "aryl" group as defined above attached through a carbonyl group.

The term "arylalkylcarbonyl" (e.g. phenylcyclopropylcarbonyl, phenylethylcarbonyl and the like) represents an "arylalkyl" group as defined above having the indicated number of carbon atoms attached through a carbonyl group.

The term "alkylcarbonylalkyl" represents an "alkylcarbonyl" group attached through an "alkyl" group as defined above having the indicated number of carbon atoms.

The term "arylalkylcarbonytalkyl" represents an "arylalkylcarbonyl" group attached through an alkyl group as defined above having the indicated number of carbon atoms.

The term "alkylcarboxy" (e.g. heptylcarboxy, cyclopropylcarboxy, 3-pentenylcarboxy) represents an "alkylcarbonyl" group as defined above wherein the carbonyl is in turn attached through an oxygen bridge.

The term "arylcarboxyalkyl" (e.g. phenylcarboxymethyl) represents an "arylcarbonyl" group defined above wherein the carbonyl is in turn attached through an oxygen bridge to an alkyl chain having the indicated number of carbon atoms.

The term "arylalkylcarboxy" (e.g. benzylcarboxy, phenylcyclopropylcarboxy and the like) represents an "arylalkylcarbonyl" group as defined above wherein the carbonyl is in turn attached through an oxygen bridge.

The term "alkylcarboxyalkyl" represents an "alkylcarboxy" group attached through an "alkyl" group as defined above having the indicated number of carbon atoms.

The term "arylalkylcarboxyalkyl" represents an "arylalkylcarboxy" group attached through an "alkyl" group as defined above having the indicated number of carbon atoms.

The term "alkylcarbonylamino" (e.g. hexylcarbonylamino, cyclopentylcarbonyl-aminomethyl, methylcarbonylaminophenyl) represents an "alkylcarbonyl" group as defined above wherein the carbonyl is in turn attached through the nitrogen atom of an amino group. The nitrogen atom may itself be substituted with an alkyl or aryl group.

The term "arylalkylcarbonylamino" (e.g. benzylcarbonylamino and the like) represents an "arylalkylcarbonyl" group as defined above wherein the carbonyl is in turn attached through the nitrogen atom of an amino group. The nitrogen atom may itself be substituted with an alkyl or aryl group.

The term "alkylcarbonylaminoalkyl" represents an "alkylcarbonylamino" group attached through an "alkyl" group as defined above having the indicated number of carbon atoms. The nitrogen atom may itself be substituted with an alkyl or aryl group.

The term "arylalkylcarbonylaminoalkyl" represents an "arylalkylcarbonylamino" group attached through an "alkyl" group as defined above having the indicated number of carbon atoms. The nitrogen atom may itself be substituted with an alkyl or aryl group.

The term "alkylcarbonylaminoalkylcarbonyl" represents an alkylcarbonylaminoalkyl group attached through a carbonyl group. The nitrogen atom may be further substituted with an "alkyl" or "aryl" group.

The term "aryl" represents an unsubstituted, mono-, di- or trisubstituted monocyclic, polycyclic, biaryl and heterocyclic aromatic groups covalently attached at any ring position capable of forming a stable covalent bond, certain preferred points of attachment being apparent to those skilled in the art (e.g., 3-indolyl, 4-imidazolyl). The aryl substituents are independently selected from the group consisting of halo, nitro, cyano, trihalomethyl, $C_1$–$C_6$alkyl, aryl, aryl$C_1$–$C_6$alkyl, hydroxy, $COR_5$, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$alkyl, thio, $C_1$–$C_6$alkylthio, $C_1$–$C_6$alkylthio$C_1$–$C_6$alkyl, arylthio, aryl$C_1$–$C_6$alkylthio, aryl$C_1$–$C_6$alkylthio$C_1$–$C_6$alkyl, $NR_8R_9$, $C_1$–$C_6$-alkylamino, $C_1$–$C_6$alkylamino$C_1$–$C_6$alkyl, arylamino, aryl$C_1$–$C_6$alkylamino, aryl$C_1$–$C_6$alkyl-amino$C_1$–$C_6$alkyl, di(aryl$C_1$–$C_6$alkyl)amino$C_1$–$C_6$alkyl, $C_1$–$C_6$alkylcarbonyl, $C_1$–$C_6$alkylcarbonyl$C_1$–$C_6$alkyl, aryl$C_1$–$C_6$alkylcarbonyl, aryl$C_1$–$C_6$alkyl-carbonyl$C_1$–$C_6$alkyl, $C_1$–$C_6$alkylcarboxy, $C_1$–$C_6$alkylcarboxy-$C_1$–$C_6$alkyl, aryl$C_1$–$C_6$alkylcarboxy, aryl$C_1$–$C_6$alkylcarboxy$C_1$–$C_6$alkyl, carboxy$C_1$–$C_6$alkyloxy, $C_1$–$C_6$alkylcarbonylamino, $C_1$–$C_6$alkylcarbonylamino$C_1$–$C_6$alkyl, -carbonyl$NR_7C_1$–$C_6$alkyl$COR_{11}$, aryl$C_1$–$C_6$alkylcarbonylamino, aryl$C_1$–$C_6$alkylcarbonylamino$C_1$–$C_6$alkyl, —$CONR_8R_9$, or —$C_1$–$C_6$alkyl$CONR_8R_9$; wherein $R_7$, $R_8$, $R_9$, and $R_{11}$ are defined as above and the alkyl and aryl groups are optionally substituted as defined in the definition section;

The definition of aryl includes but is not limited to phenyl, biphenyl, indenyl, fluorenyl, naphthyl (1-naphthyl, 2-naphthyl), pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl 5-oxazolyl), isoxazolyl (3-isoxazolyl, 4-isoxazolyl, 5-isoxazolyl), thiazolyl (2-thiazolyl, 4-thiazolyl, 5-thiazolyl), thiophenyl (2-thiophenyl, 3-thiophenyl, 4-thiophenyl, 5-thiophenyl), furanyl (2-furanyl, 3-furanyl, 4-furanyl, 5-furanyl), pyridyl (2-pyridyl, 3-pyridyl, 4-pyridyl, 5-pyridyl), 5-tetrazolyl, pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo-[b]furanyl), 6-(2,3-dihydro-benzo-[b]furanyl), 7-(2,3-dihydro-benzo[b]furanyl)), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]-thiophenyl (2-(2,3-dihydro-benzo[b]thiophenyl), 3-(2,3-dihydro-benzo[b]-thiophenyl), 4-(2,3-dihydro-benzo[b]thiophenyl), 5-(2,3-dihydro-benzo[b]-thiophenyl), 6-(2,3-dihydro-benzo[b]thiophenyl), 7-(2,3-dihydro-benzo[b]-thiophenyl)), 4,5,6,7-tetrahydro-benzo[b]thiophenyl (2-(4,5,6,7tetrahydro-benzo-[b]thiophenyl), 3-(4,5,6,7-tetrahydro-benzo-[b]thiophenyl), 4-(4,5,6,7-tetrahydro-benzo[b]thiophenyl), 5-(4,5,6,7-tetrahydro-benzo-[b]thiophenyl), 6-(4,5,6,7-tetrahydro-benzo-[b]thiophenyl), 7-(4,5,6,7-tetrahydro-benzo[b]thiophenyl)), 4,5,6,7-tetrahydro-thieno [2,3-c]pyridyl (4-(4,5,6,7-tetrahydro-thieno[2,3-c]pyridyl), 5-4,5,6,7-tetrahydro-thieno[2,3-c]pyridyl), 6-(4,5,6,7-tetrahydro-thieno[2,3-c]pyridyl), 7-(4,5,6,7-tetrahydro-thieno[2,3-c]pyridyl)), indolyl (1-indolyl, 2-indolyl, 3-indolyl, 4-indolyl, 5-indolyl, 6-indolyl, 7-indolyl), isoindolyl (1-isoindolyl, 2-isoindolyl, 3-isoindolyl, 4-isoindolyl, 5-isoindolyl, 6-isoindolyl, 7-isoindolyl), 1,3-dihydro-isoindolyl (1-(1,3-dihydro-isoindolyl), 2-(1,3-dihydro-isoindolyl), 3-(1,3-dihydro-isoindolyl), 4-(1,3-dihydro-isoindolyl), 5-(1,3-dihydro-isoindolyl), 6-(1,3-dihydro-isoindolyl), 7-(1,3-dihydro-isoindolyl)), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benz-oxazolyl, 2-benzoxazolyl), benzothiazolyl (1-benzothiazolyl, 2-benzo-thiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz-[b,f]azepine-2-yl, 5H-dibenz[b,f]azepine-3-yl, 5H-dibenz-[b,f]azepine-4-yl, 5H-dibenz[b,f]-azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz-[b,f]azepine4-yl, 10,11-dihydro-5H-dibenz[b,f]azepine-5-yl), piperidinyl (2-piperidinyl, 3-piperidinyl, 4-piperidinyl), pyrrolidinyl (1-pyrrolidinyl, 2-pyrrolidinyl, 3-pyrrolidinyl), phenylpyridyl (2-phenyl-pyridyl, 3-phenyl-pyridyl, 4-phenylpyridyi), phenylpyrimidinyl (2-phenylpyrimidinyl, 4-phenylpyrimidinyl, 5-phenylpyrimidinyl, 6-phenylpyrimidinyl), phenylpyrazinyl, phenylpyridazinyl (3-phenylpyridazinyl, 4-phenylpyridazinyl, 5-phenylpyridazinyl).

The term "arylcarbonyl" (e.g. 2-thiophenylcarbonyl, 3-methoxy-anthrylcarbonyl, oxazolylcarbonyl) represents an "aryl" group as defined above attached through a carbonyl group.

The term "arylalkylcarbonyl" (e.g. (2,3-dimethoxyphenyl)propylcarbonyl, (2-chloronaphthyl) pentenylcarbonyl, imidazolylcyclopentylcarbonyl) represents an "arylalkyl" group as defined above wherein the "alkyl" group is in turn attached through a carbonyl.

The compounds of the present invention have asymmetric centers and may occur as racemates, racemic mixtures, and as individual enantiomers or diastereoisomers, with all isomeric forms being included in the present invention as well as mixtures thereof.

Pharmaceutically acceptable salts of the compounds of formula 1, where a basic or acidic group is present in the structure, are also included within the scope of this invention. When an acidic substituent is present, such as —COOH, 5-tetrazolyl or —P(O)(OH)$_2$, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, rmandelate, benzoate, cinnamate, methanesulfonate, ethane sulfonate, picrate and the like, and include acids related to the pharmaceutically acceptable salts listed in Journal of Pharmaceutical Science, 66, 2 (1977) and incorporated herein by reference, can be used as the dosage form.

Also, in the case of the —COOH or —P(O)(OH)$_2$ being present, pharmaceutically acceptable esters can be employed, e.g., methyl, tert-butyl, pivaloyloxymethyl, and the like, and those esters known in the art for modifying solubility or hydrolysis characteristics for use as sustained release or prodrug formulations.

In addition, some of the compounds of the instant invention may form solvates with water or common organic solvents. Such solvates are encompassed within the scope of the invention.

The term "therapeutically effective amount" shall mean that amount of drug or pharmaceutical agent that will elicit the biological or medical response of a tissue, system, animal, or human that is being sought by a researcher, veterinarian, medical doctor or other.

PREFERRED EMBODIMENTS OF THE INVENTION

Compounds of Formula 1a are preferred compounds of the invention

Formula 1a

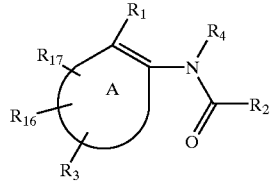

wherein

A is together with the double bond in Formula 1a indolyl, benzo[b]thiophenyl, benzo[b]furanyl, indazolyl, benzo[b]isoxazolyl, benzimidazolyl, benzthiazolyl, benzoxazolyl, 4,5,6,7-tetrahydro-thieno[2,3-b]pyridyl, 4,5,6,7-tetrahydro-thieno[2,3-c]pyridyl, 4,5,6,7-tetrahydro-thieno[3,2-c]pyridyl, 4,5,6,7-tetrahydro-thieno[3,2-b]pyridyl, 4,7-dihydro-5H-thieno[2,3-c]pyridyl or 4,5,6,7-tetrahydro-4,7-etnanon-thieno[2,3-b]pyridyl;

$R_1$ is $COR_5$, $OR_6$, $CF_3$, nitro, cyano, $SO_3H$, $SO_2NR_7R_8$, $PO(OH)_2$, $CH_2PO(OH)_2$, $CHFPO(OH)_2$, $CF_2PO(OH)_2$, $C(=NH)NH_2$, $NR_7R_8$ or selected from the following 5-membered heterocycles:

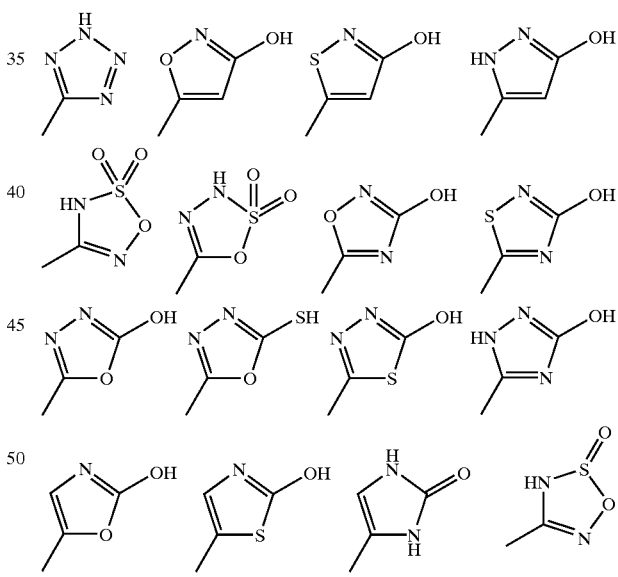

or $R_1$ is

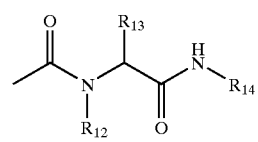

wherein $R_{12}$, $R_{13}$ and $R_{14}$ are independently hydrogen, $C_1$–$C_6$alkyl, aryl, aryl$C_1$–$C_6$alkyl and the alkyl and aryl groups are optionally substituted;

$R_2$ is $COR_5$, $OR_6$, $CF_3$, nitro, cyano, $SO_3H$, $SO_2NR_7R_8$, $PO(OH)_2$, $CH_2PO(OH)_2$, $CHFPO(OH)_2$, $CF_2PO(OH)_2$, $C(=NH)NH_2$, $NR_7R_6$, or selected from the following 5-membered heterocycles:

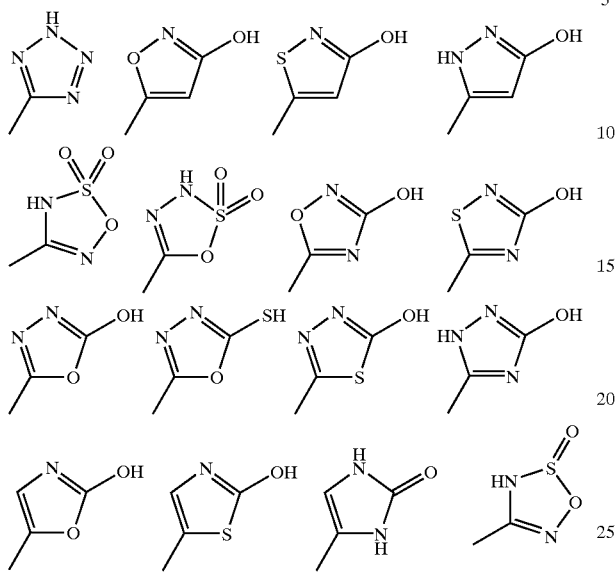

$R_3$, $R_{16}$ and $R_{17}$ are independently hydrogen, halo, nitro, cyano, trihalomethyl, $C_1-C_6$alkyl, aryl, aryl$C_1-C_6$-alkyl, hydroxy, carboxy, carboxy$C_1-C_6$alkyl, $C_1-C_6$alkyloxy-carbonyl, aryloxycarbonyl, aryl$C_1-C_6$alkyloxycarbonyl, $C_1-C_6$alkyloxy, $C_1-C_6$alkyl-oxy$C_1-C_6$alkyl, aryloxy, aryl$C_1-C_6$alkyloxy, aryl$C_1-C_6$alkyl-oxy$C_1-C_6$alkyl, thio, $C_1-C_6$alkylthio, $C_1-C_6$alkylthio$C_1-C_6$alkyl, arylthio, aryl$C_1-C_6$alkylthio, aryl$C_1-C_6$alkylthio$C_1-C_6$alkyl, $NR_7R_8$, $C_1-C_6$alkyl-amino$C_1-C_6$alkyl, aryl$C_1-C_6$alkylamino$C_1-C_6$alkyl, di(aryl$C_1-C_6$alkyl)-amino$C_1-C_6$alkyl, $C_1-C_6$alkylcarbonyl, $C_1-C_6$alkylcarbonyl$C_1-C_6$alkyl, aryl$C_1-C_6$alkylcarbonyl, aryl$C_1-C_6$alkylcarbonyl$C_1-C_6$alkyl, $C_1-C_6$alkyl-carboxy, $C_1-C_6$alkylcarboxy$C_1-C_6$-alkyl, arylcarboxy, aryl$C_1-C_6$alkyl-carboxy, aryl$C_1-C_6$alkylcarboxy$C_1-C_6$alkyl, $C_1-C_6$alkylcarbonylamino, $C_1-C_6$alkylcarbonyl-amino$C_1-C_6$alkyl, -carbonyl$NR_7C_1-C_6$alkyl$COR_{11}$, aryl$C_1-C_6$alkyl-carbonylamino, aryl$C_1-C_6$alkylcarbonylamino$C_1-C_6$alkyl, $CONR_7R_8$, or $C_1-C_6$alkyl$CONR_7R_8$ wherein the alkyl and aryl groups are optionally substituted and $R_{11}$ is $NR_7R_6$, or $C_1-C_6$alkyl$NR_7R_8$; or $R_3$ is

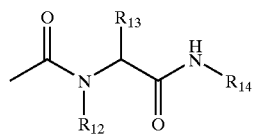

wherein $R_{12}$, $R_{13}$, and $R_{14}$ are independently hydrogen, $C_1-C_6$alkyl, aryl, aryl$C_1-C_6$alkyl and the alkyl and aryl groups are optionally substituted;

$R_4$ is hydrogen, hydroxy, $C_1-C_6$alkyl, aryl, aryl$C_1-C_6$alkyl, $NR_7R_8$, $C_1-C_6$alkyloxy; wherein the alkyl and aryl groups are optionally substituted;

$R_5$ is hydroxy, $C_1-C_6$alkyl, aryl, aryl$C_1-C_6$alkyl, $CF_3$, $NR_7R_8$; wherein the alkyl and aryl groups are optionally substituted;

$R_6$ is hydrogen, $C_1-C_6$alkyl, aryl, aryl$C_1-C_6$alkyl; wherein the alkyl and aryl groups are optionally substituted;

$R_7$ and $R_8$ are independently selected from hydrogen, $C_1-C_6$alkyl, aryl, aryl$C_1-C_6$alkyl, $C_1-C_6$alkyl-carbonyl, arylcarbonyl, aryl$C_1-C_6$alkyl-carbonyl, $C_1-C_6$alkyl-carboxy or aryl$C_1-C_6$alkylcarboxy wherein the alkyl and aryl groups are optionally substituted; or $R_7$ and $R_8$ are taken together with the nitrogen to which they are attached forming a cyclic or bicyclic system containing 3 to 11 carbon atoms and 0 to 2 additional heteroatoms selected from nitrogen, oxygen or sulfur, the ring system can optionally be substituted with at least one $C_1-C_6$alkyl, aryl, aryl$C_1-C_6$alkyl, hydroxy, $C_1-C_6$alkyloxy, aryl$C_1-C_6$alkyloxy, $C_1-C_6$alkyloxy$C_1-C_6$alkyl, $NR_9R_{10}$ or $C_1-C_6$alkylamino-$C_1-C_6$alkyl, wherein $R_9$ and $R_{10}$ are independently selected from hydrogen, $C_1-C_6$alkyl, aryl, aryl$C_1-C_6$alkyl, $C_1-C_6$alkylcarbonyl, arylcarbonyl, aryl$C_1-C_6$alkylcarbonyl, $C_1-C_6$alkyl-carboxy or aryl$C_1-C_6$alkylcarboxy; wherein the alkyl and aryl groups are optionally substituted; or $R_7$ and $R_8$ are independently a saturated or partial saturated cyclic 5, 6 or 7 membered amine or lactam;

Further, preferred compounds of the invention are compounds of formula Ia wherein $R_{16}$ and $R_{17}$ are hydrogen.

The invention will in its broadest aspect cover the following compounds: of Formula 1b:

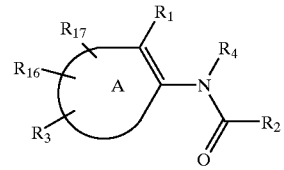

Formula 1b wherein

A is together with the double bond in Formula 1b is aryl;
$R_1$ is hydrogen, $COR_5$, $OR_6$, $CF_3$, nitro, cyano, $SO_3H$, $SO_2NR_7R_8$, $PO(OH)_2$, $CH_2PO(OH)_2$, $CHFPO(OH)_2$, $CF_2PO(OH)_2$, $C(=NH)NH_2$, $NR_7R_8$; or selected from the following 5-membered heterocycles:

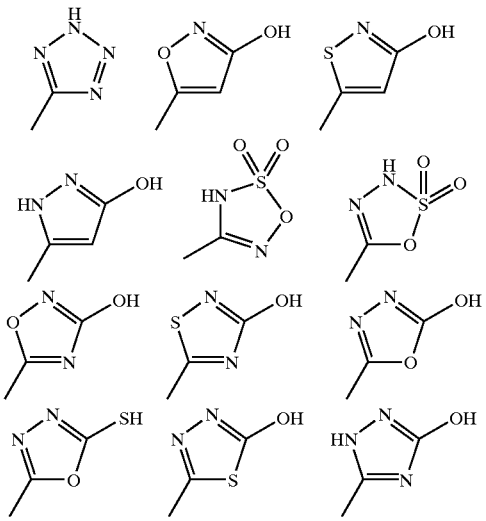

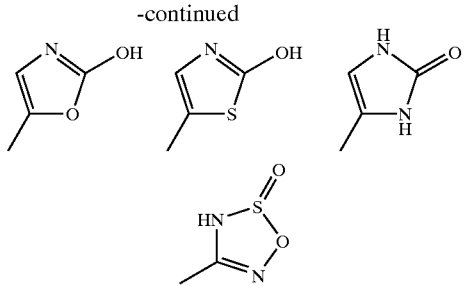

or $R_1$ is

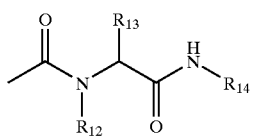

wherein $R_{12}$, $R_{13}$, and $R_{14}$ are independently hydrogen, $C_1$–$C_6$alkyl, aryl, aryl$C_1$–$C_6$alkyl and the alkyl and aryl groups are optionally substituted;

$R_2$ is $COR_5$, $OR_6$, $CF_3$, nitro, cyano, $SO_3H$, $SO_2NR_7R_8$, $PO(OH)_2$, $CH_2PO(OH)_2$, $CHFPO(OH)_2$, $CF_2PO(OH)_2$, $C(=NH)NH_2$, $NR_7R_8$; or selected from the following 5-membered heterocycles:

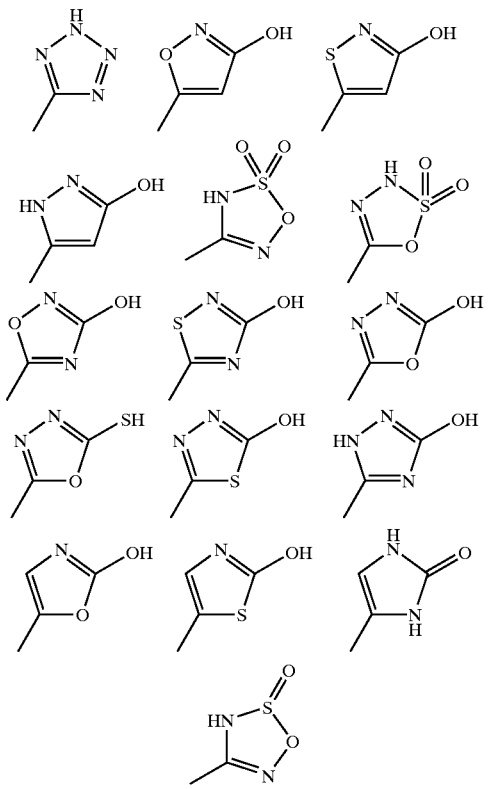

$R_3$, $R_{16}$ and $R_{17}$ are independently hydrogen, halo, nitro, cyano, trihalomethyl, $C_1$–$C_6$alkyl, aryl, aryl$C_1$–$C_6$-alkyl, hydroxy, oxo, carboxy, carboxy$C_1$–$C_6$alkyl, $C_1$–$C_6$alkyloxycarbonyl, aryloxycarbonyl, aryl$C_1$–$C_6$alkyloxycarbonyl, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$alkyl, thio, $C_1$–$C_6$alkylthio, $C_1$–$C_6$alkylthio$C_1$–$C_6$alkyl, arylthio, aryl$C_1$–$C_6$alkylthio, aryl$C_1$–$C_6$alkylthio$C_1$–$C_6$alkyl, $NR_7R_8$, $C_1$–$C_6$alkylamino$C_1$–$C_6$alkyl, aryl$C_1$–$C_6$alkylamino$C_1$–$C_6$alkyl, di(aryl$C_1$–$C_6$alkyl)amino$C_1$–$C_6$alkyl, $C_1$–$C_6$alkylcarbonyl, $C_1$–$C_6$alkylcarbonyl-$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkyl-carboxy, $C_1$–$C_6$alkylcarboxy$C_1$–$C_6$-alkyl, arylcarboxy, arylcarboxy$C_1$–$C_6$alkyl, aryl$C_1$–$C_6$alkylcarboxy, aryl$C_1$–$C_6$alkylcarboxy$C_1$–$C_6$alkyl, $C_1$–$C_6$alkylcarbonylamino, $C_1$–$C_6$alkylcarbonylamino$C_1$–$C_6$alkyl, -carbonyl$NR_7C_1$–$C_6$alkyl$COR_{11}$, aryl$C_1$–$C_6$alkylcarbonylamino, aryl$C_1$–$C_6$alkylcarbonylamino$C_1$–$C_6$alkyl, $CONR_7R_8$, or $C_1$–$C_6$alkyl$CONR_7R_8$ wherein the alkyl and aryl groups are optionally substituted and $R_{11}$ is $NR_7R_8$, or $C_1$–$C_6$alkyl$NR_7R_8$; or $R_3$ is

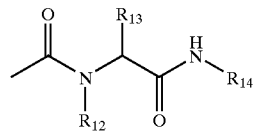

wherein $R_{12}$, $R_{13}$, and $R_{14}$ are independently hydrogen, $C_1$–$C_6$alkyl, aryl, aryl$C_1$–$C_6$alkyl and the alkyl and aryl groups are optionally substituted;

$R_4$ is hydrogen, hydroxy, $C_1$–$C_6$alkyl, aryl, aryl$C_1$–$C_6$alkyl, $NR_7R_8$, $C_1$–$C_6$alkyloxy; wherein the alkyl and aryl groups are optionally substituted;

$R_5$ is hydroxy, $C_1$–$C_6$alkyl, aryl, aryl$C_1$–$C_6$alkyl, $CF_3$, $NR_7R_8$; wherein the alkyl and aryl groups are optionally substituted;

$R_6$ is hydrogen, $C_1$–$C_6$alkyl, aryl, aryl$C_1$–$C_6$alkyl; wherein the alkyl and aryl groups are optionally substituted;

$R_7$ and $R_8$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkyl-carboxy or aryl$C_1$–$C_6$alkylcarboxy wherein the alkyl and aryl groups are optionally substituted; or $R_7$ and $R_8$ are together with the nitrogen to which they are attached forming a saturated, partially saturated or aromatic cyclic, bicyclic or tricyclic ring system containing from 3 to 14 carbon atoms and from 0 to 3 additional heteroatoms selected from nitrogen, oxygen or sulfur, the ring system can optionally be substituted with at least one $C_1$–$C_6$alkyl, aryl, aryl$C_1$–$C_6$alkyl, hydroxy, oxo, $C_1$–$C_6$alkyloxy, aryl$C_1$–$C_6$alkyloxy, $C_1$–$C_6$alkyloxy$C_1$–$C_6$alkyl, $NR_9R_{10}$ or $C_1$–$C_6$alkylamino$C_1$–$C_6$alkyl, wherein $R_9$ and $R_{10}$ independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy; wherein the alkyl and aryl groups are optionally substituted; or $R_7$ and $R_8$ are independently a saturated or partial saturated cyclic 5, 6 or 7 membered amine, imide or lactam;

or a salt thereof with a pharmaceutically acceptable acid or base, or any optical isomer or mixture of optical isomers, including a racemic mixture, or any tautomeric forms.

Particular preferred compounds of the invention are those compounds of formula I wherein $R_1$ is 5-tetrazolyl, i.e.

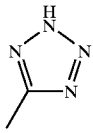

or $COR_5$ and $R_2$ is $COR_5$.

In particular, preferred compounds are those wherein $R_5$ is OH and $R_4$ is hydrogen.

The following compounds are preferred:
2-(Oxalyl-amino)-4,5,6,7tetrahydro-benzo[b]thiophene-3-carboxylic acid;
2-(Oxalyl-amino)-6-oxo-4,5,6,7tetrahydro-benzo[b]thiophene-3-carboxylic acid;
6-Benzoyl-2-(oxalyl-amino)-4,5,6,7-tetrahydro-thieno[2,3-c]pyidine-3-carboxylic acid;
6-Benzyl-2-(oxalyl-amino)-4,5,6,7-tetrahydro-thieno[2,3-c]pyridine-3-carboxylic acid;
6-Methyl-2-(oxalyl-amino)-4,5,6,7-tetrahydro-thieno[2,3-c]pyridine-3-carboxylic acid;
2-(Oxalyl-amino)-6-phenethyl-4,5,6,7-tetrahydro-thieno[2,3-c]pyridine-3-carboxylic acid;
5-Benzoyl-2-(oxalyl-amino)-4,5,6,7-tetrahydro-thieno[3,2-c]pyridine-3-carboxylic acid;
5-Benzyl-2-(oxalyl-amino)-4,5,6,7-tetrahydro-thieno[3,2-c]pyridine-3-carboxylic acid;
5-Methyl-2-(oxalyl-amino)-4,5,6,7-tetrahydro-thieno[3,2-c]pyridine-3-carboxylic acid;
2-(Oxalyl-amino)-5-phenethyl-4,5,6,7-tetrahydro-thieno[3,2-c]pyridine-3-carboxylic acid;
2-(Oxalyl-amino)-4,7-dihydro-5H-thieno[2,3-c]pyran-3-carboxylic acid;
2-(Oxalyl-amino)-4,5,6,7-tetrahydro-4,7-ethano-thieno[2,3-b]pyridine-3-carboxylic acid;
2-(Oxalyl-amino)-6-pyridin-2-ylmethyl-4,5,6,7-tetrahydro-thieno[2,3-c]pyridine-3-carboxylic acid;
2-(Oxalyl-amino)-4,5,6,7-tetrahydro-thieno[2,3-c]pyridine-3-carboxylic acid;
2-(Oxalyl-amino)-5-(((4-oxo-chromene-4H-2-carbonyl)amino)methyl)-4,7-dihydro-5H-thieno[2,3-c]pyran-3-carboxylic acid;
6-(3-Methoxy-benzyl)-2-(oxalyl-amino)-4,5,6,7-tetrahydro-thieno[2,3-c]pyridine-3-carboxylic acid;
6-(Oxalyl-amino)-1H-indole-7-carboxylic acid;
6-(Oxalyl-amino)-1H-indole-5-carboxylic acid;
1-(3-Methoxy-benzyl)-6-(oxalyl-amino)-1H-indole-5-carboxylic acid;
2-(Oxalyl-amino)-6-pyridin-3-ylmethyl-4,5,6,7-tetrahydro-thieno[2,3-c]pyridine-3-carboxylic acid;
2-(Oxalyl-amino)-6-pyridin-4-ylmethyl-4,5,6,7-tetrahydro-thieno[2,3-c]pyridine-3-carboxylic acid;
2-(Oxalyl-amino)-5-(2'-spiro[1',3']dioxolane)-6,7-dihydro-4H-benzo[b]thiophen-3-carboxylic acid;
3-[4-(3-Morpholin-4-yl-propionyl)-piperazin-1-ylmethyl]-6-(oxalyl-amino)-1H-indole-5-carboxylic acid;
2-(Oxalyl-amino)-6-quinolin-2-ylmethyl-4,5,6,7-tetrahydro-thieno[2,3-c]pyridine-3-carboxylic acid;
2-(Oxalyl-amino)-4,7-dihydro-5H-thieno[2,3-c]thiopyran-3-carboxylic acid;
2-(Oxalyl-amino)-6-oxo-4,7-dihydro-5H-thieno[2,3-c]thiopyran-3-carboxylic acid;
2-(Oxalyl-amino)-6,6-dioxo-4,7-dihydro-5H-thieno[2,3-c]thiopyran-3-carboxylic acid;
2-(Oxalyl-amino)-9H-thieno[2,3-c]chromen-3-carboxylic acid;
2-((2-H-Tetrazol-5-carbonyl)amino)-4,7-dihydro-5H-thieno[2,3-c]pyran-3-carboxylic acid;
N-(3-(2H-Tetrazol-5-yl)-4,7-dihydro-5H-thieno[2,3-c]pyran-2-yl)oxalamic acid;
2-(Oxalyl-amino)-4,5,6,7-tetrahydro-thieno[2,3-c]pyridine-3,6-dicarboxylic acid 6-benzyl ester;
2-(Oxalyl-amino)-4,5,6,7-tetrahydro-thieno[2,3-c]pyridine-3,6-dicarboxylic acid 6-ethyl ester;
6-Acetyl-2-(oxalyl-amino)-4,5,6,7-tetrahydro-thieno[2,3-c]pyridine-3-carboxylic acid;
2-(Oxalyl-amino)-6-phenylcarbamoylmethyl-4,5,6,7-tetrahydro-thieno(2,3-c]pyridine-3-carboxylic acid;
5-(1,3-Dioxo-1,3-dihydro-isoindol-2-ylmethyl)-2-(oxalyl-amino)-4,7-dihydro-5H-thieno[2,3-c]pyran-3-carboxylic acid;
5-(Benzoylamino-methyl)-2-(oxalyl-amino)-4,7-dihydro-5H-thieno[2,3-c]pyran-3-carboxylic acid;
5-Benzoyloxymethyl-2-(oxalyl-amino)-4,7-dihydro-5H-thieno[2,3-c]pyran-3-carboxylic acid;
2-(Oxalyl-amino)-5-(1-oxo-1,3-dihydro-isoindol-2-ylmethyl)-4,7-dihydro-5H-thieno[2,3-c]pyran-3-carboxylic acid;
1-(2-(4-Methyl-piperazin-1-yl)-2-oxo-ethyl)-6-(oxalyl-amino)-1H-indol-7-carboxylic acid;
N-(4-Carboxymethyl-4,5,6,7-tetrahydro-benzo[b]thiophen-2-yl)-oxalamic acid;
N-(4-Carboxymethylene-4,5,6,7-tetrahydro-benzo[b]thiophen-2-yl)-oxalamic acid;
N-(4-Carboxymethyl-4,7-dihydro-5H-thieno[2,3-c]pyran-2-yl)-oxalamic acid;
N-(4-Carboxymethylene-4,7-dihydro-5H-thieno[2,3-c]pyran-2-yl)-oxalamic acid;
N-(4-(2H-tetrazol-5-ylmethyl)-4,5,6,7-tetrahydro-benzo[b]thiophen-2-yl)-oxalamic acid;
N-(4-(2H-tetrazol-5-ylmethyl)-4,7-dihydro-5H-thieno[2,3-c]pyran-2-yl)-oxalamic acid;
2-(Oxalyl-amino)-5-((3-phenoxy-benzoylamino)-methyl)-4,7-dihydro-5H-thieno[2,3-c])pyran-3-carboxylic acid;
5-((3,5-Dimethoxy-benzoylamino)-methyl)-2-(oxalyl-amino)-4,7-dihydro-5H-thieno[2,3-c]pyran-3-carboxylic acid;
5-((3,5-Bis-trifluoromethyl-benzoylamino)-methyl)-2-(oxalyl-amino)-4,7-dihydro-5H-thieno[2,3-c]pyran-3-carboxylic acid;
5-((Cyclohexanecarbonyl-amino)-methyl)-2-(oxalyl-amino)-4,7-dihydro-5H-thieno[2,3-c]pyran-3-carboxylic acid;
5-((3-Dimethylamino-benzoylamino)-methyl)-2-(oxalyl-amino)-4,7-dihydro-5H-thieno[2,3-c]pyran-3-carboxylic acid;
5-((4-Acetylamino-benzoylamino)-methyl)-2-(oxalyl-amino)-4,7-dihydro-5H-thieno[2,3-c]pyran-3-carboxylic acid;
5-((2-Cyclopent-2-enyl-acetylamino)-methyl)-2-(oxalyl-amino)-4,7-dihydro-5H-thieno[2,3-c]pyran-3-carboxylic acid;
5-((2-Acetylamino-benzoylamino)-methyl)-2-(oxalyl-amino)-4,7-dihydro-5H-thieno[2,3-c]pyran-3-carboxylic acid;
5-((3-Methoxy-benzoylamino)-methyl)-2-(oxalyl-amino)-4,7-dihydro-5H-thieno[2,3-c]pyran-3-carboxylic acid;
5-((4-Dimethylamino-benzoylamino)-methyl)-2-(oxalyl-amino)-4,7-dihydro-5H-thieno[2,3-c]pyran-3-carboxylic acid;
2-(Oxalyl-amino)-5-((4-phenoxy-benzoylamino)-methyl)-4,7-dihydro-5H-thieno[2,3-c]pyran-3-carboxylic acid;
5-((4-Acetoxy-benzoylamino)-methyl)-2-(oxalyl-amino)-4,7-dihydro-5H-thieno[2,3-c]pyran-3-carboxylic acid;

5-(But-2-enoylamino-methyl)-2-(oxalyl-amino)-4,7-dihydro-5H-thieno[2,3-c]pyran-3-carboxylic acid;

2-(Oxalyl-amino)-5-((4-oxo-4-phenyl-butyrylamino)-methyl)-4,7-dihydro-5H-thieno[2,3-c]pyran-3-carboxylic acid;

2-(Oxalyl-amino)-5-((5-oxo-hexanoylamino)-methyl)-4,7-dihydro-5H-thieno[2,3-c]pyran-3-carboxylic acid;

4-Carboxymethyl-2-(oxalyl-amino)-4,5,6,7-tetrahydro-benzo-[b]thienophene-3-carboxylic acid;

2-(Oxalyl-amino)-5-((2-thiophen-2-yl-acetylamino)-methyl)-4,7-dihydro-5H-thieno[2,3-c]pyran-3-carboxylic acid;

5-(((1H-Indole-2-carbonyl)-amino)-methyl)-2-(oxalyl-amino)-4,7-dihydro-5H-thieno[2,3-c]pyran-3-carboxylic acid;

5-(((1H-Indole-3-carbonyl)-amino)-methyl)-2-(oxalyl-amino)-4,7-dihydro-5H-thieno[2,3-c]pyran-3-carboxylic acid;

5-(((1H-Indole-5-carbonyl)-amino)-methyl)-2-(oxalyl-amino)-4,7-dihydro-5H-thieno[2,3-c]pyran-3-carboxylic acid;

2-(Oxalyl-amino)-5-((3-pyridin-3-yl-acryloylamino)-methyl)-4,7-dihydro-5H-thieno[2,3-c]pyran-3-carboxylic acid;

2-(Oxalyl-amino)-5-((4-oxo-4-phenyl-but-2-enoylamino)-methyl)-4,7-dihydro-5H-thieno[2,3-c]pyran-3-carboxylic acid;

5-((2-(4-Benzyloxy-phenoxy)-acetylamino)-methyl)-2-(oxalyl-amino)-4,7-dihydro-5H-thieno[2,3-c]pyran-3-carboxylic acid;

2-(Oxalyl-amino)-5-(((4-oxo-4H-chromene-3-carbonyl)-amino)-methyl)-4,7-dihydro-5H-thieno[2,3-c]pyran-3-carboxylic acid;

5-(((5-Benzyloxy-1H-indole-2-carbonyl)-amino)-methyl)-2-(oxalyl-amino)-4,7-dihydro-5H-thieno[2,3-c]pyran-3-carboxylic acid;

2-(Oxalyl-amino)-5-((3-thiophen-2-yl-acryloylamino)-methyl)-4,7-dihydro-5H-thieno[2,3-c]pyran-3-carboxylic acid;

2-(Oxalyl-amino)-5-(((4-oxo-chromene-4H-3-carbonyl) amino)methyl)-4,7-dihydro-5H-thieno[2,3-c]pyran-3-carboxylic acid;

2-(Oxalyl-amino)-5-((3-phenyl-propionylamino)-methyl)-4,7-dihydro-5H-thieno[2,3-c]pyran-3-carboxylic acid;

5-(((Furan-2-carbonyl)-amino)-methyl)-2-(oxalyl-amino)-4,7-dihydro-5H-thieno[2,3-c]pyran-3-carboxylic acid;

5-(((Naphthalene-2-carbonyl)-amino)-methyl)-2-(oxalyl-amino)-4,7-dihydro-5H-thieno[2,3-c]pyran-3-carboxylic acid;

2-(Oxalyl-amino)-5-((2-phenoxy-acetylamino)-methyl)-4,7-dihydro-5H-thieno[2,3-c]pyran-3-carboxylic acid;

2-(Oxalyl-amino)-5-(phenylacetylamino-methyl)-4,7-dihydro-5H-thieno[2,3-c]pyran-3-carboxylic acid;

5-((2-(3,4-Dimethoxy-phenyl)-acetylamino)-methyl)-2-(oxalyl-amino)-4,7-dihydro-5H-thieno[2,3-c]pyran-3-carboxylic acid;

5-((2-(4-Ethoxy-phenyl)-acetylamino)-methyl)-2-(oxalyl-amino)-4,7-dihydro-5H-thieno[2,3-c]pyran-3-carboxylic acid;

2-(Oxalyl-amino)-5-((3-phenyl-acryloylamino)-methyl)-4,7-dihydro-5H-thieno[2,3-]pyran-3-carboxylic acid;

5-((3-(3,5-Dimethoxy-phenyl)-acryloylamino)-methyl)-2-(oxalyl-amino)-4,7-dihydro-5H-thieno[2,3-c]pyran-3-carboxylic acid;

2-(Oxalyl-amino)-5-(((5-oxo-pyrrolidine-2-carbonyl)-amino)-methyl)-4,7-dihydro-5H-thieno[2,3-c]pyran-3-carboxylic acid;

5-(((Furan-3-carbonyl)-amino)-methyl)-2-(oxalyl-amino)-4,7-dihydro-5H-thieno[2,3-c]pyran-3-carboxylic acid;

2-(Oxalyl-amino)-5-(((thiophene-2-carbonyl)-amino)-methyl)-4,7-dihydro-5H-thieno[2,3-c]pyran-3-carboxylic acid;

5-((2-(1,3-Dioxo-1,3-dihydro-isoindol-2-yl)-acetylamino)-methyl)-2-(oxalyl-amino)-4,7-dihydro-5H-thieno[2,3-c]pyran-3-carboxylic acid;

2-(Oxalyl-amino)-5-(((pyrazine-2-carbonyl)-amino)-methyl)-4,7-dihydro-5H-thieno[2,3-c]pyran-3-carboxylic acid;

2-(Oxalyl-amino)-5-(((1-oxy-pyridine-2-carbonyl)-amino)-methyl)-4,7-dihydro-5H-thieno[2,3-c]pyran-3-carboxylic acid;

2-(Oxalyl-amino)-5-(((pyridine-2-carbonyl)-amino)-methyl)-4,7-dihydro-5H-thieno[2,3-c]pyran-3-carboxylic acid;

2-(Oxalyl-amino)-5-(((pyridine-3-carbonyl)-amino)-methyl)-4,7-dihydro-5H-thieno[2,3-c]pyran-3-carboxylic acid;

5-((2-(3,5-Bis-trifluoromethyl-phenyl)-acetylamino)-methyl)-2-(oxalyl-amino)-4,7-dihydro-5H-thieno[2,3-c]pyran-3-carboxylic acid;

5-((3-Benzenesulfonyl-propionylamino)-methyl)-2-(oxalyl-amino)-4,7-dihydro-5H-thieno[2,3-c]pyran-3-carboxylic acid;

5-((3-(3,5-Difluoro-phenyl)-acryloylamino)-methyl)-2-(oxalyl-amino)-4,7-dihydro-5H-thieno[2,3-c]pyran-3-carboxylic acid;

2-(Oxalyl-amino)-5-((4-oxo-pent-2-enoylamino)-methyl)-4,7-dihydro-5H-thieno[2,3-c]pyran-3-carboxylic acid;

5-((3-(1,3-Dioxo-1,3-dihydro-isoindol-2-yl)-propionylamino)-methyl)-2-(oxalyl-amino)-4,7-dihydro-5H-thieno[2,3-c]pyran-3-carboxylic acid;

2-(Oxalyl-amino)-5-((6-oxo-heptanoylamino)-methyl)-4,7-dihydro-5H-thieno[2,3-c]pyran-3-carboxylic acid;

5-((2-(4-Dimethylamino-phenyl)-acetylamino)-methyl)-2-(oxalyl-amino)-4,7-dihydro-5H-thieno[2,3-c]pyran-3-carboxylic acid;

5-(((Benzo(1,3)dioxole-5-carbonyl)-amino)-methyl)-2-(oxalyl-amino)-4,7-dihydro-5H-thieno[2,3-c]pyran-3-carboxylic acid;

5-((2-Acetylamino-3-phenyl-propionylamino)-methyl)-2-(oxalyl-amino)-4,7-dihydro-5H-thieno[2,3-c]pyran-3-carboxylic acid;

5-((2-Acetoxy-benzoylamino)-methyl)-2-(oxalyl-amino)-4,7-dihydro-5H-thieno[2,3c]pyran-3-carboxylic acid;

2-(Oxalyl-amino)-5-((2-oxo-3-phenyl-propionylamino)-methyl)-4,7-dihydro-5H-thieno[2,3-c]pyran-3-carboxylic acid;

5-((2-Benzoylamino-acetylamino)-methyl)-2-(oxalyl-amino)-4,7-dihydro-5H-thieno[2,3-c]pyran-3-carboxylic acid;

2-(Oxalyl-amino)-5-((4-oxo-pentanoylamino)-methyl)-4,7-dihydro-5H-thieno[2,3-c]pyran-3-carboxylic acid;

5-((3-Furan-2-yl-acryloylamino)-methyl)-2-(oxalyl-amino)-4,7-dihydro-5H-thieno[2,3-c]pyran-3-carboxylic acid;

5-((2-Acetylamino-acetylamino)-methyl)-2-(oxalyl-amino)-4,7-dihydro-5H-thieno[2,3c]pyran-3-carboxylic acid;

2-(Oxalyl-amino)-5-((2-phenylsulfanyl-acetylamino)-methyl)-4,7-dihydro-5H-thieno[2,3-c]pyran-3-carboxylic acid;

5-((2-Benzylsulfanyl-acetylamino)-methyl)-2-(oxalyl-amino)-4,7-dihydro-5H-thieno[2,3-c]pyran-3-carboxylic acid;

5-((2-(1H-Indol-3-yl)-2-oxo-acetylamino)-methyl)-2-(oxalyl-amino)-4,7-dihydro-5H-thieno[2,3-c]pyran-3-carboxylic acid;

5-((3-(1H-indol-3-yl)-2-oxo-propionylamino)-methyl)-2-(oxalyl-amino)-4,7-dihydro-5H-thieno[2,3-c]pyran-3-carboxylic acid;

5-((3-(2-Nitro-phenyl)-2-oxo-propionylamino)-methyl)-2-(oxalyl-amino)-4,7-dihydro-5H-thieno[2,3-c]pyran-3-carboxylic acid;

5-((2-Acetylamino-3-phenyl-acryloylamino)-methyl)-2-(oxalyl-amino)-4,7-dihydro-5H-thieno[2,3-c]pyran-3-carboxylic acid;

5-(((1-Acetyl-pyrrolidine-2-carbonyl)-amino)-methyl)-2-(oxalyl-amino)-4,7-dihydro-5H-thieno[2,3-c]pyran-3-carboxylic acid;

5-((2-(1,3-Dioxo-1,3-dihydro-isoindol-2-yl)-3-(1H-imidazol-4-yl)-propionylamino)-methyl)-2-(oxalyl-amino)-4,7-dihydro-5H-thieno[2,3-c]pyran-3-carboxylic acid;

5-((4-(3,4-Dimethoxy-phenyl)-2-oxo-but-3-enoylamino)-methyl)-2-(oxalyl-amino)-4,7-dihydro-5H-thieno[2,3-c]pyran-3-carboxylic acid;

5-((3-1H-Benzoimidazol-2-yl-propionylamino)-methyl)-2-(oxalyl-amino)-4,7-dihydro-5H-thieno[2,3-c]pyran-3-carboxylic acid;

5-((2-(1,3-Dioxo-1,3-dihydro-isoindol-2-yl)-butyrylamino)-methyl)-2-(oxalyl-amino)-4,7-dihydro-5H-thieno[2,3-c]pyran-3-carboxylic acid;

5-((2-Acetylamino-propionylamino)-methyl)-2-(oxalyl-amino)-4,7-dihydro-5H-thieno[2,3-c]pyran-3-carboxylic acid;

5-((2-Acetylamino-4-methylsulfanyl-butyrylamino)-methyl)-2-(oxalyl-amino)-4,7-dihydro-5H-thieno[2,3-c]pyran-3-carboxylic acid;

5-((2-(1,3-Dioxo-1,3-dihydro-isoindol-2-yl)-4-methyl-pentanoylamino)-methyl)-2-(oxalyl-amino)-4,7-dihydro-5H-thieno[2,3-c]pyran-3-carboxylic acid;

5-((2-Acetylamino-3-methyl-butyrylamino)-methyl)-2-(oxalyl-amino)-4,7dihydro-5H-thieno[2,3-c]pyran-3-carboxylic acid;

5-((2-(1,3-Dioxo-1,3-dihydro-isoindol-2-yl)-3-phenyl-propionylamino)-methyl)-2-(oxalyl-amino)-4,7-dihydro-5H-thieno[2,3-c]pyran-3-carboxylic acid;

5-((3-Furan-3-yl-acryloylamino)-methyl)-2-(oxalyl-amino)-4,7-dihydro-5H-thieno[2,3-c]pyran-3-carboxylic acid;

5-((2-indan-2-yl-acetylamino)-methyl)-2-(oxalyl-amino)-4,7-dihydro-5H-thieno[2,3-c]pyran-3-carboxylic acid;

5-(((9,10-Dioxo-9,10-dihydro-anthracene-2-carbonyl)-amino)-methyl)-2-(oxalyl-amino)-4,7-dihydro-5H-thieno[2,3-c]pyran-3-carboxylic acid;

5-((2-(Naphthalen-1-yloxy)-acetylamino)-methyl)-2-(oxalyl-amino)-4,7-dihydro-5H-thieno[2,3-c]pyran-3-carboxylic acid;

2-(Oxalyl-amino)-5-(((4-oxo-4H-chromene-2-carbonyl)-amino)-methyl)-4,7-dihydro-5H-thieno[2,3-c]pyran-3-carboxylic acid;

2-(Oxalyl-amino)-5-(((3-oxo-indane-1-carbonyl)-amino)-methyl)-4,7-dihydro-5H-thieno[2,3-c]pyran-3-carboxylic acid;

5-((2-(1,3-Dioxo-1,3-dihydro-isoindol-2-yl)-propionylamino)-methyl)-2-(oxalyl-amino)-4,7-dihydro-5H-thieno[2,3-c]pyran-3-carboxylic acid;

7-(1,3-Dioxo-1,3-dihydro-isoindol-2-ylmethyl)-2-(oxalyl-amino)-4,7-dihydro-5H-thieno[2,3-c]pyran-3-carboxylic acid;

7-(Acetylamino-methyl)-2-(oxalyl-amino)-4,7-dihydro-5H-thieno[2,3-c]pyran-3-carboxylic acid;

2-(Oxalyl-amino)-5-(((3-oxo-indane-1-carbonyl)amino)methyl)-4,7-dihydro-5H-thieno[2,3-c]pyran-3-carboxylic acid;

5-(2,4-Dioxo-thiazolidin-3-ylmethyl)-2-(oxalyl-amino)-4,7-dihydro-5H-thieno[2,3-c]pyran-3-carboxylic acid;

5-(5,6-Dichloro-1,3-dioxo-1,3-dihydro-isoindol-2-ylmethyl)-2-(oxalyl-amino)-4,7-dihydro-5H-thieno[2,3-c]pyran-3-carboxylic acid;

5-(1,3-Dioxo-1,3,4,5,6,7-hexahydro-isoindol-2-ylmethyl)-2-(oxalyl-amino)-4,7-dihydro-5H-thieno[2,3-c]pyran-3-carboxylic acid;

2-(Oxalyl-amino)-5-(1,1,3-trioxo-1,3-dihydro-1H-benzo[d]isothiazol-2-ylmethyl)-4,7-dihydro-5H-thieno[2,3-c]pyran-3-carboxylic acid;

5-[(4-Methoxy-benzenesulfonylamino)-methyl]-2-(oxalyl-amino)-4,7-dihydro-5H-thieno[2,3-c]pyran-3-carboxylic acid;

N-(6-Hydroxy-3-hydroxymethyl-4,5,6,7-tetrahydro-benzo[b]thiophen-2-yl)-oxalamic acid;

2-(Oxalyl-amino)-6-(2'-spiro[1',3']dioxolane)-6,7-dihydro-4H-benzo[b]thiophen-3-carboxylic acid;

5-(2-Methyl-4-oxo-4H-quinazolin-3-ylmethyl)-2-(oxalyl-amino)-4,7-dihydro-5H-thieno[2,3-c]pyran-3-carboxylic acid;

5-(5-Chloro-1,3-dioxo-6-sulfamoyl-1,3-dihydro-isoindol-2-ylmethyl)-2-(oxalyl-amino)-4,7-dihydro-5H-thieno[2,3-c]pyran-3-carboxylic acid;

5-(5,7-Dioxo-5,7-dihydro-pyrrolo[3,4-b]pyridin-6-ylmethyl)-2-(oxalyl-amino)-4,7-dihydro-5H-thieno[2,3-c]pyran-3-carboxylic acid;

5-(1,3-Dioxo-1,3-dihydro-pyrrolo[3,4-c]pyridin-2-ylmethyl)-2-(oxalyl-amino)-4,7-dihydro-5H-thieno[2,3-c]pyran-3-carboxylic acid;

5-(5,7-Dioxo-5,7-dihydro-pyrrolo[3,4-b]pyrazin-6-ylmethyl)-2-(oxalyl-amino)-4,7-dihydro-5H-thieno[2,3-c]pyran-3-carboxylic acid;

5-(5-Nitro-1,3-dioxo-1,3-dihydro-isoindol-2-ylmethyl)-2-(oxalyl-amino)-4,7-dihydro-5H-thieno[2,3-c]pyran-3-carboxylic acid;

5-(1,3-Dioxo-3,4-dihydro-1H-isoquinolin-2-ylmethyl)-2-(oxalyl-amino)-4,7-dihydro-5H-thieno[2,3-c]pyran-3-carboxylic acid;

5-(4,6-Dioxo-4,6-dihydro-thieno[2,3-c]pyrrol-5-ylmethyl)-2-(oxalyl-amino)-4,7-dihydro-5H-thieno[2,3-c]pyran-3-carboxylic acid;

5-(4,6-Dioxo-4H,6H-thieno[3,4-c]pyrrol-5-ylmethyl)-2-(oxalyl-amino)-4,7-dihydro-5H-thieno[2,3-c]pyran-3-carboxylic acid;

5-(4,6-Dioxo-2,6-dihydro-4H-pyrrolo[3,4-c]pyrazol-5-ylmethyl)-2-(oxalyl-amino)-4,7-dihydro-5H-thieno[2,3-c]pyran-3-carboxylic acid;

5-(4,6-Dioxo-4,6-dihydro-pyrrolo[3,4-d]thiazol-5-ylmethyl)-2-(oxalyl-amino)-4,7-dihydro-5H-thieno[2,3-c]pyran-3-carboxylic acid;

5-(2-Acetylamino-4,6-dioxo-4,6-dihydro-pyrrolo[3,4-d]thiazol-5-ylmethyl)-2-(oxalyl-amino)-4,7-dihydro-5H-thieno[2,3-c]pyran-3-carboxylic acid;

5-(5-Hydroxy-1,3-dioxo-1,3-dihydro-isoindol-2-ylmethyl)-2-(oxalyl-amino)-4,7-dihydro-5H-thieno[2,3-c]pyran-3-carboxylic acid;

5-(5-Methoxy-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Hydroxy-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Methoxy-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Nitro-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Acetyl-2,6-dioxo-piperazin-1-ylmethyl)-2-(oxalyl-amino)-4,7-dihydro-5H-thieno[2,3-c]pyran-3-carboxylic acid;
5-(2,6-Dioxo-4-trifluoromethanesulfonyl-piperazin-1-ylmethyl)-2-(oxalyl-amino)-4,7-dihydro-5H-thieno[2,3-c]pyran-3-carboxylic acid;
5-(4-Methanesulfonyl-2,6-dioxo-piperazin-1-ylmethyl)-2-(oxalyl-amino)-4,7-dihydro-5H-thieno[2,3-c]pyran-3-carboxylic acid;
5-(5-Methylcarbamoyl-1,3-dioxo-1,3-dihydro-isoindol-2-ylmethyl)-2-(oxalyl-amino)-4,7-dihydro-5H-thieno[2,3-c]pyran-3-carboxylic acid;
5-(5-Ethylcarbamoyl-1,3-dioxo-1,3-dihydro-isoindol-2-ylmethyl)-2-(oxalyl-amino)-4,7-dihydro-5H-thieno[2,3-c]pyran-3-carboxylic acid;
5-(5-Propylcarbamoyl-1,3-dioxo-1,3-dihydro-isoindol-2-ylmethyl)-2-(oxalyl-amino)-4,7-dihydro-5H-thieno[2,3-c]pyran-3-carboxylic acid;
2-(Oxalyl-amino)-5-(1-thioxo-1,3-dihydro-isoindol-2-yl methyl)-4,7-dihydro-5H-thieno[2,3-c]pyran-3-carboxylic acid;
5-(4-Dimethylcarbamoyl-2,6-dioxo-piperazin-1-ylmethyl)-2-(oxalyl-amino)-4,7-dihydro-5H-thieno[2,3-c]pyran-3-carboxylic acid;
5-(4-Methylcarbamoyl-2,6-dioxo-piperazin-1-ylmethyl)-2-(oxalyl-amino)-4,7-dihydro-5H-thieno[2,3-c]pyran-3-carboxylic acid;
5-(2,6-Dioxo-piperazin-1-ylmethyl)-2-(oxalyl-amino)-4,7-dihydro-5H-thieno[2,3-c]pyran-3-carboxylic acid;
5-(4-Carbamoylmethyl-2,6-dioxo-piperazin-1-ylmethyl)-2-(oxalyl-amino)-4,7-dihydro-5H-thieno[2,3-c]pyran-3-carboxylic acid;
5-(4-Carboxymethyl-2,6-dioxo-piperazin-1-ylmethyl)-2-(oxalyl-amino)-4,7-dihydro-5H-thieno[2,3-c]pyran-3-carboxylic acid;
5-(3,5-Dioxo-2,3-dihydro-5H-benzo[f][1,4]oxazepin-4-ylmethyl)-2-(oxalyl-amino)-4,7-dihydro-5H-thieno[2,3-c]pyran-3-carboxylic acid;
5-(2-Acetylamino-5,7-dioxo-5,7-dihydro-pyrrolo[3,4-d]pyrimidin-6-ylmethyl)-2-(oxalyl-amino)-4,7-dihydro-5H-thieno[2,3-c]pyran-3-carboxylic acid;
5-(4-(4-Acetylamino-benzenesulfonyl)-2,6-dioxo-piperazin-1-ylmethyl)-2-(oxalyl-amino)-4,7-dihydro-5H-thieno[2,3-c]pyran-3-carboxylic acid;
5-(4-(Methoxy-methyl-carbamoyl)-2,6-dioxo-piperidin-1-ylmethyl)-2-(oxalyl-amino)-4,7-dihydro-5H-thieno[2,3-c]pyran-3-carboxylic acid;

PHARMACOLOGICAL METHODS

The compounds are evaluated for biological activity with a truncated form of PTP1B (corresponding to the first 321 amino acids), which was expressed in *E. coli* and purified to apparent homogeneity using published procedures well-known to those skilled in the art. The enzyme reactions are carried out using standard conditions essentially as described by Burke et al. (*Biochemistry* 35; 15989–15996 (1996)). The assay conditions are as follows. Appropriate concentrations of the compounds of the invention are added to the reaction mixtures containing different concentrations of the substrate, p-nitrophenyl phosphate (range: 0.16 to 10 mM—final assay concentration). The buffer used was 100 mM sodium acetate pH 5.5, 50 mM sodium chloride, 0.1% (w/v) bovine serum albumin and 5 mM dithiothreitol (total volume 100 ml). The reaction was started by addition of the enzyme and carried out in microtiter plates at 25° C. for 60 minutes. The reactions are stopped by addition of NaOH. The enzyme activity was determined by measurement of the absorbance at 405 nm with appropriate corrections for absorbance at 405 nm of the compounds and p-nitrophenyl phosphate. The data are analyzed using nonlinear regression fit to classical Michaelis Menten enzyme kinetic models. Inhibition is expressed as $K_i$ values in $\mu M$. The results of representative experiments are shown in Table 1

TABLE 1

Inhibition of classical PTP1B by compounds of the invention

| Example no. | PTP1B $K_i$ values ($\mu M$) |
|---|---|
| 1 | 51 |
| 2 | 37 |
| 6 | 3 |

Further, the compounds are evaluated for biological activity as regards their effect as inhibitors of PTPα in essentially the same way as described for inhibition of PTP1B. Derived from their activity as evaluated above the compounds of the invention may be useful in the treatment of diseases selected from the group consisting of type I diabetes, type II diabetes, impaired glucose tolerance, insulin resistance and obesity. Furthermore, derived from their activity as evaluated above, the compounds of the invention may be useful in the treatment of diseases selected from the group consisting of immune dysfunctions including autoimmunity, diseases with dysfunctions of the coagulation system, allergic diseases including asthma, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimer's disease and schizophrenia, and infectious diseases.

THE SYNTHESIS OF THE COMPOUNDS

In accordance with one aspect of the invention, the compounds of the invention are prepared as illustrated in the following reaction scheme:

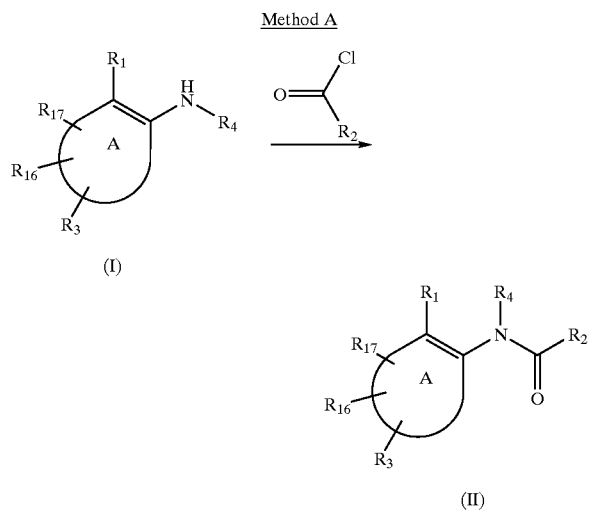

By allowing an amino substituted aryl or heteroaryl (I) to react with an acid chloride of formula (II), wherein A, $R_1$, $R_2$, $R_3$, $R_4$, $R_{16}$ and $R_{17}$ are defined as above.

Method B $R_{15}COOH + R_{12}NH_2 + R_{13}CHO + R_{14}NC \longrightarrow$ (I) (II) (III) (IV)

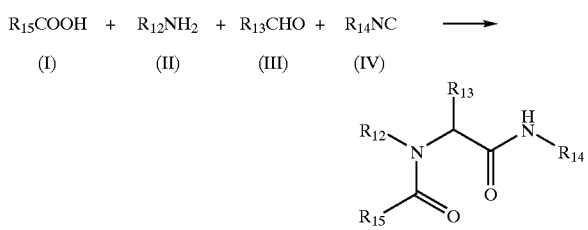

By allowing a carboxylic acid (I), a primary amine (II) and an aldehyde (III) to react with a isocyanide (IV) wherein $R_{12}$, $R_{13}$, $R_{14}$, and $R_{15}$ are independently selected from the group consisting of hydrogen, $C_1$–$C_6$alkyl, aryl, aryl$C_1$–$C_6$alkyl as defined above and the alkyl and aryl groups are optionally substituted as defined above; or $R_{12}$, $R_{13}$, $R_{14}$, and $R_{15}$ are independently selected from

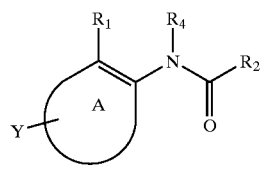

wherein Y indicates attachment point for $R_{12}$, $R_{13}$, $R_{14}$, and $R_{15}$ and A, $R_1$ $R_2$ and $R_4$ are defined as above.

In a preferred method, the above described four component Ugi reaction can be carried out by attaching any one of the components to a solid support. Hence, the synthesis can be accomplished in a combinatorial chemistry fashion.

Method C

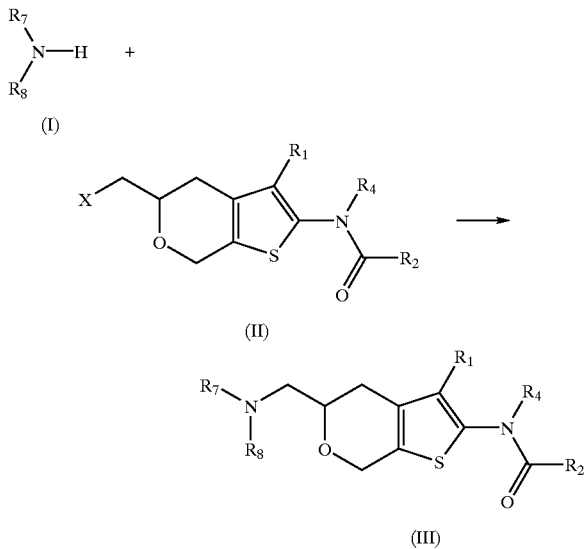

By allowing an amine (I) and a substituted 4,5-dihydro-7H-thieno[2,3-c]pyran (II) to react under basic conditions (e.g. $K_2CO_3$, in N,N-dimethylformamide or methylethylketone) or under Mitsunobu conditions (Oyo Mitsunobu, *Synthesis*, (1981) 1–28) to yield (III) wherein X is OH, $OSO_2Me$ or halo, and $R_1$, $R_2$, $R_4$, $R_7$ and $R_8$ are defined above.

General procedure for the Preparation of Acetoxymethyl Esters (C. Schultz et al., The Journal of Biological Chemistry, 1993, 268, 6316–6322.): A carboxylic acid (1 equivalent) was suspended in dry acetonitrile (2 ml per 0.1 mmol). Diisopropyl amine (3.0 equivalents) was added followed by bromomethyl acetate (1.5 equivalents). The mixture was stirred under nitrogen overnight at room temperature. Acetonitrile was removed under reduced pressure to yield an oil which was diluted in ethylacetate and washed water (3×). The organic layer was dried over anhydrous magnesium sulfate. Filtration followed by solvent removal under reduced pressure afforded a crude oil. The product was purified by column chromatography on silica gel, using an appropriate solvent system.

The present invention also has the objective of providing suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouning agents, colouring agents and preserving agents in order to produce pharmaceutically elegant and palatable preparations. The tablets contain the acting ingredient in admixture with non-toxic pharmaceutically acceptable excipients which are suitable for the manufacture of tablets. These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,4,52; and 4,265,874 to form osmotic therapeutic tablets for control release.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such expicients may be (1) suspending agent such as sodium carboxymethyl cellulose, methyl cellulose, hydroxypropylmethyl-cellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The Compounds of the invention may also be administered in the form of suppositories for rectal administration. These compositions can be prepared by mixing the drug with a suitable non-irritating excipient which is solid at ordinary temperature but liquid at the rectal temperature and will therefore melt in the rectum to release the drug. Such materials are cocoa butter and polyethylene glycols.

The compounds of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidyl-cholines.

For topical use, creams, ointments, jellies, solutions or suspensions, etc., containing the compounds of Formula 1 are employed.

Dosage levels of the compounds of the present invention are of the order of about 0.5 mg to about 100 mg per kilogram body weight, with a preferred dosage range between about 20 mg to about 50 mg per kilogram body weight per day (from about 25 mg to about 5 g's per patient per day). The amount of active ingredient that may be combined with the carrier materials to produce a single dosage will vary depending upon the host treated and the particular mode of administration. For example, a formulation intended for oral administration to humans may contain 5 mg to 1 g of an active compound with an appropriate and convenient amount of carrier material which may vary from about 5 to about 95 percent of the total composition. Dosage unit forms will generally contain between from about 5 mg to about 500 mg of active ingredient.

It will be understood, however, that the specific dose level for any particular patient will depend upon a variety of factors including the activity of the specific compound employed, the age, body weight, general health, gender, diet, time of administration, route of administration, rate of excretion, drug combination and the severity of the particular disease undergoing therapy. The dosage needs to be individualized by the clinician.

EXAMPLES

The process for preparing compounds of Formula 1 and preparations containing them is further illustrated in the following examples, which, however, are not to be construed as limiting.

Hereinafter, TLC is thin layer chromatography, $CDCl_3$ is deuterio chloroform, $CD_3OD$ is tetradeuterio methanol and DMSO-$d_6$ is hexadeuterio dimethylsulfoxide. The structures of the compounds are confirmed by either elemental analysis or NMR, where peaks assigned to characteristic protons in the title compounds are presented where appropriate. $^1H$ NMR shifts ($\delta_H$) are given in parts per million (ppm) down field from tetramethylsilane as internal reference standard.

M.p.: is melting point and is given in ° C. and is not corrected. Column chromatography was carried out using the technique described by W. C. Still et al., *J. Org. Chem.* 43: 2923 (1978) on Merck silica gel 60 (Art. 9385). HPLC analyses are performed using 5 µm C18 4×250 mm column eluted with various mixtures of water and acetonitrile, flow=1 ml/min, as described in the experimental section.

Wang-resin is polystyrene with a 4-hydroxymethylphenol ether linker. Compounds used as starting material are either known compounds or compounds which can readily be prepared by methods known per se.

Example 1

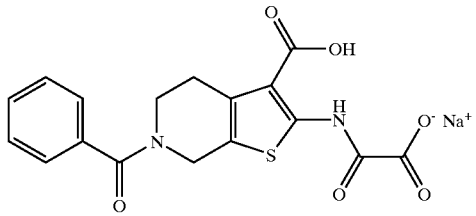

6-Benzoyl-2-(oxalyl-amino)-4,5,6,7-tetrahydro-thieno[2,3-c]pyridine-3-carboxylic Acid, Mono Sodium Salt A mixture of N-benzoyl-4-piperidone (20.0 g, 0.1 mol), ethyl cyanoacetate (10.9 ml, 0.1 mol), ammonium acetate (2.0 g) and acetic acid (6 ml) in benzene (100 ml) was heated at reflux temperature in a 3-nacked reaction flask equipped with a Dean-Stark water trap for 1 h. The cooled reaction mixture was diluted with ethyl acetate (100 ml) washed with water (3×100 ml), saturated aqueous sodium chloride (80 ml), dried ($MgSO_4$) filtered and evaporated in vacuo affording quantitative yield of (1-benzoyl-piperidin-4-ylidene)-cyano-acetic acid ethyl ester as a slowly crystallising oil.

A mixture of the above benzoyl-piperidin-4-ylidene (10.0 g, 0.034 mol), sulphur (1.13 g, 0.035 mol) and morpholin (6.5 ml) in ethanol (35 ml) was heated at 50° C. for 2 h and stirred at room temperature over night. The precipitate was filtered off and washed with 96% ethanol (3×50 ml), diethyl ether (3×50 ml) and dried in vacuo which afforded 9.27 g (84%) of 2-amino-6-benzoyl-4,5,6,7-tetrahydro-thieno[2,3-c]pyridine-3-carboxylic acid ethyl ester as a solid.

To a stirred solution of the above 4,5,6,7-tetrahydro-thieno[2,3-c]pyridine-3-carboxylic acid ethyl ester (5.0 g, 0.015 mol), triethylamine (4.21 ml, 0.03 mol) in dry tetrahydrofuran (30 ml) at 0° C. was added dropwise a solution of ethyl oxalyl chloride (1.9 ml, 0.017 mol) in dry tetrahydrofuran (20 ml). The resulting reaction mixture was stirred at room temperature for 18 h, poured into ice water (300 ml) and extracted with ethyl acetate (3×100 ml). The combined organic extracts were washed with saturated aqueous sodium chloride (100 ml), dried ($MgSO_4$) filtered and evaporated in vacuo affording 4.2 g (84%) of 6-benzoyl-2-(ethoxyoxalyl-amino)-4,5,6,7-tetrahydro-thieno[2,3-c] pyridine-3-carboxylic acid ethyl ester as a crystallising oil.

To a solution of the above thieno[2,3-c]pyridine-3-carboxylic acid ethyl ester (4.2 g, 9.76 mmol) in ethanol (100 ml) was added a solution of sodium hydroxide (0.9 g, 21.46 mmol) in water (100 ml). The resulting reaction mixture was stirred at room temperature for 18 h. The volatiles were evaporated in vacuo and the residue dissolved in water (100 ml) and washed with ethyl acetate (2×100 ml). To the aqueous phase was added concentrated hydrochloric acid to pH=1 and the precipitate was filtered off and washed with water (2×50 ml), diethyl ether (2×30 ml) and dried in vacuo at 50° C. affording 2.9 g (79%) of the title compound as a solid.

M.p.: Amorph: Calculated for $C_{17}H_{13}N_2O_6S_1Na_1$, 1×$H_2O$; C, 49.28%; H, 3.65%; N, 6.76%. Found: C, 49.31%; H, 3.86%; N, 6.53%.

By a similar procedure as described in Example 1 the following compounds have been prepared.

Example 2

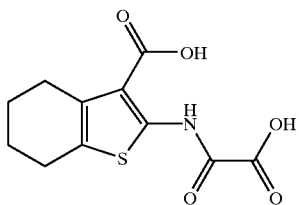

2-(Oxalyl-amino)-4,5,6,7-tetrahydro-benzo[b]thiophene-3-carboxylic Acid

M.p.: 230–231° C.; Calculated for $C_{11}H_{11}NO_5S$; C, 49.07%; H, 4.12%; N, 5.20%. Found: C, 49.87%; H, 4.37%; N, 5.06%.

Example 3

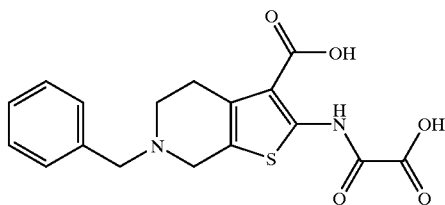

6-Benzyl-2-(oxalyl-amino)-4,5,6,7-tetrahydro-thieno[2,3-c]pyridine-3-carboxylic Acid Calculated for $C_{17}H_{16}N_2O_5S$, 1.75 $H_2O$; C, 52.10%; H, 5.01%; N, 7.15%. Found: C, 52.11%; H, 4.81%; N, 7.01%.

Example 4

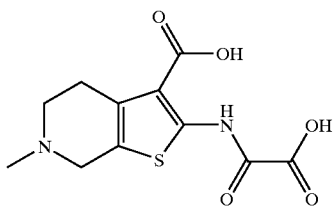

6-Methyl-2-(oxalyl-amino)-4,5,6,7-tetrahydro-thieno[2,3-c]pyridine-3-carboxylic Acid M.p.: >250° C.; Calculated for $C_{11}H_{12}N_2O_5S$, 0.6 $H_2O$; C, 44.77%; H, 4.51%; N, 9.49%. Found: C, 44.54%; H, 4.17%; N, 9.21%.

Example 5

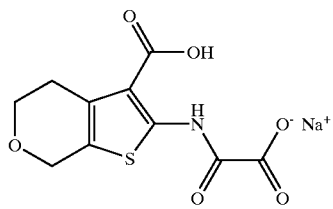

2-(Oxalyl-amino)-4,7-dihydro-5H-thieno[2,3-c]pyran-3-carboxylic Acid, Mono Sodium Salt M.p.: >250° C.; Calculated for $C_{10}H_8N_1O_6SNa$, 0.75× $H_2O$; C, 39.16%; H, 3.12%; N, 4.57%. Found: C, 39.29%; H, 3.67%; N, 4.41%.

Example 6

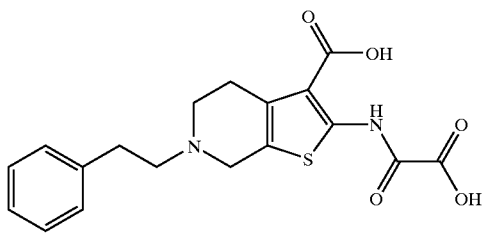

2-(Oxaly-amino)-6-phenethyl-4,5,6,7-tetrahydro-thieno[2,3-c]pyridine-3-carboxylic Acid Calculated for $C_{18}H_{18}N_2O_5S$, 1×$H_2O$; C, 55.09%; H, 5.14%; N, 7.14%. Found: C, 55.47%; H, 5.04%; N, 7.07%.

Example 7

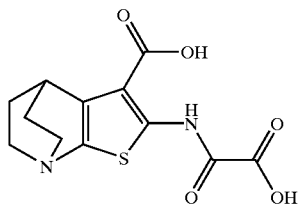

2-(Oxalyl-amino)-4,5,6,7-tetrahydro-4,7-ethano-thieno[2,3-b]pyridine-3-carboxylic Acid Calculated for $C_{12}H_{12}N_2O_5S$, 0.75×$H_2O$; C, 46.52%; H, 4.39%; N, 9.04%. Found: C, 46.48%; H, 4.79%; N, 8.87%.

Example 8

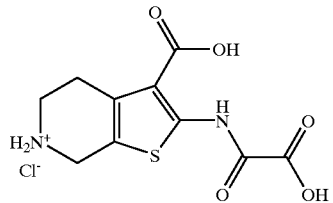

2-(Oxalyl-amino)-4,5,6,7-tetrahydro-thieno[2,3-c]pyridine-3-carboxylic Acid, Hydrochloride 4-Oxo-1-piperidine carboxylic acid tert-butyl ester was used as starting material. The Boc-group was removed using 25% trifluoroacetic acid in dichloromethane.

M.p.: >250° C.; Calculated for $C_{10}H_{10}N_2O_5S$, 1 HCl, 0.5×$H_2O$; C, 38.35%; H, 4.34%; N, 8.64%. Found: C, 38.04%; H. 3.83%; N, 8.87%.

Example 9

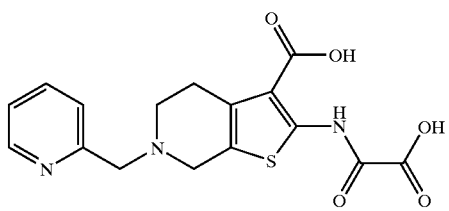

2-(Oxalyl-amino)-6-pyridin-2-ylmethyl-4,5,6,7-tetrahydro-thieno[2,3-c]pyridine-3-carboxylic Acid To a mixture of 2-(ethoxyoxalyl-amino)-4,5,6,7-tetrahydro-thieno[2,3-c]pyridine-3-carboxylic acid ethyl ester trifluoroacetic acid salt (1.5 g, 3.40 mmol, prepared as described in Example 8), potassium carbonate (2.4 g, 17.1 mmol), potassium iodine (100 mg) in acetone (40 ml) was added 2-picolyl chloride hydrochloride (0.61 g, 3.7 mmol). The resulting mixture was stirred at reflux temperature for 18 h., filtered and evaporated in vacuo. The residue was triturated with diethyl ether and the solid was filtered off and purified on silicagel (300 ml) using a mixture of ethyl acetate/ethanol/triethyl amine (3:1:0.4) as eluent. Pure fractions were collected and the eluent evaporated in vacuo affording 650 mg (39%) of 2-(ethoxyoxalyl-amino)-6-pyridin-2-ylmethyl-4,5,6,7-tetrahydro-thieno[2,3-c]pyridine-3-carboxylic acid triethyl ammonium salt as a solid.

To a solution of the above triethyl ammonium salt (650 mg, 1.40 mmol) in ethanol (15 ml) was added 1N aqueous sodium hydroxide (4.1 ml, 4.1 mmol) followed by water (15 ml). The resulting reaction mixture was stirred at room temperature for 18 h. The volatiles were evaporated in vacuo and the residue dissolved in water (20 ml) and washed with diethyl ether (2×10 ml). To the aqueous phase was added 1N hydrochloric acid to pH=1 and the aqueous phase was evaporated in vacuo. The residue was suspended in a mixture of 2-propanol/water (1:1, 40 ml), stirred for 1 h., the solid filtered off and washed with 2-propanol (2×15 ml) and dried in vacuo at 50° C. affording 181 mg (38%) of crude title compound. The crude product (181 mg) was dissolved in a mixture of water (10 ml) and 5 N sodium hydroxide (10 ml) and washed with diethyl ether (2×10 ml). The aqueous phase was acidified to pH=3 with 1 N hydrochloric acid and the precipitate filtered off and washed with water (3×20 ml), dried in vacuo at 50° C. for 18 h which afforded 51 mg (11%) of the title compound as a solid.

M.p.: 238–244° C.; Calculated for $C_{16}H_{15}N_3O_5S$, 2.5×$H_2O$; C, 47.29%; H, 4.96%; N, 10.34%. Found: C, 47.43%; H, 4.84%; N, 10.00%.

By a similar procedure as described in Example 9 the following compounds were prepared.

Example 10

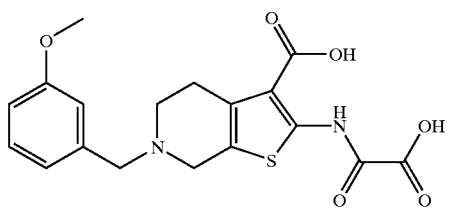

6-(3-Methoxy-benzyl)-2-(oxalyl-amino)-4,5,6,7-tetrahydro-thieno[2,3-c]pyridine-3-carboxylic Acid M.p.: 233–237° C.; Calculated for $C_{18}H_{18}N_2O_6S$, 1×$H_2O$; C, 52.93%; H, 4.94%; N, 6.86%. Found: C, 52.79%; H, 4.99%; N, 6.42%.

Example 11

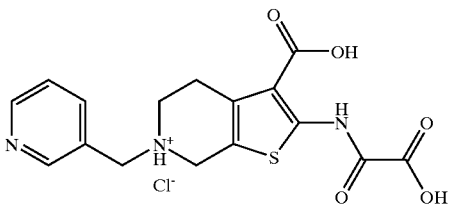

2-(Oxalyl-amino)-6-pyridin-3-ylmethyl-4,5,6,7-tetrahydro-thieno[2,3-c]pyridine-3-carboxylic Acid, Hydrochloride M.p.: 234–238° C.; Calculated for $C_{16}H_{15}N_3O_5S$, 1×HCl, 0.5×$H_2O$; C, 47.24%; H, 4.21%; N, 10.33%. Found: C, 47.35%; H, 4.10%; N, 10.35%.

Example 12

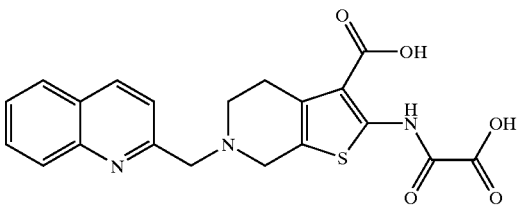

2-(Oxalyl-amino)-6-quinolin-2-ylmethyl-4,5,6,7-tetrahydro-thieno[2,3-c]pyridine-3-carboxylic Acid M.p.: >250° C.; Calculated for $C_{20}H_{17}N_3O_5S$, 1×$H_2O$; C, 55.95%; H, 4.22%; N, 9.61%. Found: C, 55.94%; H, 4.46%; N, 9.78%.

Example 13

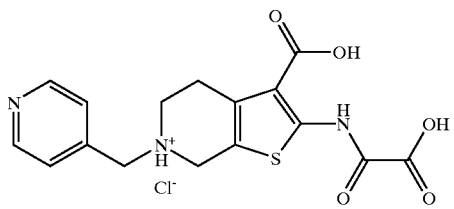

2-(Oxalyl-amino)-6-pyridin-4-ylmethyl-4,5,6,7-tetrahydro-thieno[2,3-c]pyridine-3-carboxylic Acid, Hydrochloride M.p.: 230–235° C.; Calculated for $C_{16}H_{15}N_3O_5S$, 1×HCl, 1×$H_2O$; C, 46.21%; H, 4.36%; N, 10.10%. Found: C, 45.82%; H, 4.42%; N, 10.02%.

Example 14

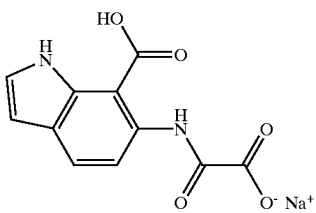

6(Oxalyl-amino)-1H-indole-7-carboxylic Acid, Mono Sodium Salt

To a stirred solution of 6-amino-1H-indole-7-carboxylic acid ethyl ester (1.5 g, 7.3 mmol, prepared as described in *J. Org. Chem.* 61, 1155–1158 (1996)), triethylamine (1.55 ml, 11.0 mmol) in dry tetrahydrofuran (100 ml) at 0° C. was added dropwise a solution of ethyl oxalyl chloride (980 μl, 88.0 mmol) in dry tetrahydrofuran (10 ml). The resulting reaction mixture was stirred at room temperature for 2 h. poured into ice water (300 ml) and the precipitate filtered off and dried in vacuo at 50° C. affording 2.25 g (100%) of 6-(ethoxyoxalyl-amino)-1H-indole-7-carboxylic acid ethyl ester as an oil.

To a solution of the above 1H-indole-7-carboxylic acid ethyl ester (2.0 g, 6.60 mmol) in ethanol (30 ml) was added 1N aqueous sodium hydroxide (16.4 ml, 16.4 mmol) in water (30 ml). The resulting reaction mixture was stirred at room temperature for 18 h. The volatiles were evaporated in vacuo and to the residual aqueous phase was added 1N hydrochloric acid to pH=1. The precipitate was filtered off and washed with water (2×50 ml), diethyl ether (2×30 ml) and dried in vacuo at 50° C. affording 1.34 g (82%) of the title compound as a solid.

M.p.: >250° C.; Calculated for $C_{11}H_7N_2O_5Na$, 1.5×$H_2O$; C, 44.46%; H, 3.39%; N, 9.43%. Found: C, 44.31%; H, 3.34%; N, 9.00%.

By a similar procedure as described in Example 14 the following compound was prepared.

Example 15

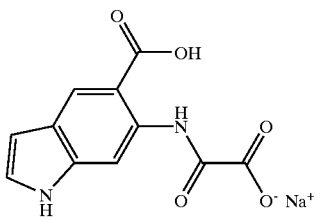

6-(Oxalyl-amino)-1H-indole-5-carboxylic Acid, Mono Sodium Salt 6-amino-1H-indole-5-carboxylic acid ethyl ester was prepared as described in *J. Org. Chem.* 61, 1155–1158 (1996)).

M.p.: >250° C.; Calculated for $C_{11}H_7N_2O_5Na$, 1.5×$H_2O$; C, 44.46%; H, 3.39%; N, 9.43%. Found: C, 44.44%; H, 3.68%; N, 9.00%.

Example 16

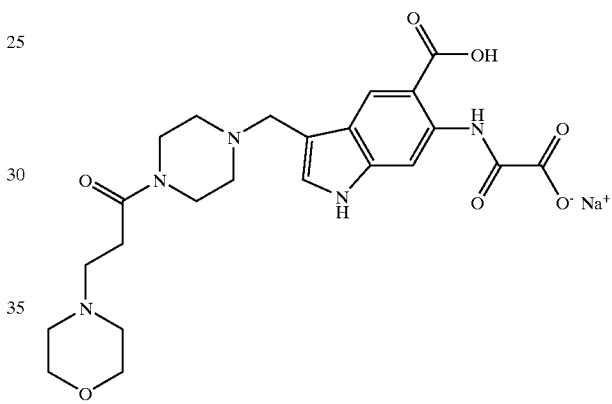

3-[-4-(3-Morpholin-4-yl-propionyl)-piperazin-1-ylmethyl]-6-(oxalyl-amino)-1H-indole-5-carboxylic Acid, Mono Sodium Salt To a ice cooled solution of 37% aqueous formaldehyde (2.7 g, 33.0 mmol) in acetic acid (8 ml) was added dropwise a solution of piperazine-1-carboxylic acid tert-butyl ester (2.7 g, 15 mmol). After stirring for 15 min. a solution of 6-(ethoxyoxalyl-amino)-1H-indole-5-carboxylic acid (4.0 g, 13.0 mmol) in a mixture of acetic acid (80 ml) and tetrahydrofuran (80 ml) was added and the resulting reaction mixture was stirred for 18 h. at room temperature. The volatiles were evaporated in vacuo and to the residue was added water (100 ml). The aqueous phase was extracted with ethyl acetate (2×100 ml), the combined organic extracts were washed with water (2×100 ml), saturated aqueous ammonium chloride (1×80 ml), dried ($MgSO_4$), filtered and evaporated in vacuo. The residue was trituated with diethyl ether (50 ml) and the precipitate was filtered off and washed with diethyl ether, dried in vacuo at 50° C. which afforded 3.4 g (51%) of 3-(4-tert-butoxycarbonyl-piperazin-1-ylmethyl)-6-(ethoxyoxalyl-amino)-1H-indole-5-carboxylic acid ethyl ester as a solid.

To a solution of the above 6-(ethoxyoxalyl-amino)-1H-indole-5-carboxylic acid ethyl ester in dichloromethane (20 ml) was added trifluoroacetic acid (20 ml) at room temperature. The resulting mixture was stirred for 1 h, the volatiles were evaporated in vacuo and to the residue was added water (50 ml) and the resulting mixture was stirred for ½ h. The precipitate was filtered off and washed with water (50 ml), diethyl ether (50 ml) and dried in vacuo at 50° C. which afforded 3.6 g (100%) of 6-(ethoxyoxalyl-amino)-3-piperazin-1-ylmethyl-1H-indole-5-carboxylic acid ethyl ester trifluoroacetic acid salt as a solid.

To a ice cooled mixture of the above piperazin (3.0 g, 5.81 mmol) in dichloromethane (100 ml) and triethylamine (2.5 ml) was added dropwise a mixture of chloropropionyl chloride (0.6 ml, 6.39 mmol) in dichloromethane (10 ml). The resulting mixture was stirred for 1 h at room temperature, washed with water (50 ml), dried (MgSO$_4$), filtered and evaporated in vacuo affording 1.8 g (68%) of 3-(4-acryloyl-piperazin-1-ylmethyl)-6-(ethoxyoxalyl-amino)-1H-indole-5-carboxylic acid ethyl ester as a oil.

To a solution of the above acryloyl-piperazin (0.5 g, 1.1 mmol) in ethanol (50 ml) was added morpholin (0.24 g, 2.74 mmol). The resulting mixture was stirred at reflux temperature for 18 h. and the volatiles were evaporated in vacuo. The residue was dissolved in water (50 ml), pH was adjusted to 2 with 1N hydrochloric acid and the resulting mixture washed with ethyl acetate (2×50 ml). The aqueous phase was neutralised with 1N sodium hydroxide, the precipitate was filtered off, washed with water and dried in vacuo at 50° C. for 3 h which afforded 0.3 g (50%) of 6-(ethoxyoxalyl-amino)-3-[-4-(3-morpholin-4-yl-propionyl)-piperazin-1-ylmethyl]-1H-indole-5-carboxylic acid ethyl ester as a solid.

To a solution of the above 1H-indole-5-carboxylic acid ethyl ester (0.2 g, 0.37 mmol) in ethanol (5 ml) was added sodium hydroxide (45 mg, 1.10 mmol) in water (15 ml). The resulting reaction mixture was stirred at room temperature for 18 h, pH adjusted to 1 by addition of 1 N hydrochloric acid. The aqueous phase was washed with ethyl acetate (2×25 ml) and pH adjusted to 5 by addition of 1N sodium hydroxide, followed by addition of dichloromethane (25 ml). The precipitate was filtered off and washed with water (50 ml) and dried in vacuo at 50° C. affording 30 mg (17%) of the title compound as a solid.

M.p.: >250° C.; LC-MS (E$^+$) M/Z 488

Example 17

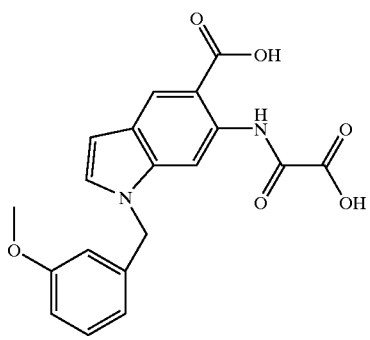

1-(3-Methoxy-benzyl)-6-(oxalyl-amino)-1H-indole-5-carboxylic Acid

To a solution of 6-amino-1H-indole-5-carboxylic acid ethyl ester (1.0 g, 3.30 mmol; prepared as described in *J. Org. Chem.* 61, 1155–1158 (1996)) in dry N,N-dimethylformamide (40 ml) was added sodium hydride (0.28 g, 7.3 mmol; 60% in mineral oil). The reaction mixture was stirred for 1.5 h and a solution of 3-methoxybenzylchloride (0.5 ml, 3.6 mmol) in dry N,N-dimethylformamide (2.5 ml) was added dropwise. The resulting reaction mixture was stirred for 1.5 h, poured into water (300 ml) and washed with diethyl ether (3×100 ml). Undissolved matter was filtered off and the aqueous phase was acidified to pH=4 by addition of 1 N hydrochloric acid. The precipitate was filtered off and washed with water, dried in vacuo at 50° C. affording 400 mg (29%) of 6-(ethoxyoxalyl-amino)-1-(3-methoxy-benzyl)-1H-indole-5-carboxylic acid ethyl ester as a solid.

To a solution of the above 1H-indole-5-carboxylic acid ethyl ester (0.3 g, 0.7 mmol) in ethanol (10 ml) was added 1 N sodium hydroxide (2.1 ml, 2.1 mmol) and water (10 ml). The resulting reaction mixture was stirred at room temperature for 18 h. The volatiles were evaporated in vacuo, pH adjusted to 2 by addition of 1N hydrochloric acid, the precipitate filtered off and washed with water, dried in vacuo at 50° C. affording 230 mg (89%) of the title compound as a solid.

M.p.: 222–226° C.; Calculated for C$_{19}$H$_{16}$N$_2$O$_6$, 0.4× H$_2$O; C, 60.77%; H, 4.51%; N, 7.46%. Found: C, 60.96%; H, 4.44%; N, 7.28%.

By a similar procedure as described in Example 1 the following compound was prepared.

Example 18

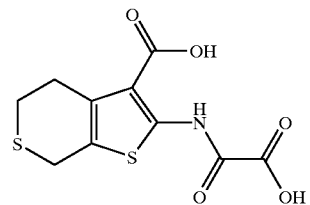

2-(Oxalyl-amino)-4,7-dihydro-5H-thieno[2,3-c]thiopyran-3-carboxylic Acid

Calculated for C$_{10}$H$_9$NO$_5$S$_2$; C, 41.80%; H, 3.16%; N, 4.88%. Found: C, 41.97%; H, 3.20%; N, 4.69%.

Example 19

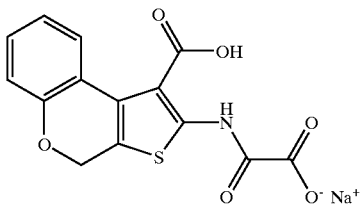

2-(Oxalyl-amino)-9H-thieno[2,3-c]chromen-3-carboxylic Acid, Mono Sodium Salt

To a solution of 4-cromanone (20 g, 0.14 mol), ethyl cyanoacetate (16.8 g, 0.15 mol) and ammonium acetate (11.4 g, 0.15 mol) in benzene (500 ml) was added acetic acid (5 ml), the resulting reaction mixture was heated at reflux temperature for 18 h and the formed water was collected in a Dean-Stark water trap. An additional portion of ammonium acetate (10 g, 0.13 mol) was added and heating at reflux temperature was continued for an additional 8 h. The volatiles were evaporated in vacuo, to the residue was added water (500 ml) and the aqueous phase was extracted with ethyl acetate (2×200 ml). The combined organic extracts were washed with water (2×100 ml), saturated aqueous sodium chloride (100 ml), dried (MgSO$_4$), filtered and evaporated in vacuo afforded 28 g of a 1:1 mixture of unchanged starting material and chroman-4-ylidene-cyano-acetic acid ethyl ester as an oil.

To a solution of the crude product in ethanol (250 ml) was added sulphur (2.5 g, 0.08 mol) and morpholin (15 ml). The resulting reaction mixture was stirred at 50° C. for 4 h cooled to room temperature and filtered. The volatiles were evaporated in vacuo affording 30 g of crude product.

The product was divided into two portions, of which one was semi purified on silica gel (900 ml) using a mixture of ethyl acetate/heptane (1:3). Semi pure fractions were collected and the solvent evaporated in vacuo affording a crude oil which was dissolved in diethyl ether (80 ml) and crystallised by addition of heptane (125 ml). The precipitate was filtered off, washed with heptane and dried in vacuo at 50° C. for 18 h affording 8.9 g (24%) of 2-amino-9H-thieno[2,3-c]chromen-3-carboxylic acid ethyl ester as a solid.

To a stirred solution of the above 2-amino-6H-thieno[2,3-c]chromen-3-carboxylic acid ethyl ester (2.9 g, 10.53 mmol), triethylamine (3 ml) in dry tetrahydrofuran (100 ml) at 0° C. was added dropwise a solution of ethyl oxalyl chloride (1.6 g, 11.6 mmol) in dry tetrahydrofuran (20 ml). The resulting reaction mixture was stirred at room temperature for 1.5 h. poured into ice water (200 ml) and the precipitate filtered off and dried in vacuo at 50° C. affording 2.6 g (66%) of 2-(ethoxyoxalyl-amino)-9H-thieno[2,3-c]chromen-3-carboxylic acid ethyl ester as a solid.

To a solution of the above ethyl ester (1.5 g, 4.0 mmol) in ethanol (25 ml) was added sodium hydroxide (480 mg, 12 mmol) and water (50 ml). The resulting reaction mixture was stirred at room temperature for 42 h. Water (100 ml) was added and the mixture was washed with diethyl ether (100 ml). The aqueous phase was acidified by addition of concentrated hydrochloric acid to pH=1, the precipitate was filtered off, washed with water and dried in vacuo at 50° C. for 6 h affording 0.6 g (47%) of the title compound as a solid.

M.p.: 227–228° C.; Calculated for C$_{14}$H$_9$NO$_6$SNa, 0.5 H$_2$O; C, 48.01%; H, 2.59%; N, 4.00%. Found: C, 48.39%; H, 2.93%; N, 3.93%.

Example 20

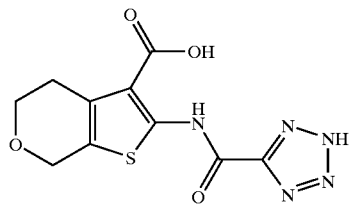

2-((2-H-Tetrazol-5-carbonyl)amino)-4,7-dihydro-5H-thieno[2,3-c]pyran-3-carboxylic Acid To a mixture of N,N-dimethylformamide (1.6 ml) and acetonitrile (5 ml) cooled to −20° C. was added dropwise a mixture of oxalyl chloride (0.8 g, 6.31 mmol) in acetonitrile (1 ml). The resulting mixture was stirred for 15 min. and tetrazole-5-carboxylic acid dipotassium salt (1 g, 5.25 mmol, prepared as described in *J. Med. Chem.* 29, 538–549 (1986)) was added and the resulting mixture was stirred for an additional 20 min. To the mixture was added dropwise a solution of 2-amino-4,5-dihydro-7H-thieno[2,3-c]pyran-3-carboxylic acid tert-butyl ester (1.3 g, 5.25 mmol), pyridine (2.2 ml) and acetonitrile (2.5 ml) during 10 min. The reaction mixture was allowed to reach room temperature where after it was heated at reflux temperature for 0.5 h. The cooled reaction mixture was poured into water (100 ml) and pH was adjusted to 1 by addition of concentrated hydrochloric acid. The precipitate was filtered off, washed with heptane and dried in vacuo at 50° C. for 18 h affording 1.3 g (70%) of 2-((1H-tetrazole-5-carbonyl)-amino)-4,7-dihydro-5H-thieno[2,3-c]pyran-3-carboxylic acid tert-butyl ester as a solid.

The above tert-butyl ester (0.6 g, 1.71 mmol) was dissolved in dichloromethane (5 ml) and trifluoroacetic acid (5 ml) was added. The resulting mixture was stirred for 40 min. at room temperature. The volatiles were evaporated in vacuo and to the residue was added diethyl ether (50 ml), water (25 ml) and 1 N sodium hydroxide (2 ml). The phases were separated and the aqueous phase was washed with diethyl ether (50 ml) and pH was adjusted to 1 by addition of concentrated hydrochloric acid. The precipitate was filtered off, washed with water (25 ml) and dried in vacuo at 50° C. for 18 h which afforded 190 mg (38%) of the title compound as a solid.

M.p.: >250° C.; Calculated for C$_{10}$H$_9$N$_5$O$_4$S, 0.25×H$_2$O; C, 40.07%; H, 3.19%; N, 23.36%. Found: C, 40.39%; H, 3.18%; N, 22.92%.

Example 21

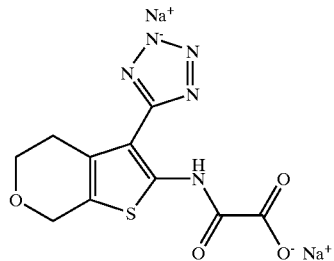

N-(3-(2H-Tetrazol-5-yl)-4,7-dihydro-5H-thieno[2,3-c]pyran-2-yl)oxalamic Acid, Di Sodium Salt 2-Amino-4,5-dihydro-7H-thieno[2,3-c]pyran-3-carboxylic acid ethyl ester (26 g, 0.114 mol) was dissolved in formamide (200 ml) and the resulting mixture was heated at reflux temperature for 1.5 h. After cooling to room temperature the precipitate was filtered off, washed with water (2×80 ml) and dried in vacuo at 50° C. for 18 h which afforded 10.0 g (42%) of 5,6-dihydro-8H-pyrano[4',3':4,5]thieno[2,3-d]pyrimidin-4-one as a solid.

To phosphorus oxychloride (70 ml) was added the above pyrimidin-4-one (7.0 g, 0.04 mol) and N,N-dimethylaniline (0.2 ml). The resulting mixture was heated at reflux temperature for 2 h, cooled and poured onto ice water (700 ml). The precipitate was filtered off, suspended in a mixture of ethyl acetate (400 ml) and water (250 ml) and stirred for 15 min. The aqueous phase was separated off and the organic phase was washed with saturated aqueous sodium chloride (100 ml), dried (MgSO$_4$), filtered and evaporated in vacuo which afforded 5.2 g (68%) of 4-chloro-5,6-dihydro-8H-pyrano[4',3':4,5]thieno[2,3-d]pyrimidine as a solid.

To a warm solution of the above thieno-pyrimidine (4.5 g, 0.02 mol) in ethanol (40 ml) was added dropwise a solution of hydrazine hydrate (10.0 ml) in ethanol (20 ml). The resulting solution was heated at reflux temperature for 2 h, cooled to room temperature, the precipitate filtered off, washed with ethanol (20 ml) and dried in vacuo at 50° C. for 1.5 h affording 3.2 g (73%) of 5,6-dihydro-8H-pyrano[4',3':4,5]thieno[2,3-d]pyrimidin-4-yl hydrazine as a solid.

To a solution of the above hydrazine (3.0 g, 0.014 mol) in 50% aqueous acetic acid (100 ml) cooled in a ice bath was added dropwise a solution of sodium nitrite (1.0 g, 0.015 mol) in water (10 ml). The reaction mixture was stirred for 2 h, the precipitate filtered off, washed with water (25 ml) and dried in vacuo at 50° C. for 1 h affording 3.0 g (95%) of 10,11-dihydro-8H-pyrano[4',3':4,5]thieno[3,2-e]tetrazolo[5,1-c]pyrimidine as a solid.

To a solution of the above tetrazol (2.5 g, 0.011 mol) in dioxane (30 ml) was added dropwise 1 N sodium hydroxide (25 ml). The reaction mixture was stirred for 3 h, poured into ice cooled water (100 ml) and pH was adjusted to 4 by addition of acetic acid. The precipitate was filtered off, washed with water (25 ml) and dried in vacuo at 50° C. for 18 h affording 2.2 g (82%) of N-(3-(2H-tetrazol-5-yl)-4,7-dihydro-5H-thieno[2,3-c]pyran-2-yl)formamide as a solid.

The above formamide (0.6 g, 2.7 mmol) was dissolved in dry tetrahydrofuran (50 ml) and triethylamine (1 ml) was added. To the resulting mixture cooled in a ice bath was added dropwise a solution of ethyl oxalylchloride (0.4 g, 2.96 mmol) in dry tetrahydrofuran (5 ml). The resulting reaction mixture was stirred for 2 h at room temperature, the volatiles were evaporated in vacuo. To the residue was added water (50 ml), diethyl ether (50 ml) and 1 N hydrochloric acid to pH=2 and a small precipitate was filtered off. The organic phase was separated, dried ($Na_2SO_4$), filtered and evaporated in vacuo. The residue (0.4 g) was suspended in dichloromethane (20 ml) and stirred for 1 h, the solid matter was filtered off and dried in vacuo at 50° C. affording 0.16 g (18%) of N-(3-(2H-tetrazol-5-yl)-4,7-dihydro-5H-thieno[2,3-c]pyran-2-yl)oxalamic acid ethyl ester as a solid.

To a solution of the above oxalamic acid ethyl ester (0.16 g, 0.49 mmol) in ethanol (15 ml) was added 1 N sodium hydroxide (1.0 ml, 1.01 mmol). The resulting reaction mixture was stirred at room temperature for 2 h. The precipitate was filtered off and washed with ethanol (10 ml), dried in vacuo at 50° C. for 48 h affording 140 mg (83%) of the title compound as a solid.

M.p.: >250° C.; Calculated for $C_{10}H_9N_5O_4SNa_2$, $3 \times H_2O$; C, 30.54%; H, 3.33%; N, 17.81%. Found: C, 30.70%; H, 3.35%; N, 17.49%.

By a similar procedure as described in Example 1 the following compounds were prepared.

Example 22

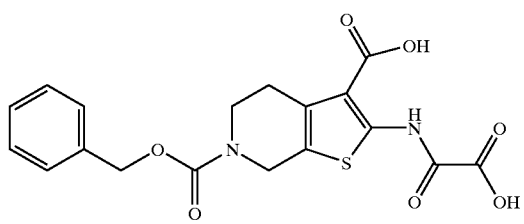

2-(Oxalyl-amino)-4,7-dihydro-5H-thieno[2,3-c]pyridine-3,6-dicarboxylic Acid 6-Benzyl Ester M.p.: >250° C.; Calculated for $C_{18}H_{16}N_2O_7S$; C, 53.46%; H, 3.99%; N, 6.93%. Found: C, 53.44%; H, 4.15%; N, 6.69%.

Example 23

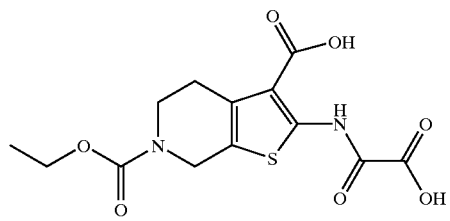

2-(Oxalyl-amino)-4,7-dihydro-5H-thieno[2,3-c]pyridine-3,6-dicarboxylic Acid 6-Ethyl Ester M.p.: 245–247° C.; Calculated for $C_{13}H_{14}N_2O_7S$; C, 45.61%; H, 4.12%; N, 8.18%. Found: C, 45.71%; H, 4.31%; N, 7.86%.

Example 24

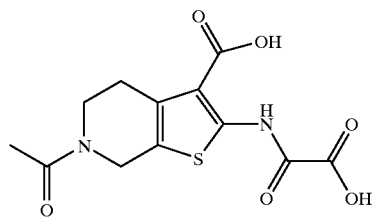

6-Acetyl-2-(oxalyl-amino)-4,5,6,7-tetrahydro-thieno[2,3-c]pyridine-3-carboxylic Acid M.p.: 242–244° C.; Calculated for $C_{12}H_{12}N_2O_6S$, $0.25 \times H_2O$; C, 45.50%; H, 3.98%; N, 8.84%. Found: C, 45.64%; H, 3.97%; N, 8.51%.

Example 25

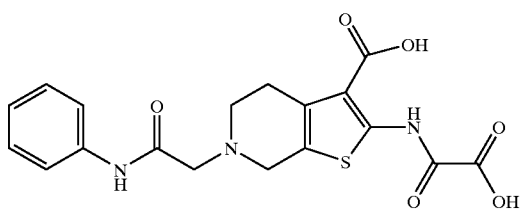

2-(Oxalyl-amino-)-6-phenylcarbamoylmethyl-4,5,6,7-tetrahydro-thieno[2,3-c]pyridine-3-carboxylic Acid M.p.:244–246° C.; Calculated for $C_{18}H_{17}N_3O_6S$, $1 \times H_2O$; C, 51.30%; H, 4.54%; N, 9.97% Found: C, 51.08%; H, 4.52%; N, 9.63

Example 26

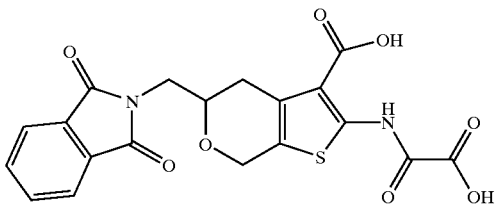

5-(1,3-Dioxo-1,3-dihydro-isoindol-2-ylmethyl)-2-(oxalyl-amino)-4,7-dihydro-5H-thieno[2,3-c]pyran-3-carboxylic Acid To a mixture of benzyloxyacetaldehyde (8.3 g, 0.06 mol) in benzene (80 mL) was added 1-methoxy-3-trimethylsilyloxy-1,3-butadiene (10.6 g, 0.06 mol). The reaction mixture was stirred under nitrogen for 15 min., cooled to 0° C. and a solution of 0.5 M zinc chloride (55 ml, 0.03 mol) was added dropwise. The reaction mixture was allowed to warm to room temperature over 16 h and evaporated in vacuo. The resultant oil was diluted with ethyl acetate (100 ml), washed with 1N hydrochloric acid (3×50 ml), saturated sodium bicarbonate (3×50 ml), brine (3×50 ml), dried (MgSO$_4$) and evaporated in vacuo. The resulting oil was subjected to flash chromatography using a mixture of ethyl acetate:hexanes (1:2) as eluent. Pure fractions were collected affording after evaporation in vacuo 7.1 g (60%) of benzyloxy-methyl-2,3-dihydro-pyran-4-one as an oil.

$^1$H NMR (400 MHz, CDCl$_3$) δ 7.39–7.31 (m, 6H), 5.42 (dd, J=6,1Hz, 1H), 4.61 (d, J=3 Hz, 1H), 4,57 (m, 1H), 3.70 (m, 2H), 2.74 (dd, J=17 Hz, 14 Hz, 1H), 2.41 (ddd, J=17 Hz, 2 Hz, 1Hz, 1H).

The above 2,3-dihydro-pyran-4-one (7.1 g, 0.032 mol) and 10% palladium on carbon (0.4 g) in ethyl acetate (50 ml) were placed in a Parr bomb shaker and hydrogenated at 30 psi. The reaction mixture was shaken for 2 h, at which time TLC analysis (methanol/dichloromethane 1:9) indicated the reaction was complete. The reaction mixture was filtered through a pad of Celite and the volatiles evaporated in vacuo. The residue was subjected to flash column chromatography using ethyl acetate as eluent. Pure fractions were collected affording after evaporation in vacuo 3.0 g (75%) of 2-hydroxymethyl-tetrahydro-pyran-4-one as an oil.

$^1$H NMR (400 MHz, CDCl$_3$) δ 4.36–4.29 (m, 1H), 3.77–3.66 (m, 3H), 3.61–3.54 (m, 1H), 2.65–2.43 (m, 2H), 2.34–2.27 (m, 2H), 2.04 (bs, 1H, CH$_2$OH).

The above tetrahydro-pyran-4-one (1.90 g, 0.015 mol), tert-butyl cyanoacetate (2.7 g, 0.019 mol), sulfur (0.51 g, 0.016 mol) and morpholine (2.55 ml, 0.03 mol) were dissolved in absolute ethanol (20 ml), and heated to 50° C. for 16 h. The reaction mixture was cooled, filtered and the filtrate evaporated in vacuo. The resultant oil was dissolved in ethyl acetate (50 ml), washed with water (2×50 ml), brine (2×50 m) and dried (MgSO$_4$). The solvent was evaporated in vacuo and the residue was subjected to flash column chromatography using ethyl acetate/hexanes (1:1) as eluent. Pure fractions were collected affording after evaporation in vacuo 3.7 g (90%) of 2-amino-5-hydroxymethyl-4,7-dihydro-5H-thieno[2,3-c]pyran-3-carboxylic acid tert-butyl ester as a solid.

$^1$H NMR (400 MHz, CDCl$_3$) δ 4.64 (s, 2H), 3.80–3.67 (m, 3H), 2.77–2.72 (m,1H), 2.57–2.53 (m, 1H), 1.54 (s, 9H).

The above carboxylic acid tert-butyl ester (3.0 g, 0.015 mol), phthalimide (2.10 g, 0.014 mol) and triphenylphosphine (3.68 g, 0.014) were dissolved in dry tetrahydro-furan (60 ml) and cooled to 0° C. under a nitrogen atmosphere. Diisopropyl azodicarboxylate (DIAD) (2.71 ml, 0.014 mol) was added dropwise at 0° C. and the solution allowed to stir overnight, slowly warming to room temperature. The volatiles were evaporated in vacuo and the resultant solid dissolved in ethyl acetate (60 ml). The organic phase was washed with brine (2×50 ml), dried (MgSO$_4$) and evaporated in vacuo. The residue was subjected to flash column chromatography initially eluted with a mixture of ethyl acetate:hexanes (1:3). Once the product began to elute, the eluent mixture was switched to ethyl acetate/hexanes (1:2). Pure fractions were collected affording after evaporation in vacuo 2.90 g (47%) of 2-amino-5-(1,3-dioxo-1,3-dihydro-isoindol-2-ylmethyl)-4,7-dihydro-5H-thieno[2,3-c]pyran-3-carboxylic acid tert-butyl ester as a solid.

$^1$H NMR (400 MHz, CDCl$_3$) δ 7.87–7.85 (m, 2H), 7.83–7.71 (m, 2H), 5.94 (bs, 2H), 4.59 (d, J=14 Hz, 1H), 4.52 (d, J=14 Hz, 1H), 4.0–3.98 (m, 2H), 3.83–3.79 (m, 1H), 2.87 (d, J=17 Hz,1H), 2.58 (dd, J=17 Hz, 9 Hz, 1H), 1.50 (s, 9H).

To the above 4,7-dihydro-5H-thieno[2,3-c]pyran-3-carboxylic acid tert butyl ester (0.5 g, 1.2 mmol) dissolved in dichloromethane (5 ml), was added triethylamine (0.33 ml, 2.4 mmol) and imidazol-1-yl-oxo-acetic acid tert butyl ester (0.47 g, 2.4 mmol) under nitrogen. The reaction mixture was allowed to stir at room temperature for 18 hours. The volatiles were evaporated in vacuo and the solid residue dissolved in ethyl acetate (20 ml). The organic phase was washed with 1% hydrochloric acid (2×10 ml), brine (2×10 ml), dried (MgSO$_4$). The organic phase was evaporated in vacuo affording 0.64 g (99%) of 2-(tert-butoxyoxalyl-amino)-5-(1,3-dioxo-1,3-dihydro-isoindol-2-ylmethyl)-4,7-dihydro-5H-thieno[2,3-c]pyran-3-carboxylic acid tert-butyl ester as a solid.

$^1$H NMR (400 MHz, CDCl$_3$) δ 12.48 (s, 1H, NHCO), 7.88–7.86 (m, 2H), 7.74–7.72 (m, 2H), 4.78 (d, J=19 Hz, 1H), 4.65 (d, J=19 Hz, 1H), 4.07–3.90 (m, 2H), 3.88–3.80 (m, 1H), 2.97 (d, J=17 Hz, 1H), 2.68 (dd, J=17 Hz, 9 Hz, 1H), 1.58 (s, 9H), 1.54 (s, 9H).

The above di-tert-butyl ester (2.8 g, 5.16 mmol) was dissolved in a mixture of trifluoroacetic acid and dichloromethane (1:5) (36 ml). The reaction was stirred at room temperature for 6 hr. The precipitate was filtered off, washed with diethyl ether, dried in vacuo at 50° C. which afforded 1.26 g (57%) of the title compound as a solid.

M.p.: 245.2–245.6° C.; $^1$H NMR (300 MHz, DMSO-d$_6$) δ 12.32 (s, 1H, NHCO), 7.95–7.80 (m, 4H), 4.75 (d, J=20 Hz, 1H), 4.62 (d, J=20 Hz, 1H), 3.96–3.69 (m, 3H), 3.01 (d, J=18 Hz, 1H), 2.60 (dd, J=18 Hz, 9 Hz, 1H); Calculated for C$_{19}$H$_{14}$N$_2$O$_8$S; C, 53.02%; H, 3.28%; N, 6.51%. Found: C, 53.01%; H, 3.31%; N, 6.41%.

Example 27

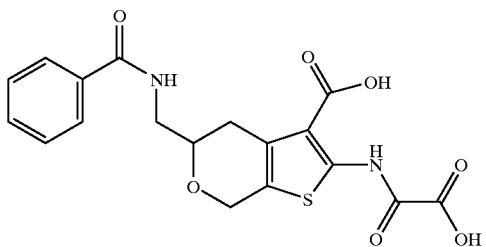

5-(Benzolamino-methyl)-2-(oxalyl-amino)-4,7-dihydro-5H-thieno[2,3-c]pyran-3-carboxylic Acid 2-(tert-Butoxyoxalyl-amino)-5-(1,3-dioxo-1,3-dihydro-isoindol-2-ylmethyl)-4,7-dihydro-5H-thieno[2,3-c]pyran-3-carboxylic acid tert-butyl ester (0.33 g, 0.60 mmol) was dissolved in a solution of ethanol (2 ml) and dichloromethane (3 ml). Hydrazine (28 µl, 0.9 mmol) was added and the reaction stirred under nitrogen at room temperature for 24 h. TLC analysis indicated that starting material was still present. An additional portion of hydrazine (28 µl, 0.9 mmol) was added and the reaction stirred at room temperature for another 16 h, then at 45° C. for 5 h. The mixture was concentrated in vacuo, redissolved in dichloromethane and the insoluble material filtered off. The filtrate was collected and concentrated in vacuo affording crude 5-aminomethyl-2-(tert-butoxyoxalyl-amino)-4,7-dihydro-5H-thieno[2,3-c] pyran-3-carboxylic acid tert-butyl ester as a solid, which was carried through to the next step without further purification.

The above crude 5H-thieno[2,3-c]pyran-3-carboxylic acid tert-butyl ester (0.25 g, 0.60 mmol) was suspended in a mixture of dichloromethane and acetonitrile (1:1, 5 ml). Triethylamine (0.25 ml, 1.8 mmol) was added followed by 1-hydroxy-benzotriazole hydrate (0.10 g, 0.72 mmol) and 1-(3-dimethylaminopropyl)-3-ethylcarbodiimide hydrochloride (0.14 g, 0.72 mmol) as solids. The heterogeneous reaction mixture was allowed to stir at room temperature for 2 days, after which the mixture was homogenous. The solvents were evaporated in vacuo, the residue dissolved in dichloromethane washed twice with 1M hydrochloric acid, then with saturated sodium bicarbonate. The organic phase was dried (Na$_2$SO$_4$), filtered and concentrated in vacuo affording a solid which was purified by flash chromatography using a mixture of ethyl acetate and hexanes (1:1) as eluent. Pure fractions were collected and evaporated in vacuo affording 50 mg (16% over two steps) of 5-(benzoylamino-methyl)-2-(tert-butoxyoxalyl-amino)-4,7-dihydro-5H-thieno[2,3-c]pyran-3-carboxylic acid tert-butyl ester as a solid.

$^1$H NMR (400 MHz, CDCl$_3$) δ 12.46 (s, 1H), 7.81 (d, J=7 Hz, 2H), 7.51 –7.42 (m, 3H), 6.72 (bs, 1H), 4.83 (d, J=17 Hz, 1H), 4.74 (d, J=17 Hz, 1H), 4.05–3.98 (m, 1H), 3.86–3.78 (m, 1H), 3.45–3.38 (m, 1H), 2.97 (d, J=19 Hz, 1H), 2.68 (dd, J=19 Hz, 9 Hz, 1H), 1.61 (s, 9H),1.58 (s, 9H).

The above benzoylamino-methyl-thieno[2,3-c]pyran (40 mg, 0.078 mmol) was treated with 20% trifluoroacetic acid/dichloromethane (2 ml) for 4 h. The volatiles were evaporated in vacuo and chased twice with dichloromethane, forming a precipitate which was filtered off and dried yielding 30 mg (95%) of the title compound as a solid.

$^1$H NMR (400 MHz, DMSO-d$_6$) δ 12.31 (s, 1H), 8.63 (t, J=4 Hz, 1H), 7.86 (d, J=7 Hz, 2H), 7.51–7.43 (m, 3H), 4.80 (d, J=17 Hz, 1H), 4.64 (d, J=17 Hz, 1H), 3.82 (m, 1H), 3.44 (m, 2H), 2.95 (d, J=18, 1H), 2.52 (dd, J=18 Hz, 9 Hz, 1H); LC/MS [M–H]: 403.39; HPLC (254.4nm): 2.99 s, 84%.

Example 28

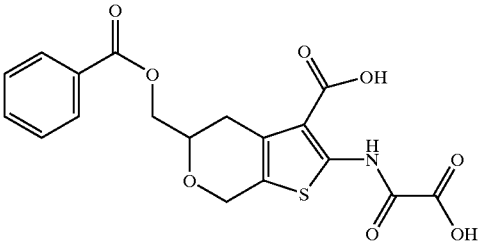

5-Benzoyloxymethyl-2-(oxalyl-amino)-4,7-dihydro-5H-thieno[2,3-c]pyran-3-carboxylic Acid 2-Amino-5-hydroxymethyl-4,7-dihydro-5H-thieno[2,3-c]pyran-3-carboxylic acid tert-butyl ester (0.23 g, 0.87 mmol) benzoic acid (0.10 g, 0.96 mmol) and triethylamine (0.23 ml, 1.7 mmol) were dissolved in dichloromethane (4 ml) and stirred under nitrogen. 1-(3-Dimethylaminopropyl)-3-ethylcarbodiimide hydrochloride (0.17 g, 0.96 mmol) and 1-hydroxy-benzotriazole hydrate (0.12 g, 0.96 mmol) were added as solids. The reaction mixture was stirred at room temperature for 2 days, after which the solvents were evaporated in vacuo. The crude mixture was dissolved in ethyl acetate and washed with 1N hydrochloric acid, saturated sodium bicarbonate, brine and dried (Na$_2$SO$_4$). The solvent was evaporated in vacuo, yielding a yellow solid that was purified by flash chromatography using a mixture of ethyl acetate and hexanes (1:2) as eluent. Pure fractions were collected and evaporated in vacuo affording 0.22 g (70%) of 2-amino-5-benzoyloxymethyl-4,7-dihydro-5H-thieno[2,3] pyran-3-carboxylic acid tert-butyl ester as a solid.

$^1$H NMR (400 MHz, CDCl$_3$) δ 8.06 (d, J=7 Hz, 2H), 7.55 (t, J=7 Hz, 1H), 7.42 (t, J=7 Hz, 2H), 4.64 (s, 2H), 4.44 (d, J=5 Hz, 2H), 4.03–3.97 (m, 1H), 2.88 (d, J=18 Hz, 1H), 2.64 (dd, J=17 Hz, 10 Hz, 1H), 1.50 (s, 9H); LC/MS [M+H]: 390.48.

To the above carboxylic acid tert-butyl ester (0.18 g, 0.45 mmol) dissolved in dry tetrahydrofuran (5 ml), was added triethylamine (0.18 ml, 1.4 mmol) and imidazol-1-yl-oxoacetic acid tert-butyl ester (0.26 g, 1.4 mmol) under nitrogen. The reaction mixture was stirred at room temperature for 3 h. The volatiles were evaporated in vacuo and the resultant solid reconstituted in ethyl acetate (10 ml). The organic layer was washed with 1% hydrochloric acid (2×10 ml), brine (2×10 ml), dried (Na$_2$SO$_4$), filtered and the solvent evaporated in vacuo. The resulting oil was purified by flash chromatography using a mixture of ethyl acetate and hexane (1:2) as eluent affording ester 0.20 g (90%) of 5-benzoyloxymethyl-2-(tert-butoxyoxalyl-amino)-4,7-dihydro-5H-thieno[2,3-c]pyran-3-carboxylic acid tert-butyl ester as a solid.

$^1$H NMR (400 MHz, CDCl$_3$) δ 8.07 (d, J=7 Hz, 2H), 7.56 (t, J=7 Hz, 1H), 7.44 (t, J=7 Hz, 2H), 4.85 (d, J=15 Hz, 1H), 4.77 (d, J=15 Hz, 1H), 4.49 (d, J=5 Hz, 2H), 4.03–3.99 (m, 1H), 2.99 (d, J=17 Hz, 1H), 2.72 (dd, J=17 Hz, 11Hz, 1H), 1.58 (s, 9H), 1.60 (s, 9H).

The above di-tert butyl ester (0.15 g, 0.29 mmol) was dissolved in a solution of 20% trifluoroacetic acid in dichloromethane (3 ml). Immediately the solution developed a dark orange color that quickly became red. The reaction was stirred for 1.5 h at room temperature. The volatiles were evaporated in vacuo affording a brown solid which was washed twice with diethyl ether and water and filtered off. The resulting solid was dried in vacuo, yielding 30 mg (25%) of the title compound as a solid.

$^1$H NMR (400 MHz, DMSO$_6$) δ 12.40 (s, 1H), 7.98 (d, J=7 Hz, 2H), 7.67 (t, J=7 Hz, 1H), 7.54 (t, J=7 Hz, 2H), 4.83 (d, J=15 Hz, 1H), 4.70 (d, J=15 Hz, 1H), 4.44 (d, J=5 Hz, 2H), 4.02–3.99 (m, 1H), 2.99 (d, J=16 Hz, 1H), 2.70 (dd, J=16 Hz, 9 Hz, 1H); LC/MS [M–H]: 404.05; HPLC. (254.4 nm): 7.16 s, 90%.

Example 29

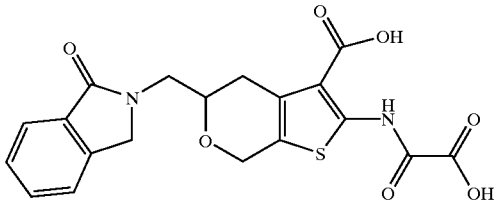

2(Oxalyl-amino)-5-(1-oxo-1,3-dihydro-isoindol-2-ylmethyl)-4,7-dihydro-5H-thieno[2,3-c]pyran-3-carboxylic Acid To a solution of 2-amino-5-(1,3-dioxo-1,3-dihydro-isoindol-2-ylmethyl)-4,7-dihydro-5H-thieno[2,3-c]pyran-3-carboxylic acid tert-butyl ester (0.308 g, 0.74 mmol) in absolute ethanol (5 ml) was added hydrazine (47 µl, 1.48 mmol). The reaction was stirred at 80° C. for 4 h and then at room temperature for another 12 h. The precipitate formed was filtered off and the filtrate concentrated in vacuo. To the oily residue was added dichloromethane (15 ml) and the precipitate formed was filtered off. The filtrate was concentrated in vacuo to give 2-amino-5-aminomethyl-4,7-dihydro-5H-thieno[2,3-c]pyran-3-carboxylic acid tert-butyl ester 0.19 g (90%) as a solid.

$^1$H NMR (400 MHz, CDCl$_3$) δ 5.91 (bs, 2H), 4.62 (s, 2H), 3.64–3.60 (m, 1H), 2.92–2.84 (m, 2H), 2.80–2.75 (m, 1H), 2.52–2.45 (m, 1H), 1.53 (s, 9H); LC-MS [M+H]$^+$: 285.

Phthalic dicarboxaldehyde (52 mg, 0.36 mmol) was dissolved in a mixture of anhydrous acetonitrile (2 ml) and acetic acid (44 µl, 0.72 mmol). The above 2-amino-5-aminomethyl-4,7-dihydro-5H-thieno[2,3-c]pyran-3-carboxylic acid tert-butyl ester (0.11 g, 0.36 mmol) was added and the reaction stirred for 20 minutes at room temperature. The volatiles were evaporated in vacuo and the residue dissolved in ethyl acetate (25 ml). The organic mixture was washed with saturated sodium bicarbonate (5 ml), 1% hydrochloric acid (5 ml), brine (5 ml), dried (Na$_2$SO$_4$), filtered and evaporated in vacuo. The residue was purified by chromatography using a gradient from 15% ethyl acetateldichloromethane to 17% ethyl acetate/dichloromethane as eluent affording 45 mg (30%) of 2-amino-5-(1-oxo-1,3-dihydro-isoindol-2-ylmethyl)-4,7-dihydro-5H-thieno[2,3-c]pyran-3-carboxylic acid tert-butyl ester as a solid.

$^1$H NMR (400 MHz, CDCl$_3$) δ 7.85 (d, J=7 Hz, 1H), 7.53 (t, J=7 Hz, 1H), 7.47–7.43 (m, 2H), 4.68 (d, J=17 Hz, 1H), 4.58–4.51 (m, 3H), 3.99 (dd, J=14 Hz, 3 Hz, 1H), 3.93–3.89 (m, 1H), 3.66–3.61 (m, 1H), 2.88 (d, J=17 Hz, 1H), 2.55 (dd, J=17 Hz, 11Hz, 1H), 1.52 (s, 9H).

To a solution of 2-amino-5-(1-oxo-1,3-dihydro-isoindol-2-ylmethyl)-4,7-dihydro-5H-thieno[2,3-c]pyran-3-carboxylic acid tert-butyl ester (45 mg, 1.1 mmol) in anhydrous dichloromethane (4 ml) was added imidazol-1-yl-oxo-acetic acid tert-butyl ester (73 mg, 3.3 mmol) and triethylamine (17 µl, 1.1 mmol). The reaction was stirred under nitrogen at room temperature for 5 h. The solvent was evaporated in vacuo and the crude material was dissolved in ethyl acetate (20 ml). The organic solution was washed with 0.5 N hydrochloric acid (3 ml), saturated sodium bicarbonate (3 ml), brine (5 ml), dried (Na$_2$SO$_4$), filtered and the solvent evaporated in vacuo. The residue was purified by chromatography using dichloromethane (100%) followed by 17% ethyl acetate/dichloromethane as eluents affording 54 mg (91%) of 2-(tert-butoxyoxalyl-amino)-5-(1-oxo-1,3-dihydro-isoindol-2-ylmethyl)-4,7-dihydro-5H-thieno[2,3-c]pyran-3-carboxylic acid tert-butyl ester as a solid.

$^1$H NMR (400 MHz, CDCl$_3$) δ 12.50 (s, 1H), 7.84 (d, J=8 Hz, 1H), 7.53 (t, J=7 Hz, 1H), 7.47–7.43 (m, 2H), 4.81–4.65 (m, 3H)$_1$ 4.53 (d, J=17 Hz, 1H), 4.01 (dd, J=14 Hz, 3 Hz, 1H), 3.96–3.89 (m, 1H), 3.69–3.62 (m, 1H), 2.97 (d, J=17 Hz, 1H), 2.63 (dd, J=17 Hz, 11Hz, 1H), 1.59 (s, 9H), 1.56 (s, 9H); APCl-MS [M+H]$^+$: 529.5.

The above 2-(tert-butoxyoxalyl-amino)-5-(1-oxo-1,3-dihydro-isoindol-2-ylmethyl)-4,7-dihydro-5H-thieno[2,3-c]pyran-3-carboxylic acid tert-butyl ester (52 mg, 0.098 mmol) was treated with a solution of 50% trifluoroacetic acid/dichloromethane (3 ml) for 4.5 h at room temperature. The volatiles were evaporated in vacuo and the residue chased three times with dichloromethane (10 ml). The solid formed was filtered off and washed with dichloromethane affording 28 mg (70%) of the title compound as a solid.

$^1$H NMR (400 MHz, DMSO-d$_6$) δ 12.32 (s, 1H), 7.69 (d, J=8 Hz, 1H), 7.61–7.59 (m, 2H), 7.51–7.45 (m, 1H), 4.81 (d, J=15 Hz, 1H), 4.65 (d, J=15 Hz, 1H), 4.60 (s, 2H), 3.95–3.92 (m, 1H), 3.75 (d, J=5 Hz, 2H), 2.94 (d, J=16 Hz, 1H), 2.56 (dd, J=16 Hz,10 Hz, 1H); APCl-MS [M+H]$^+$: 417.3; HPLC (254.4nm): 3.079 s (100%).

Example 30

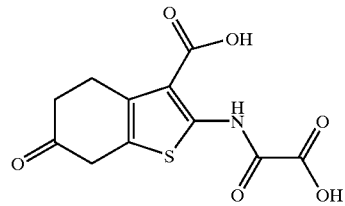

2-(Oxalyl-amino)-6-oxo-4,5,6,7-tetrahydro-benzo[b]thiophene-3-carboxylic Acid 2-(Ethoxyoxalyl-amino)-6-oxo-4,5,6,7-tetrahydro-benzo[b]thiophene-3-carboxylic acid (3.0 g, 0.013 mol) was dissolved in a mixture of water (40 ml), ethanol (20 ml) and tetrahydrofuran (20 ml) at room temperature. To the resulting mixture was added 1 N sodium hydroxide (20.24 ml, 20.24 mmol). The resulting reaction mixture was stirred at room temperature for 72 h, pH was adjusted to 3 by addition of concentrated hydrochloric acid. The precipitate was filtered off and washed with water (2×15 ml), diethyl ether (2×15 ml) and dried in vacuo at 50° C. affording 1.96 g (73%) of the title compound as a solid.

M.p.: >230° C.; Calculated for $C_{11}H_9NO_8S$; C, 46.64%; H, 3.30%; N, 4.94%. Found: C, 46.97%; H, 3.30%; N, 5.80%.

By a similar procedure as described in Example 1 the following compounds have been prepared.

Example 31

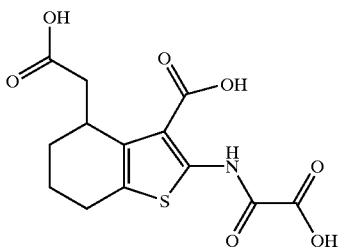

4-Carboxymethyl-2-(oxalyl-amino)-4,5,6,7-tetrahydro-benzo-[b]thiophene-3-carboxylic Acid 2-Carbmethoxymethylcyclohexanone was prepared in the same way as described in *J. Am. Chem. Soc.* 81, 3955–3959 (1959) for 2-carbethoxy-methylcyclohexanone.

M.p.: >250° C.; Calculated for $C_{13}H_{13}N_1O_7S_1$, 0.75 $H_2O$; C, 45.81%; H, 4.29%; N, 4.11%. Found: C, 45.79%; H, 4.02%; N, 4,08%.

Example 32

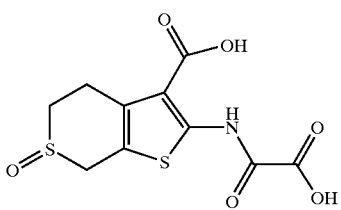

2-(Oxalyl-amino)-6-oxo-4,7-dihydro-5H-thieno[2,3-c]thiopyran-3-carboxylic Acid

1-Oxo-2,3,5,6-tetrahydro-4H-thiopyran-4-one was prepared as described in *J. Org. Chem.* 27, 282–284 (1962).

M.p.: >250° C.; Calculated for $C_{10}H_9N_1O_6S_2$, 0.2×NaCl; C, 38.13%; H, 2.88%; N, 4.45%. Found: C, 37.98%; H, 2.82%; N, 4,29%.

Example 33

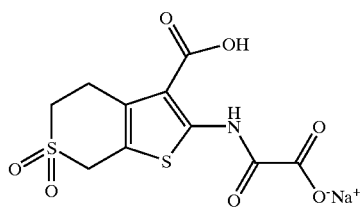

2(Oxalyl-amino)-6,6-dioxo-4,7-dihydro-5H-thieno[2,3-c]thiopyran-3-carboxylic Acid, Mono Sodium Salt 1,1-Dioxide-2,3,5,6-tetrahydro-4H-thiopyran-4-one was prepared as described in *J. Org. Chem.* 60, 1665–1673 (1995).

M.p.: >250° C.; Calculated for $C_{10}H_8N_1O_7S_2Na_1$, 1×$H_2O$; C, 33.43%; H, 2.81%; N, 3.90%. Found: C, 33.43%; H, 2.78%; N, 3,76%.

By a similar procedure as described in Example 27 the following compounds have been prepared.

Example 34

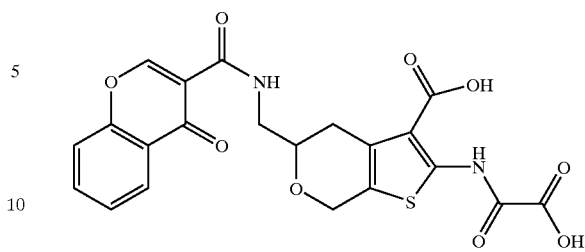

2-(Oxalyl-amino)-5-(((4-oxo-chromene-4H-3-carbonyl)amino)methyl)-4,7-dihydro-5H-thieno[2,3-c]pyran-3carboxylic Acid $^1$H NMR (400 MHz, DMSO-$d_6$) δ 12.32 (s, 1H), 9.47 (t, J=4 Hz, 1H), 9.08 (s, 1H), 8.19 (dd, J=8 Hz, 2 Hz, 1H), 7.90 (dt, J=8 Hz, 2 Hz, 1H), 7.78 (d, J=8 Hz, 1H), 7.60 (t, J=8 Hz, 1H), 4.88 (d, J=15 Hz, 1H), 4.70 (d, J=15 Hz, 1H), 3.83–3.79 (m, 1H), 3.72–3.66 (m, 1H), 3.55–3.48 (m, 1H), 2.95 (d, J=15 Hz, 1H), 2.60 (dd, J=15 Hz, 8 Hz, 1H); LC/MS [M–H]$^-$: 471.4; HPLC (254.4 nm): 3.105 s, 94%.

Example 35

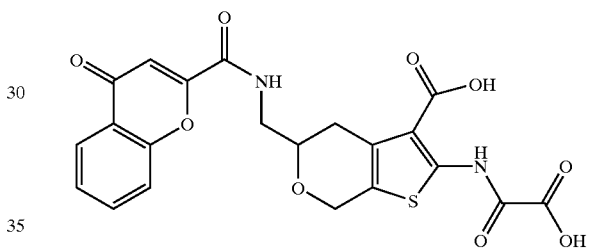

2-(Oxalyl-amino)-5-(((4-oxo-chromene-4H-2-carbonyl)amino)methyl)-4,7-dihydro-5H-thieno[2,3-c]pyran-3-carboxylic Acid $^1$H NMR (400 MHz, DMSO-$d_6$) δ 12.32 (s, 1H), 9.33 (t, J=4 Hz, 1H), 8.05 (d, J=8 Hz, 1H), 7.89 (t, J=8 Hz, 1H), 7.76 (d, J=8 Hz, 1H), 7.53 (t, J=8 Hz, 1H), 6.84 (s, 1H), 4.83 (d, J=15 Hz, 1H), 4.66 (d, J=15 Hz, 1H), 3.89–3.84 (m, 1H), 3.56–3.45 (m, 2H), 2.98 (d, J=18 Hz, 1H), 2.63–2.52 (m, 1H, partially obscured by DMSO); LC/MS [M–H]$^-$: 471.4; HPLC (254.4 nm): 2.886 s, 95%.

Example 36

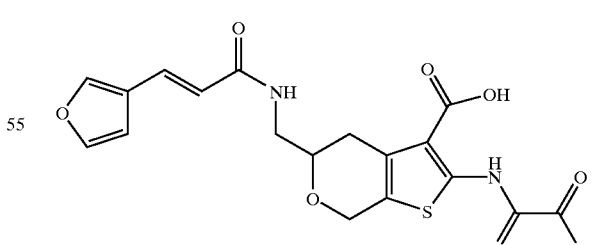

5-((3-Furan-3-yl-acryloylamino)-methyl)-2-(oxalyl-amino)-4,7-dihydro-5H-thieno[2,3-c]pyran-3-carboxylic Acid $^1$H NMR (400 MHz, DMSO-$d_6$) δ 12.32 (s, 1H), 8.20 (t, J=5 Hz, 1H), 7.99 (s, 1H), 7.71 (s, 1H), 7.33 (d, J=15 Hz, 1H), 6.68 (s, 1H), 6.42 (d, J=15 Hz, 1H), 4.81 (d, J=15 Hz, 1H), 4.65 (d, J=15 Hz, 1H), 3.74–3.67 (m, 1H), 3.44–3.34 (m, 2H), 2.91 (d, J=17 Hz, 1H), 2.53 (dd, 1H, partially obscured by DMSO); LC/MS [M−H]⁻: 419.4; HPLC (254.4 nm): 2.822 s, 91%.

Example 37

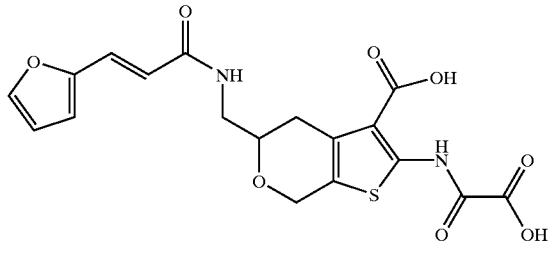

5-((3-Furan-2-yl-acryloylamino)-methyl)-2-(oxalyl-amino)-4,7-dihydro-5H-thieno[2,3-c]pyran-3-carboxylic Acid ¹H NMR (400 MHz, DMSO-d₆) δ 12.32 (s, 1H), 8.37 (t,1H), 7.77 (s, 1H), 7.23 (d, J=15 Hz, 1H), 6.76 (d, J=3 Hz, 1H), 6.57 (dd, J=3 Hz, 2 Hz, 1H), 6.50 (d, J=15 Hz, 1H), 4.81 (d, J=15 Hz, 1H), 4.65 (d, J=15 Hz, 1H), 3.74–3.67 (m, 1H), 3.48–3.32 (m, 2H), 2.91 (d, J=17 Hz, 1H), 2.53 (dd, 1H, partially obscured by DMSO); [M−H]⁻: 419.3; HPLC (254.4 nm): 2.815 s, 86%.

Example 38

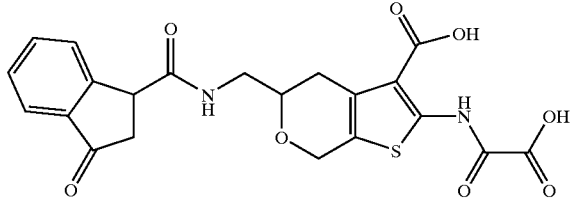

2-(Oxalyl-amino)-5-(((3-oxo-indane-1-carbonyl)amino)methyl)-4,7-dihydro-5H-thieno[2,3-c]pyran-3-carboxylic Acid ¹H NMR (400 MHz, DMSO-d₆) δ 12.33 (s, 1H), 8.81 (bs,1H), 7.74–7.62 (m, 3H), 7.47 (t, J=7 Hz, 1H), 4.83 (d, J=15 Hz, 1H), 4.67 (d, J=15 Hz, 1H), 4.29 (t, J=5 Hz, 1H), 3.41–3.25 (m, 3H), 2.91 (d, J=15 Hz, 1H), 2.77 (d, J=5 Hz, 2H), 2.58–2.51 (m, 1H, partially obscured by DMSO); LC/MS [M−H]⁻: 457.5; HPLC (254.4 nm): 2.634 s, 97%.

By a similar procedure as described in Example 26 the following compound was prepared.

Example 39

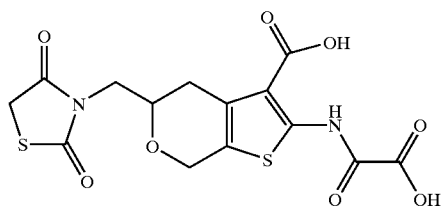

5-(2,4-Dioxo-thiazolidin-3-ylmethyl)-2-(oxalyl-amino)-4,7-dihydro-5H-thieno[2,3-c]pyran-3-carboxylic Acid ¹H NMR (400 MHz, CD₃OD and DMSO-d₆) δ 4.88 (m, 2H), 3.97–3.89 (m, 3H), 3.72–3.69 (m, 2H), 3.08 (m, 1H), 3.02 (m, 1H); MS (ESl (−)): 399; HPLC (254.4nm): 2.67, s, 100%.

By a similar procedure as described in Example 1 the following compounds have been prepared.

Example 40

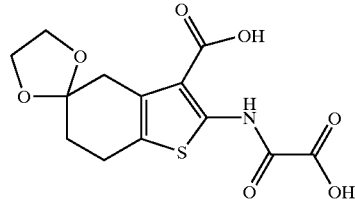

2-(Oxalyl-amino)-5-(2'-spiro[1',3']dioxolane)-6,7-dihydro-4H-benzo[b]thiophen-3-carboxylic Acid M.p.: 232–234° C.; Calculated for C₁₃H₁₃NO₇S, 1×H₂O; C, 45.22%; H, 4.38%; N, 4.06%. Found: C, 45.24%; H, 4.39%; N, 3.98%.

By a similar procedure as described in Example 27 the following compounds have been prepared.

Example 41

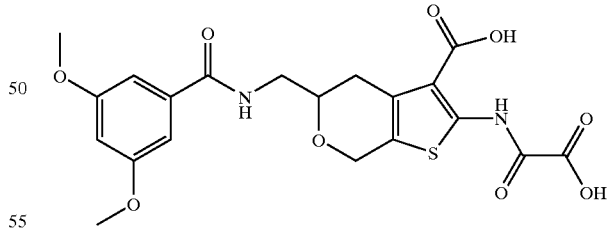

5-((3,5-Dimethoxy-benzoylamino)-methyl)-2-(oxalyl-amino)-4,7-dihydro-5H-thieno[2,3-c]pyran-3-carboxylic Acid ¹H NMR (400 MHz, DMSO-d₆) δ 12.31 (s, 1H), 8.63 (t, J=5 Hz, 1H), 7.02 (s, 2H), 6.62 (s, 1H), 4.80 (d, J=15 Hz, 1H), 4.64 (d, J=15 Hz, 1H), 3.82–3.79 (m, 1H), 3.77 (s, 6H), 3.47–3.45 (m, 2H), 2.94 (d, J=17 Hz, 1H), 2.53 (dd, J=17 Hz, 11Hz, 1H); LC/MS [M−H]⁻: 463.4; HPLC (254.4 nm): 3.161 s, 93%.

Example 42

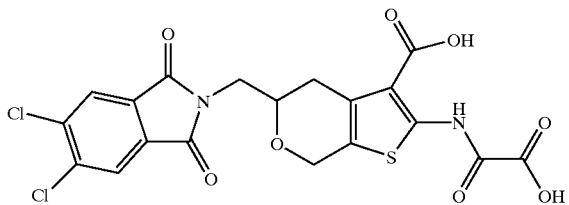

5-(5,6-Dichloro-1,3-dioxo-1,3-dihydro-isoindol-2-ylmethyl)-2-(oxalyl-amino)-4,7-dihydro-5H-thieno[2,3-c]pyran-3-carboxylic Acid To a solution of 2-hydroxymethyl-tetrahydro-pyran-4-one (625 mg, 4.81 mmol) in a mixture of pyridine (778 µl, 9.62 mmol) and chloroform (6.0 ml) at 0° C. under nitrogen was slowly added 4-nitrobenzenesulfonyl chloride (1.60 g, 7.22 mmol). The mixture was allowed to warm to room temperature and stirred for 3 h. Chloroform (30 ml) was added and the solution washed with 2.0 N hydrochloric acid (3×10 ml), 5% NaHCO$_3$ (3×10 ml) and water (3×10 ml). The organic phase was dried (Na$_2$SO$_4$), filtered and the solvent evaporated in. vacuo. The solid residue was purified by column chromatography on silica gel using a gradient of dichloromethane:hexane:ethyl acetate (1:1:0 to 8:0:2) as eluent. Pure fractions were collected and the volatiles were evaporated in vacuo affording 0.98 g (65%) of 4-nitro-benzenesulfonic acid 4-oxo-tetrahydro-pyran-2-ylmethyl ester as a solid.

$^1$H NMR (400 MHz, CDCl$_3$) δ 2.37 (d, 2H, J=7.8 Hz), 2.57 (m, 1H), 3.63 (m, 1H), 3.89 (m, 1H), 4.20–4.26 (m, 3H), 8.14 (dd, 2H, J=0.6 Hz, J=9 Hz), 8.42 (dd, 2H, J=0.6 Hz, J=9 Hz); MS m/z: 315.3 (M+).

4-Nitro-benzenesulfonic acid 4-oxo-tetrahydro-pyran-2-ylmethyl ester (0.5 g, 1.59 mmol), ethylene glycol (986 mg, 15.9 mmol) and p-toluene sulfonic acid (61 mg, 0.32 mmol) were refluxed in benzene (20 ml) for 20 hours. The solvent was removed in vacuo to afford a solid. The solid was dissolved in dichloromethane (30 ml) and successively washed with a saturated aqueous solution of sodium bicarbonate (2×5 ml) and water (2×5 ml). The organic phase was dried (Na$_2$SO$_4$), filtered and the solvent removal in vacuo afforded 582 mg (100%) of 4-nitro-benzenesulfonic acid 1,4,8-trioxa-spiro[4.5]dec-7-ylmethyl ester as a solid.

$^1$H NMR (400 MHz, CDCl$_3$) δ 1.53 –1.73 (m, 4H), 3.54 (m, 1H), 3.8 (m, 2H), 3.96 (m, 4H), 4.15 (m, 2H), 8.12 (dd, 2H, J=1.5 Hz, J=9.0 Hz), 8.40 (dd, 4H, J=1.5 Hz, J=9.0 Hz); MS m/z: 359.3.

3,4-Dichlorophthalimide (90.2 mg, 0.42 mmol) was dissolved in N,N-dimethylformamide (2.0 ml) at room temperature. Sodium hydride (17 mg, 0.42 mmol) was added under nitrogen. 4-Nitro-benzenesulfonic acid 1,4,8-trioxa-spiro[4.5]dec-7-ylmethyl ester (100 mg, 0.28 mmol) was added and the mixture heated to 140° C. for 3 h. After cooling to room temperature the reaction mixture was added to ice water (5 ml) and the mixture extracted with ethyl acetate (3×15 ml). The combined ethyl acetate extracts were washed with 1.0 N hydrochloric acid (2×5 ml), water (2×5 ml), saturated sodium bicarbonate (2×5 ml) and water (2×5 ml). After drying (Na$_2$SO$_4$) followed by filtration, the solvent was removed in vacuo affording 97 mg (94%) of 5,6-dichloro-2-(1,4,8-trioxa-spiro[4.5]dec-7-ylmethyl)-isoindole-1,3-dione as a solid.

$^1$H NMR (400 MHz, CDCl$_3$) δ 1.60 (m, 2H), 1.78 (m, 2H), 3.54 (m, 1H), 3.64 (m, 1H), 3.88 (m, 2H), 3.95 (m, 4H), 7.95 (d, 2H, J=3 Hz); MS m/z: 373.7 (M+).

5,6-Dichloro-2-(1,4,8-trioxa-spiro[4.5]dec-7-ylmethyl)-isoindole-1,3-dione (87 mg, 0.23 mmol) was dissolved in tetrahydrofuran (2.5 ml). 1.0 N hydrochloric acid (1.0 ml) was added to the solution and the mixture was heated at 75° C. for 20 h. The heterogeneous mixture was evaporated to dryness in vacuo and the resulting solid was dissolved in dichloromethane (10 ml) and washed with water (3×2 ml). The organic layer was dried (MgSO$_4$), filtered and the solvent evaporated in vacuo affording 62.1 mg (81%) of 5,6-dichloro-2-(4-oxo-tetrahydro-pyran-2-ylmethyl)-isoindole-1,3-dione as a solid.

$^1$H NMR (400 MHz, CDCl$_3$) δ 2.31–2.41 (m, 2H), 2.48 (t, 1H, J=2.0 Hz), 2.62 (m, 1H), 3.60 (m, 1H), 3.72 (m, 1H), 3.99 (m, 2H), 4.29 (m, 1H), 7.96 (d, 2H, J=2.7 Hz); MS m/z: 331.1 (M+).

5,6-Dichloro-2-(4-oxo-tetrahydro-pyran-2-ylmethyl)-isoindole-1,3-dione (60 mg, 0.18 mmol) was stirred with tert-butyl cyanoacetate (33.5 mg, 0.24 mmol), elemental sulfur (6.44 mg, 0.20 mmol) and morpholine (32.4 µl, 0.37 mmol) in ethanol for 20 h at 50° C. The volatiles were evaporated in vacuo and the resulting solid was dissolved in dichloromethane (30 ml) and washed with water (2×10 ml). The organic phase was dried (MgSO$_4$), filtered and the solvent evaporated in vacuo. The residue (111 mg) was purified by preparative TLC (Kieselgel 60F$_{254}$, 1 mm) using a mixture of hexane and ethyl acetate (1:1) as eluent. Pure compound was obtained after evaporation of the solvent in vacuo affording 28 mg (32%) of 2-amino-5-(5,6-dichloro-1,3-dioxo-1,3-dihydro-isoindol-2-ylmethyl)-4,7-dihydro-5H-thieno[2,3-c]pyran-3-carboxylic acid tert-butyl ester as a solid.

$^1$H NMR (400 MHz, CDCl$_3$) δ 1.54 (s, 9H), 2.90 (m, 1H), 3.35 (m, 2H), 2.60 (m, 2H), 2.90 (m, 1H), 4.62 (m, 1H), 7.95 (d, 2H, J=1.8 Hz); MS m/z: 483.3 (M+), 427 (M-57).

A mixture of 2-amino-5-(5,6-dichloro-1,3-dioxo-1,3-dihydro-isoindol-2-ylmethyl)-4,7-dihydro-5H-thieno[2,3-c]pyran-3-carboxylic acid tert-butyl ester (27.5 mg, 0.057 mmol), imidazol-1-yl-oxo-acetic acid tert-butyl ester (55.8 mg, 0.29 mmol) and triethylamine (16 µl, 0.114 mmol) in tetrahydrofuran (2 ml) was stirred at room temperature for 20 h. The volatiles were evaporated in vacuo and the resulting syrup was dissolved in dichloromethane (15 ml) and washed with water (3×3 ml). The organic phase was dried (MgSO$_4$), filtered and the solvent evaporated in vacuo. The residue (35.7 mg) was purified by preparative TLC (Kieselgel 60F$_{254}$, 0.5 mm) using a mixture of hexane and ethyl acetate (8:2) as eluent. After isolation 8.5 mg (24%) of 2-(tert-butoxyoxalyl-amino)-5-(5,6-dichloro-1,3-dioxo-1,3-dihydro-isoindol-2-ylmethyl)-4,7-dihydro-5H-thieno[2,3-c]pyran-3-carboxylic acid tert-butyl ester was obtained.

$^1$H NMR (400 MHz, CDCl$_3$) δ 1.58 (s, 18H), 2.68 (m, 1H), 2.97–3.02 (m, 1H), 3.82 (m, 1H), 4.63–4.68 (m, 1H), 4.77–4.82 (m, 1H), 7.97 (d, 2H, J=2.1Hz); MS m/z 611.4 (M+).

2-(tert-Butoxyoxalyl-amino)-5-(5,6-dichloro-1,3-dioxo-1,3-dihydro-isoindol-2-ylmethyl)-4,7-dihydro-5H-thieno[2,3-c]pyran-3-carboxylic acid tert-butyl ester (3.5 mg, 5.7× 10-3 mmol) was dissolved in 20% trifluoroacetic acid in dichloromethane (1.0 ml) and stirred for 2 h at room temperature. The volatiles were evaporated in vacuo which afforded 2.7 mg (95%) of the title compound as a solid.

$^1$H NMR (400 MHz, CD$_3$OD) δ 2.66 (m, 1H), 3.10 (m, 1H), 3.80 (m, 1H), 3.98 (m, 2H), 4.66 (m, 1H), 4.74 (m, 1H); MS m/z 498.3 (M-).

The following compounds were prepared in a similar way as described in example 42.

Example 43

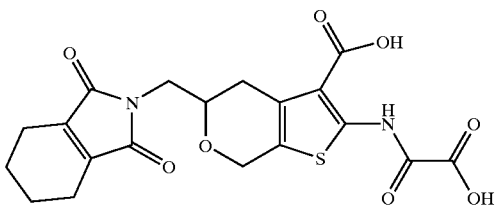

5-(1,3-Dioxo-1,3,4,5,6,7-hexahydro-isoindol-2-ylmethyl)-2-(oxalyl-amino)-4,7dihydro-5H-thieno[2,3-c]pyran-3-carboxylic Acid 2-(1,4,8-Trioxa-spiro[4.5]dec-7-ylmethyl)-4,5,6,7-tetrahydro-isoindole-1,3-dione 73.1 mg (62%) as an oil.

$^1$H NMR (400 MHz, CDCl$_3$) δ 1.42–1.58 (m, 2H), 2.24 (m, 2H), 2.62 (m, 2H), 3.10 (m, 2H), 3.50 (m, 2H), 3.71 (m, 3H), 3.94 (m, 6H), 5.9 (m, 2H).

2-(4-Oxo-tetrahydro-pyran-2-ylmethyl)-4,5,6,7-tetrahydro-isoindole-1,3-dione 50 mg (92%) as a solid.

$^1$H NMR (400 MHz, CDCl$_3$) δ 0.86 (m, 2H), 1.64 (m, 2H), 2.22 (m, 1H), 2.34 (m, 2H), 2.61 (m, 3H), 3.13 (m, 2H), 3.79 (m, 1H), 3.95 (m, 1H), 4.28 (m, 1H), 5.92 (m, 1H).

2-Amino-5-(1,3-dioxo-1,3,4,5,6,7-hexahydro-isoindol-2-ylmethyl)-4,7-dihydro-5H-thieno[2,3-c]pyran-3-carboxylic acid tert-butyl ester was obtained as a solid after purification by preparative TLC (Kieselgel 60F$_{254}$, 1 mm, hexane: ethyl acetate, 1:1) (36 mg, 47%).

$^1$H NMR (400 MHz, CDCl$_3$) δ 1.53 (s, 9H), 2.22 (m, 2H), 2.62 (m, 2H), 2.83 (m, 1H), 3.11 (m, 2H), 3.56 (m, 1H), 3.83 (m, 2H), 4.50 (m, 2H), 5.89 (m, 2H); MS m/z 419.5 (M+), 363.4 (M-57).

2-(tert-Butoxyoxalyl-amino)-5-(1,3-dioxo-1,3,4,5,6,7-hexahydro-isoindol-2-ylmethyl)-4,7-dihydro-5H-thieno[2,3-c]pyran-3-carboxylic acid tert-butyl ester was obtained after purification by preparative TLC (Kieselgel 60F$_{254}$, 0.5 mm, hexane: ethyl acetate, 8:2).

$^1$H NMR (400 MHz, CDCl$_3$) δ 1.60 (s, 18H), 2.24 (m, 2H), 2.92 (m, 3H), 3.14 (m, 2H), 3.90 (m, 2H), 4.11 (m, 1H), 4.63 (m, 1H), 4.78 (m, 1H), 5.91 (m, 2H); MS m/z 545.4 (M-), 489.4 (M-57).

The title compound was obtained as a solid (17.2 mg, quantitative yield).

$^1$H NMR (400 MHz, CD$_3$OD) δ 2.28 (m, 2H), 2.55 (m, 2H), 2.97 (m, 2H), 3.31 (m, 2H), 3.56–3.93 (m, 3H), 4.70 (m, 2H), 5.91 (m, 2H); MS m/z 433.3 (M-).

Example 44

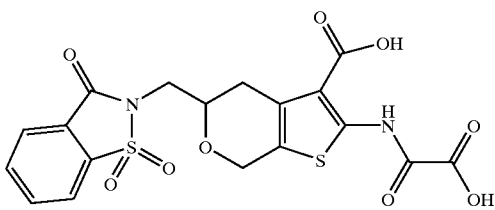

2(Oxalyl-amino)-5-(1,1,3-trioxo-1,3-dihydro-1H-benzo[d]isothiazol-2-yimethyl)-4,7-dihydro-5H-thieno[2,3-c]pyran-3-carboxylic Acid $^1$H NMR (400 MHz, CD$_3$OD) δ 8.09–7.8 (m, 4H), 4.85–4.67 (m, 3H), 4.21–4.12 (m, 1H), 4.02–3.94 (m, 1H), 3.11–3.06 (m, 1H), 2.90–2.80 (m, 1H); MS (ESI (-)): 465; HPLC (254.4 nm): 2.31, s, 99%.

Example 45

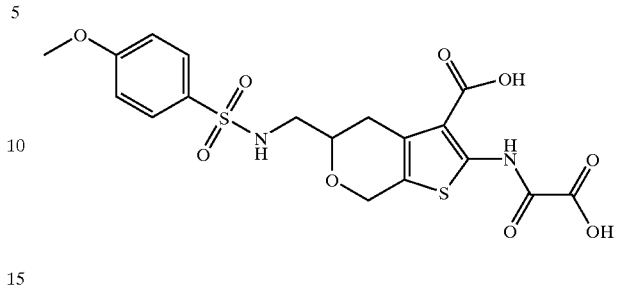

5-[(4-Mehoxy-benzenesulfoylamino)-methyl]-2-(oxalyl-amino)-4,7-dihydro-5H-thieno[2,3-c]pyran-3-carboxylic Acid To a solution of 2-amino-5-aminomethyl-4,7-dihydro-5H-thieno[2,3-c]pyran-3-carboxylic acid tert-butyl ester (101 mg, 0.35 mmol) in dichloromethane (1 ml) was added pyridine (32 µl, 0.39 mmol) and 4-methoxybenzenesulfonyl chloride (82 mg, 0.39 mmol). The reaction mixture was stirred at room temperature for 48 h. The reaction mixture was diluted with dichloromethane (2 ml) and subjected to preparative TLC (1:1 hexanes/ethyl acetate) affording 10 mg, (10%) of 2-amino-5-((4-methoxy-benzenesulfonylamino)-methyl)-4,7-dihydro-5H-thieno[2,3-c]pyran-3-carboxylic acid tert-butyl ester as a solid.

$^1$H NMR (400 MHz, CDCl$_3$) δ 7.82 (d, J=9 Hz, 2H), 6.93 (d, J=9 Hz, 2H), 5.3 (bs, 2H), 4.57 (s, 2H), 3.84 (s, 3H), 3.72 (m, 1H), 3.10–3.06 (m, 1H), 2.95–2.87 (m, 1H), 2.69–2.64 (m, 1H), 2.41–2.32 (m, 1H), 1.47 (s, 9H); MS: APCl (-): 453 [M-H].

To a solution of 2-amino-5-((4-methoxy-benzenesulfonylamino)-methyl)-4,7-dihydro-5H-thieno[2,3-c]pyran-3-carboxylic acid tert-butyl ester (8 mg, 0.017 mmol) in dichloromethane (1 ml) was added triethylamine (7.4 µl, 0.051 mmol), and imidazol-1-yl-oxo-acetic acid tert-butyl ester (10 mg, 0.051 mmol) and stirred at room temperature for 16 h. The volatiles were removed in vacuo and to the residue was added dichloromethane (2 ml). The solution was purified by preparative TLC (10% methanol/90% dichloromethane) affording 10 mg (100%) of 2-(tert-butoxyoxalyl-amino)-5-((4-methoxy-benzenesulfonylamino)-methyl)-4,7-dihydro-5H-thieno[2,3-c]pyran-3-carboxylic acid tert-butyl ester as a solid.

$^1$H NMR (400 MHz, CDCl$_3$) δ 7.83 (d, J=9 Hz, 2H), 6.93 (d, J=9 Hz, 2H), 4.68 (m, 2H), 3.85 (s, 3H), 3.7 (m, 3H), 3.29–3.22 (m, 1H), 2.80–2.75 (m, 1H), 2.53–2.43 (m, 1H), 1.56 (s, 18H); MS:APCl (+): 582.8 [M+H], 527 (-1 tBu).

2-(tert-Butoxyoxalyl-amino)-5-((4-methoxy-benzenesulfonylamino)-methyl)-4,7-dihydro-5H-thieno[2,3-c]pyran-3-carboxylic acid tert-butyl ester (10 mg, 0.017 mmol) was added to a solution of 25% trifluoroacetic acid in dichloromethane (2 ml). The reaction mixture was stirred at room temperature for 2 h, at which time, the solvent was removed in vacuo. The residue was precipitated by addition of diethyl ether and washed two times with diethyl ether affording after drying 2 mg (25%) of the title compound as a solid.

$^1$H NMR (400 MHz, CD$_3$OD) δ 7.78 (d, J=9 Hz, 2H), 7.02 (d, J=9 Hz, 2H), 4.76–4.63 (m, 2H), 3.84 (s, 3H), 3.75 (m, 1H), 3.50–3.47 (m, 2H), 2.89–2.83 (m, 1H), 2.52–2.42 (m, 1H); MS: APCl (+): 471 [M+H].

Example 46

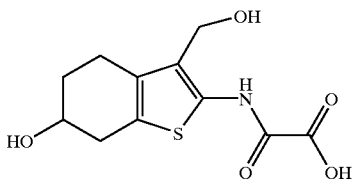

N-(6-Hydroxy-3-hydroxymethyl-4,5,6,7-tetrahydro-benzorbathiophen-2-yl)-oxalamic Acid 2-(Ethoxyoxalyl-amino)-6-(2'-spiro[1',3']dioxolane)-6,7-dihydro-4H-benzo[b]thiophen-3-carboxylic acid tert butyl ester (20 g, 0.05 mol) was dissolved in a (1:4) mixture of trifluoroacetic acid and dichloromethane (200 ml) containing water (1 ml) at 0° C. The reaction mixture was stirred at 0° C. for 1 h and at room temperature for 20 h. The volatiles were evaporated in vacuo and the solid residue was trituated with diethyl ether (2×100 ml) and dried in vacuo affording 15.08 g (100%) of 2-(ethoxyoxalyl-amino)-6-oxo-4,5,6,7-tetrahydro-benzo[b]thiophene-3-carboxylic acid as a solid.

To a mixture of ethanol (50 ml) and dichloromethane (50 ml) was added 2-(ethoxyoxalyl-amino)-6-oxo-4,5,6,7-tetrahydro-benzo[b]thiophene-3-carboxylic acid (2.0 g, 6.43 mmol) followed by sodium borohydride (124 mg, pellets). The resulting mixture was stirred at room temperature for 1 h and an additional sodium borohydride pellet was added. After stirring for an addition 4 h the reaction mixture was quenched by addition of a mixture of water (100 ml) and formic acid (100 ml) at 0° C. The aqueous phase was extracted with ethyl acetate (2×100 ml) and the combined organic phases were washed with brine (100 ml), dried $Na_2SO_4$, filtered and evaporated in vacuo affording 860 mg (43%) of the title compound as a solid. After standing. for 18 h the aqueous phase was filtered and the filter cake was washed with water (2×15 ml), diethyl ether (2×15 ml) and dried in vacuo affording an additional portion 710 mg (48%) of the title compound as a solid.

Calculated for $C_{11}H_{13}N_1O_5S_1$, $0.5 \times H_2O$; C, 47.14%; H, 5.03%; N, 5.00%. Found: C, 47.19%; H, 5.00%; N, 4.94%.

The following compound was prepared in a similar way as described in example 1.

Example 47

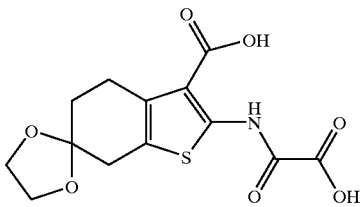

2-(Oxalyl-amino)-6-(2'-spiro[1',3']dioxolane)-6,7-dihydro-4H-benzo[b]thiophen-3-carboxylic Acid M.p.: >250° C.; Calculated for $C_{13}H_{13}NO_7S$; C, 47.70%; H, 4.00%; N, 4.28%. Found: C, 47.93%; H, 4.09%; N, 4.27%.

Example 48 (NNC 52-1122-1A)

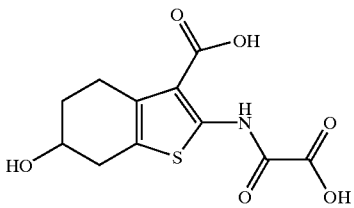

6-Hydroxy-2-(oxalyl-amino)-4,5,6,7-tetrahydro-benzo[b]thiophen-3-carboxylic Acid 2-(Ethoxyoxalyl-amino)-6-(2'-spiro[1',3']dioxolane)-6,7-dihydro-4H-benzo[b]thiophen-3-carboxylic acid ethyl ester (8.7 g, 22.7 mmol) was dissolved in a ice bath cooled mixture of 25% trifluoroacetic acid in dichloromethane (100 ml) and water (0.5 ml) was added. The reaction mixture was stirred at 0° C. for 2 h and at room temperature for 48 h. The volatiles were evaporated in vacuo and the residue dissolved in ethanol (100 ml) and evaporated in vacuo (2 times). The solid residue was washed with diethyl ether (80 ml) and dried in vacuo at 50° C. affording 6.68 g (88%) of 2-(ethoxyoxalyl-amino)-6-oxo-4,5,6,7-tetrahydro-benzo[b] thiophene-3-carboxylic acid ethyl ester as a solid.

To a solution of 2-(ethoxyoxalyl-amino)-6-oxo-4,5,6,7-tetrahydro-benzo[b]thiophene-3-carboxylic acid ethyl ester (2.0 g, 5.89 mmol) in a mixture of dichloromethane (40 ml) and ethanol (40 ml) was added sodium borohydride (64 mg, 1.77 mmol). The reaction mixture was stirred at room temperature for 64 h, additional sodium borohydride (22.3 mg, 0.59 mmol) was added and stirring was continued for an additional 18 h. Two more portions of sodium borohydride (23 mg and 15 mg) was added during the next 6 h of stirring. To the reaction mixture was added ice cooled saturated ammonium chloride (50 ml) and the resulting mixture was extracted with ethyl acetate (3×50 ml). The combined organic extracts were dried ($Na_2SO_4$), filtered and evaporated in vacuo. The residue was dissolved twice in ethyl acetate (100 ml) and evaporated in vacuo. The solid residue was washed with diethyl ether (80 ml) and dried in vacuo at 50° C. affording 1.46 g (75%) of 2-(ethoxyoxalyl-amino)-6-hydroxy-4,5,6,7-tetrahydro-benzo[b]thiophene-3-carboxylic acid ethyl ester as a solid. 1.35 g of this material was subjected to column chromatography (slilca gel) using a mixture of ethyl acetate and heptane (1:1) as eluent. Pure fractions were collected and the solvent evaporated in vacuo affording 0.9 g of pure 2-(ethoxyoxalyl-amino)-hydroxy-4,5,6,7-tetrahydro-benzo[b]thiophene-3-carboxylic acid ethyl ester as a solid.

$^1$H NMR (300 MHz, $CDCl_3$) δ 1.42 (m, 6H), 1.86 (m, 2H), 2.02 (m, 1H), 2.71 (dd, 1H), 2.85 (m, 1H), 3.00 (m, 2H), 4.19 (bs, 1H), 4.40 (dq, 4H), 12.45 (bs, 1H, NHCO).

To a solution of the above di-ethyl ester (0.3 g, 0.88 mmol) in water (10 ml) was added 1 N sodium hydroxide (3.1 ml, 3.08 mmol). The resulting reaction mixture was stirred at room temperature for 16 h. The aqueous phase was acidified by addition of concentrated hydrochloric acid to pH=1 and the reaction mixture was evaporated in vacuo to ½ the original volume. The precipitate was filtered off, washed with a small portion of diethyl ether and dried in vacuo at 50° C. for 16 h affording 130 mg (52%) of the title compound as a solid.

M.p.: amorph; $^1$H NMR (300 MHz, DMSO-$d_6$) δ 1.63 (m, 1H), 1.86 (m, 1H), 2.5 (m, 1H, partly obscured by DMSO), 2.71 (m, 1H), 2.86 (m, 2H), 3.91 (m, 1H), 4.87 (bs, 1H), 12.35 (bs, 1H, NHCO).

The following compound was prepared in a similar way as described in example 27.

Example 49

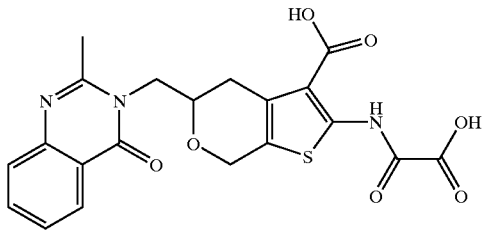

5-(2-Methyl-4-oxo-4H-quinazolin-3-ylmethyl)-2-(oxalyl-amino)-4,7-dihydro-5H-thieno[2,3-c]pyran-3-carboxylic Acid $^1$H NMR (400 MHz, DMSO-d$_6$) δ 12.32 (s, 1H), 8.10 (d, J=8 Hz, 1H), 7.80 (t, J=7 Hz, 1H), 7.59 (d, J=8 Hz, 1H), 7.49 (t, J=7 Hz, 1H), 4.78 (d, J=15 Hz, 1H), 4.53 (d, J=15 Hz, 1H), 4.39 (d, J=15 Hz, 1H), 4.21 (dd, J=15 Hz, 9 Hz, 1H), 4.00–3.94 (m, 1H), 3.05 (d, J=17 Hz, 1H), 2.74–2.65 (m, 1H, partially obscured by neighboring singlet), 2.68 (s, 3H); $^{13}$C NMR (100.6 MHz, DMSO-d$_6$) δ 167.7, 162.8, 161.6, 157.6, 156.1, 148.3, 146.9, 136.0, 130.5, 127.9, 127.8, 126.5, 121.4, 115.0, 74.4, 65.9, 49.8, 31.4, 25.0; [M–H]$^-$: 442.1; HPLC (254.4 nm): 2.631 s, 81%.

Example 50

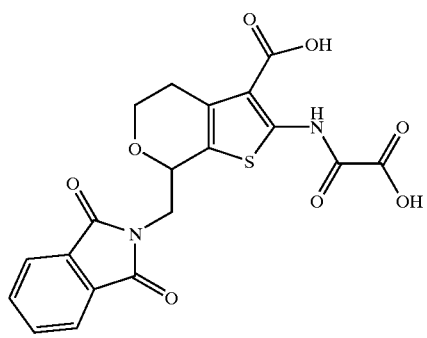

7-(1,3-Dioxo-1,3-dihydro-isoindol-2-ylmethyl)-2-(oxalyl-amino)-4,7-dihydro-5H-thieno[2,3-c]pyran-3-carboxylic Acid Phthalimidoacetaldehyde diethyl acetal (100 g, 0.38 mol) and 1 N hydrochloric acid (600 ml) was mixture was stirred at reflux temperature for 5 min. or until a homogeneous solution is obtained. The reaction mixture was cooled and the precipitate was filtered off and dried in vacuo at 50° C. for 16 h which afforded 63.3 g (88%) of phthalimido-acetaldehyde as a solid.

$^1$H NMR (300 MHz, CDCl$_3$) δ 4.58 (s, 2H), 7.76–7.78(m, 2H), 7.90–7.92 (m, 2H), 9.67 (s, 1H).

To a mixture of phthalimidoacetaldehyde (64 g, 0.34 mol) and trans-1-methoxy-3-(trimethylsilyloxy)-1,3-butadiene (81.5 g, 0.38 mol) in benzene (600 ml) stirred for 15 min. under nitrogen was added dropwise a 45% solution of zinc chloride diethyl ether complex in dichloromethane (55.5 ml, 0.17 mol) at 0° C. The reaction was allowed warm up to room temperature overnight. To the reaction mixture was added water (500 ml) and the resulting mixture was extracted with ethyl acetate (200 ml). The organic extract was washed successively with 1.0 N hydrochloric acid (2×200 ml) and brine (200 ml). The organic phase was dried (Na$_2$SO$_4$), filtered and the solvent evaporated in vacuo which afforded a slowly crystallising oil (98 g). To the solid was added a mixture of ethyl acetate and diethyl ether (400 ml, 1:1) and the resulting precipitate was filtered off, washed with a small portion of diethyl ether and dried at 50° C. for 1 h affording 59.8 g (69%) of 2-(4-oxo-3,4-dihydro-2H-pyran-2-ylmethyl)-isoindole-1,3-dione as a solid. The filtrate was evaporated in vacuo and the residue purified by column chromatography on silica gel (1 L) using a mixture of ethyl acetate and heptane (1:2) as eluent. Pure fractions were collected and the solvent evaporated in vacuo to almost dryness, the solid was filtered off and dried in vacuo at 50° C. for 16 h affording an additional 15 g (17%) of 2-(4-oxo-3,4-dihydro-2H-pyran-2-ylmethyl)-isoindole-1,3-dione as a solid.

$^1$H NMR (300 MHz, CDCl$_3$) δ 2.61 (d, 2H), 3.85 (dd, 1H), 4.18 (dd, 1H), 4.76 (m, 1H), 5.43 (d, 1H), 7.28 (d, 1H), 7.69–7.77 (m, 2H), 7.84–7.88 (m, 2H).

2-(4-Oxo-3,4-dihydro-2H-pyran-2-ylmethyl)-isoindole-1,3-dione (13 g, 0.051 mol) was dissolved in ethyl acetate (250 ml), and placed in a Parr bottle. 10% Pd/C (1.5 g) was carefully added and the mixture was shaken under a pressure of 30 psi of hydrogen for 6.5 h (Parr apparatus). Filtration followed by evaporation of the ethyl acetate in vacuo afforded a crude 11.5 g of 2-(4-oxo-tetrahydro-pyran-2-ylmethyl)-isoindole-1,3-dione pure enough for the next step. Analytical pure compound could be obtained by purification of a small sample (250 mg) by column chromatography on silica gel, utilising a mixture of hexane/ethyl acetate as a gradient (from 100/0 to 50/50). Pure fractions were collected and the solvent evaporated in vacuo affording 142 mg (55% of 2-(4-oxo-tetrahydro-pyran-2-ylmethyl)-isoindole-1,3-dione as a solid.

$^1$H NMR (400 MHz, CDCl$_3$) δ 2.30–2.68 (m, 4H), 3.62 (m, 1H), 3.74(m, 1H), 4.00 (m, 2H), 7.75 (m, 2H), 7.88 (m, 2H).

To a mixture of 2-(4-oxo-tetrahydro-pyran-2-ylmethyl)-isoindole-1,3-dione (18.7 g, 0.072 mol), tert-butyl cyanoacetate (11.2 g, 0.079 mol) and elemental sulfur (2.5 g, 0.079 mol) in ethanol was added morpholin (20 ml) and the resulting mixture was stirred at 50° C. for 3 h. The cooled reaction mixture was filtered and the volatiles were evaporated in vacuo. To the residue was added water (200 ml) and diethyl ether 100 ml. A precipitate was filtered off and dried in vacuo at 50° C. affording 9.1 g (30% of 2-amino-5-(1,3-dioxo-1,3-dihydro-isoindol-2-ylmethyl)-4,7-dihydro-5H-thieno[2,3-c]pyran-3-carboxylic acid tert-butyl ester as a solid.

The filtrate was extracted with ethyl acetate (2×150 ml) and washed with brine (100 ml), dried (Na$_2$SO$_4$), filtered and the solvent evaporated in vacuo. The residue (20 g) was purified by column chromatography on silica gel (1 L) using as mixture of hexane and ethyl acetate (1:2) as eluent. Pure fractions were collected and the solvent evaporated in vacuo. The residue was washed with diethyl ether and the solid was filtered off and dried in vacuo at 50° C. affording an additional 2.2 g (7%) of 2-amino-5-(1,3-dioxo-1,3-dihydro-isoindol-2-ylmethyl)-4,7-dihydro-5H-thieno[2,3-c]pyran-3-carboxylic acid tert-butyl ester as a solid.

The filtrate was evaporated in vacuo affording almost pure 10.2 g (34%) of 2-amino-7-(1,3-dioxo-1,3-dihydro-isoindol- 2-ylmethyl)-4,7-dihydro-5H-thieno[2,3-c]pyran-3-carboxylic acid tert-butyl ester as an oil.

2-Amino-5-(1,3-dioxo-1,3-dihydro-isoindol-2-ylmethyl)-4,7-dihydro-5H-thieno[2,3-c]pyran-3-carboxylic Acid tert-Butyl Ester $^1$H NMR (300 MHz, CDCl$_3$) δ 1.50 (s, 9H), 2.54–2.63 (m, 1H), 2.84–2.90 (m, 1H) 3.79 (q, 1H), 3.96–4.04 (m, 2H), 4.48–4.62 (m, 2H), 5.91 (bs, 2H, NH), 7.7 (m, 2H), 7.84 (m, 2H).

2-Amino-7-(1,3-dioxo-1,3-dihydro-isoindol-2-ylmethyl)-4,7-dihydro-5H-thieno[2,3-c]pyran-3-carboxylic Acid tert-Butyl Ester $^1$H NMR (300 MHz, CDCl$_3$) δ 1.50 (s, 9H), 2.71–2.90 (m, 2H), 3.67–3.77 (m, 2H), 4.02–4.15 (m, 2H), 4.90 (m, 1H), 6.04 (bs, 2H, NH), 7.70 (m, 2H), 7.84 (m, 2H).

A mixture of 2-amino-7-(1,3-dioxo-1,3-dihydro-isoindol-2-ylmethyl)-4,7-dihydro-5H-thieno[2,3-c]pyran-3-carboxylic acid tert-butyl ester (10.2 g, 0.25 mol), imidazol-1yl-oxo-acetic acid tert-butyl ester (7.2 g, 0.037 mol) in dry tetrahydrofuran (150 ml) was stirred at room temperature for 4 h. An additional portion of imidazol-1-yl-oxo-acetic acid tert-butyl ester (2.0 g, 0.01 mol) was added and the resulting mixture was stirred for 16 h at room temperature. The precipitate was filtered off and washed with small portions of diethyl ether and dried in vacuo affording 3.5 g (26%) of 2-(tert-butoxyoxalyl-amino)-7-(1,3-dioxo-1,3-dihydro-isoindol-2-ylmethyl)-4,7-dihydro-5H-thieno[2,3-c]pyran-3-carboxylic acid tert-butyl ester as a solid.

The filtrate was evaporated in vacuo and to the residue was added water (100 ml) and ethyl acetate (100 ml). The precipitate was filtered off and dried in vacuo at 50° C. affording an additional 0.8 g (6%) of 2-(tert-butoxyoxalyl-amino)-7-(1,3-dioxo-1,3-dihydro-isoindol-2-ylmethyl)-4,7-dihydro-5H-thieno[2,3-c]pyran-3-carboxylic acid tert-butyl ester as a solid. $^1$H NMR (300 MHz, CDCl$_3$) δ 1.60 (s, 9H), 1.62 (s, 9H), 2.79–2.97 (m, 2H), 3.73 (m, 1H), 3.83–3.88 (dd, 1H), 4.07–4.16 (m, 2H), 5.09 (m, 1H), 7.71 (m, 2H), 7.85 (m, 2H), 12.55 (bs, 1H, NHCO).

The above 2-(tert-butoxyoxalyl-amino)-7-(1,3-dihydro-isoindol-2-ylmethyl)-4,7-dihydro-5H-thieno[2,3-c]pyran-3-carboxylic acid tert-butyl ester (0.8 g, 1.47 mmol) was added to a solution of 25% trifluoroacetic acid in dichloromethane (30 ml). The reaction mixture was stirred at room temperature for 6 h, at which time, the solvent was removed in vacuo. The residue was precipitated by addition of diethyl ether, filtered off and dried in vacuo at 50° C. affording 0.5 g (79%) of the title compound as a solid.

M.p.:>250° C.; Calculated for C$_{19}$H$_{14}$N$_2$O$_8$S, 0.5×H$_2$O; C, 51.94%; H, 3.44%; N. 6.38%. Found: C, 52.02%; H, 3.37%; N, 6.48%.

Example 51

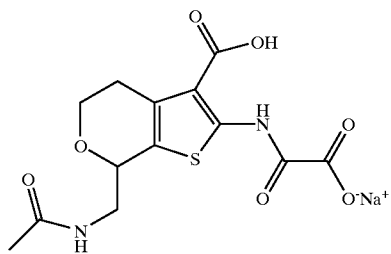

7-(Acetylamino-methyl)-2-(oxalyl-amino)-4,7-dihydro-5H-thieno[2,3-c]pyran-3-carboxylic Acid, Mono Sodium Salt To a mixture of 2-amino-7-(1,3-dioxo-1,3-dihydro-isoindol-2-ylmethyl)-4,7-dihydro-5H-thieno[2,3-c]pyran-3-carboxylic acid tert-butyl ester (6.0 g, 0.014 mol) in ethanol (100 ml) was added hydrazine hydrate (1.4 ml, 0.028 mol). The reaction mixture was heated at reflux for 1 h, cooled and the precipitate filtered off. The filtrate was evaporated in vacuo and to theresidue was added water (100 ml) and the resulting mixture was extracted with diethyl ether (2×100 ml). The combined organic extracts were washed with brine (100 ml), dried (Na$_2$SO$_4$), filtered and the solvent evaporated in vacuo affording 2.9 g (71%) of 2-amino-7-aminomethyl-4,7-dihydro-5H-thieno[2,3-c]pyran-3-carboxylic acid tert-butyl ester as an oil.

$^1$H NMR (300 MHz, CDCl$_3$) δ 1.55 (s, 9H), 2.70–2.97 (m, 4H), 3.69–3.78 (m, 1H), 4.13 (m, 1H), 4.50 (m, 1H), 6.09 (bs, 2H, thiophen-NH$_2$).

To a ice water cooled solution of the above 2-amino-7-aminomethyl-4,7-dihydro-5H-thieno[2,3-c]pyran-3-carboxylic acid tert-butyl ester (1.5 g, 5.27 mmol) and triethylamine (1.5 ml) in dichloromethane (50 ml) was added dropwise acetylchloride (0.46 g, 5.80 mmol). The reaction mixture was allowed to reach room temperature and stirred for an additional 0.5 h. The reaction mixture was washed with water (2×25 ml), dried (Na$_2$SO$_4$), filtered and the solvent evaporated in vacuo. The residue was purified by column chromatography on silicagel (1 L) using first ethyl acetate and later on a mixture of ethyl acetate and ethanol (20:1) as eluents. Pure fractions were collected and the solvent evaporated in vacuo affording 0.3 g (17%) of 7-(acetylamino-methyl)-2-amino-4,7-dihydro-5H-thieno[2,3-c]pyran-3-carboxylic acid tert-butyl ester as a solid.

$^1$H NMR (300 MHz, CDCl$_3$) δ 1.56 (s, 9H), 1.99 (s, 3H), 2.77 (m, 2H), 3.19 (m, 1H), 3.67–3.79 (m, 2H), 4.09–4.16 (m, 1H), 4.63 (m, 1H), 5.91 (bs, 1H), 6.10 (bs, 2H).

To a mixture of the above 7-(acetylamino-methyl)-2-amino-4,7-dihydro-5H-thieno[2,3-c]pyran-3-carboxylic acid tert-butyl ester (0.3 g, 0.92 mmol) in dry tetrahydrofuran (40 ml) was added dropwise a mixture of imidazol-1-yl-oxo-acetic acid tert-butyl ester (0.22 g, 1.10 mmol) in dry tetrahydrofuran (5 ml). The mixture was stirred at room temperature for 3 h. The volatiles were evaporated in vacuo and the residue was dissolved in ethyl acetate (100 ml) and washed with water (50 ml) and brine (50 ml). The organic phase was dried (Na$_2$SO$_4$), filtered and evaporated in vacuo. The residue (0.4 g) was stirred with a mixture of diisopropyl ether (5 ml) and diethyl ether (5 ml). The precipitate was filtered off and the filtrate evaporated in vacuo affording 0.25 g (60%) of 7-(acetylaminomethyl)-2-(tert-butoxyoxalyl-amino)-4,7-dihydro-5H-thieno[2,3-c]pyran-3-carboxylic acid tert-butyl ester as an oil.

$^1$H NMR (300 MHz, CDCl$_3$) δ 1.64 (s, 9H), 1.65 (s, 9H), 2.02 (s, 3H), 2.87 (m, 2H), 3.29 (m, 1H), 3.74 (m, 1H), 3.89 (ddd, 1H), 4.18 (m, 1H), 4.78 (m, 1H), 5.93 (bs, 1H, NHCOMe), 12.5 (s, 1H, NHCOCOOH).

The above 7-(acetylamino-methyl)-2-(tert-butoxyoxalyl-amino)-4,7-dihydro-5H-thieno[2,3-c]pyran-3-carboxylic acid tert-butyl ester (0.2 9, 0.44 mmol) was added to a solution of 25% trifluoroacetic acid in dichloromethane (20 ml). The reaction mixture was stirred at room temperature for 4 h, at which time, the solvent was removed in vacuo. The residue was precipitated by addition of diethyl ether, filtered off and dried in vacuo at 50° C. affording 0.11 g (73%) of the title compound as a solid.

Calculated for C$_{13}$H$_{13}$N$_2$O$_7$S$_1$Na$_1$, 0.5×H$_2$O; C, 41.83%; H, 3.78%; N. 7.50%. Found: C, 42.18%; H, 4.08%; N, 7.61%.

$^1$H NMR (300 MHz, DMSO-d$_6$) δ 1.87 (s, 3H), 2.82 (bs, 2H), 3.19 (m, 1H), 3.51 (m, 1H), 3.67 (m, 1H), 4.07 (m, 1H), 4.69 (m, 1H), 8.14 (t, 1H, NHCOMe), 12.3 (s, 1H, NHCOCOOH).

Example 52

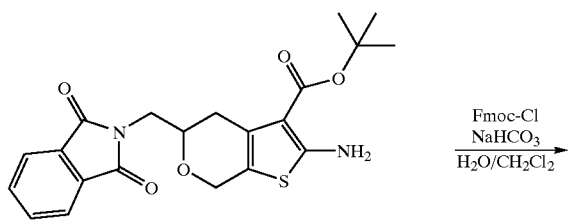

Fmoc-Cl
NaHCO₃
———————→
H₂O/CH₂Cl₂

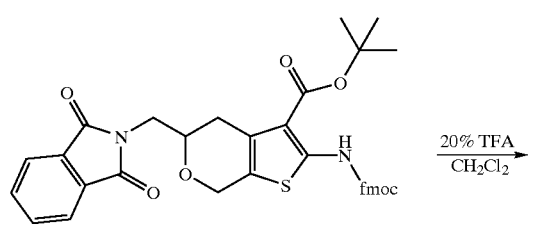

20% TFA
————→
CH₂Cl₂

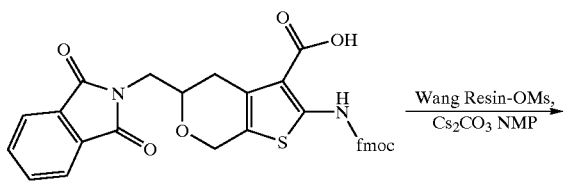

Wang Resin-OMs,
——————————→
Cs₂CO₃ NMP

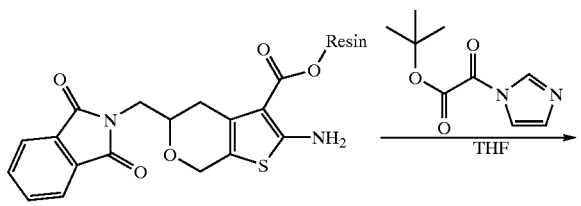

——→
THF

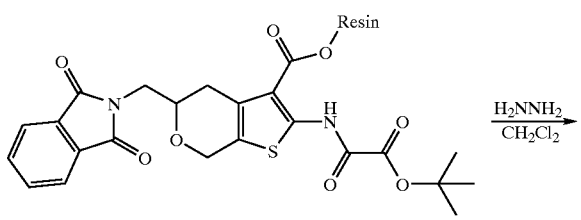

H₂NNH₂
————→
CH₂Cl₂

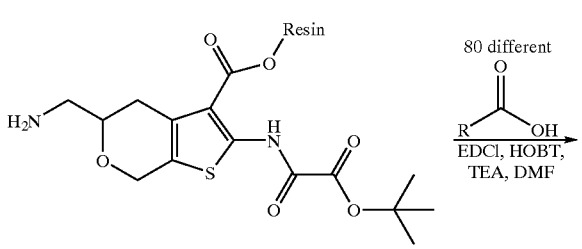

80 different
———————→
EDCl, HOBT,
TEA, DMF

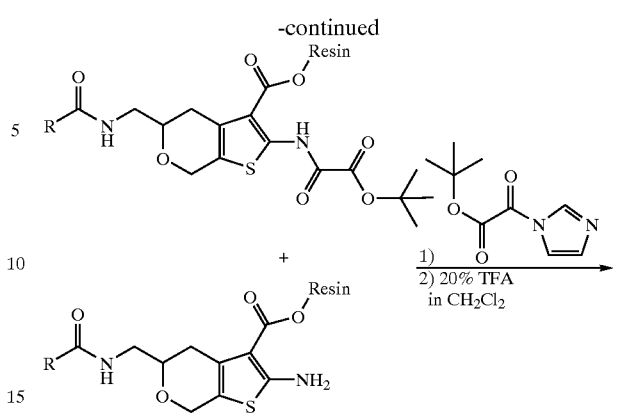

1)
2) 20% TFA
———————→
in CH₂Cl₂

To 2-amino-5-(1,3-dioxo-1,3-dihydro-isoindol-2-ylmethyl)-4,7-dihydro-5H-thieno[2,3-c]pyran-3-carboxylic acid tert-butyl ester (4.5 g, 0.011 mole) dissolved in dichloromethane (30 ml), was added sodium bicarbonate (1.0 g, 0.011 mole) dissolved in water (16 ml). The reaction mixture was cooled to 0° C. and 9-fluorenylmethyl chloroformate (3.0 g, 0.012 mole) was added. After stirring for 5 minutes the reaction mixture was warmed to room temperature and stirred vigorously for 16 h. The organic layer was separated and washed with brine (10 ml). The aqueous phase was extracted with dichloromethane (2×20 ml) and the combined organic phases were dried (MgSO₄), filtered and evaporated in vacuo to give an orange solid which was purified by flash chromatography using dichloromethane as eluent. Pure fractions were collected and evaporated in vacuo affording 5.6 g (81%) of 5-(1,3-dioxo- 1,3-dihydro-isoindol-2-ylmethyl)-2-(9H-fluoren-9-ylmethoxycarbonylamino)-4,7-dihydro-5H-thieno[2,3-c]pyran-3-carboxylic acid tert-butyl ester as a solid.

¹H NMR (400 MHz, CDCl₃) δ 10.60 (bs, 1H), 7.87–7.84 (m, 2H), 7.75 (d, J=8 Hz, 2H), 7.73–7.70 (m, 2H), 7.60 (d, J=8 Hz, 2H), 7.39 (t, J=8 Hz, 2H), 7.30 (t, J=8 Hz, 2H), 4.74 (d, J=14 Hz, 1H), 4.62 (d, J=14 Hz, 1H), 4.48 (d, J=7 Hz, 2H), 4.27 (t, J=7 Hz, 1H), 4.05–4.00 (m, 2H), 3.86–3.80 (m, 1H), 2.92 (d, J=17 Hz, 1H), 2.64 (dd, J=17, 9 Hz, 1H), 1.52 (s, 9H); LC/MS [M+H]⁺: 637.49.

The above F-moc protected thieno[2,3-c]pyran (5.5 g, 8.6 mmole) was added at 0° C. to a solution of 20% trifluoroacetic acid in dichloromethane (30 ml). The reaction was stirred for 4 h at room temperature. The volatiles were evaporated in vacuo and the residue was precipitated with diethyl ether, filtered off and dried, which afforded 4.2 g (85%) of 5-(1,3-dioxo-1,3-dihydro-isoindol-2-ylmethyl)-2-

(9H-fluoren-9-ylmethoxy-carbonylamino)-4,7-dihydro-5H-thieno[2,3-c]pyran-3-carboxylic acid as a solid.

$^1$H NMR (400 MHz, DMSO-d$_6$) δ 10.22 (br s, 1H), 7.88 (d, J=5 Hz, 2H), 7.88–7.82 (m, 4H), 7.66 (d, J=5 Hz, 2H), 7.40 (t, J=5 Hz, 2H), 7.32 (t, J=5 Hz, 2H), 4.68–4.48 (m, 4H), 4.34 (t, J=5 Hz, 1H), 3.90–3.81 (m, 2H), 3.72–3.67 (m, 1H), 2.87 (m, 1H), 2.51 (m, 1H).

To Wang-Resin (3.75 g, 4.5 mmol) was added dichloromethane (50 ml) and the mixture was cooled to 0° C. under nitrogen. Diisopropylethylamine (25 ml) was added followed by methanesulfonyl chloride (2.25 ml, 29 mmol). The reaction was stirred at 0° C. for 0.5 h, then at room temperature for another 0.5 h. The resin was filtered off and washed with dichloromethane (2×30 ml), N-methylpyrrolidinone (20 ml) and again with dichloromethane (2×30 ml). The Wang-resin methansulfonyl ester was dried in vacuo for 2 h and used directly in the next step.

To the above Wang-Resin methansulfonyl ester and 5-(1,3-dioxo-1,3-dihydro-isoindol-2-ylmethyl)-2-(9H-fluoren-9-ylmethoxy-carbonylamino)-4,7-dihydro-5H-thieno[2,3]pyran-3-carboxylic acid (4.85 g, 8.4 mmol) was added N-methylpyrrolidinone (45 ml). Cesium carbonate (2.2 g, 6.7 mmol) was added and the reaction stirred under nitrogen for 16 h and then at 80° C. for 36 h. The mixture was cooled to room temperature, the resin filtered off, washed with water, methanol, and dichloromethane repeatedly and dried in vacuo for 2 h affording 5-(1,3-dioxo-1,3-dihydro-isoindol-2-ylmethyl)-2-(9H-fluoren-9-ylmethoxy-carbonylamino)-4,7-dihydro-5H-thieno[2,3-c]pyran-3-carboxylic acid Wang-Resin ester.

The above Wang-Resin ester (4.85 g) was stirred in a solution of 20% piperidine in tetrahydrofuran (20 ml) for 45 minutes. The resin was then filtered off, washed with tetrahydrofuran (2×20 ml), methanol (2×20 ml), and dichloromethane (3×20 ml) and dried in vacuo for 3 h affording 2-amino-5-(1,3-dioxo-1,3-dihydro-isoindol-2-ylmethyl)-4,7-dihydro-5H-thieno[2,3-c]pyran-3-carboxylic acid Wang-Resin ester.

The above Wang-Resin ester (4.85 g) was suspended in a mixture of dichloromethane (50 ml) and triethylamine (3.0 ml). Imidazol-1-yl-oxo-acetic acid tert-butyl ester (4.2 g, 0.021 mol) was added under nitrogen and the reaction stirred at room temperature for 16 h. The resin was filtered off, washed with methanol (30 ml) then dichloromethane (30 ml) and this process was repeated twice. The resin was dried in vacuo for several hours affording 2-(tert-butoxyoxalyl-amino)-5-(1,3-dioxo-1,3-dihydro-isoindol-2-ylmethyl)-4,7-dihydro-5H-thieno[2,3-c]pyran-3-carboxylic acid Wang Resin ester.

A small sample of the above Wang-Resin ester was treated with 20% trifluoroacetic acid in dichloromethane (3 ml) for 1 h. The resin was filtered off and the filtrate concentrated in vacuo. The residue was evaporated twice from dichloromethane yielding 30 mg of a solid, which had $^1$H NMR and MS consistent with the compound synthesized in example 26. The loading of the Wang-Resin was determined to be 0.6 mmol/g.

The above Wang Resin ester (3.0 g, 1.8 mmol) was suspended in dichloromethane (25 ml). Hydrazine (0.14 ml, 4.5 mmol) was added and the reaction stirred under nitrogen at room temperature for 24 h. The resin was filtered off and washed multiple times, alternating between methanol and dichloromethane. The filtrate was collected and concentrated to yield 260 mg of a solid. The reaction was determined to be incomplete by analysis of the byproduct, at which time the resin was suspended again in dichloromethane (15 ml) and treated with hydrazine (50 μl) for an additional 16 h. The resin was filtered off and washed as before, yielding an additional 30 mg of byproduct from the filtrate. At this point the reaction was judged to be complete and the resin was dried in vacuo for 3 h, yielding 2.67 g of 5-aminomethyl-2-(tert-butoxyoxalyl-amino)-4,7-dihydro-5H-thieno[2,3-c]pyran-3-carboxylic acid Wang-Resin ester. The resin gave a positive ninhydrin test for amines.

The above Wang Resin ester (2.67 g) was suspended in a mixture of tetrahydrofuran and dichloromethane (1:1, 90 ml) and distributed to the OntoBlock (80 wells, 0.02 mmol per well). The blocks were drained. Meanwhile, 80 carboxylic acids were weighed into individual vials (0.044 mmol per vial). A solution of 1-(3-dimethylaminopropyl)-3-ethylcarbodiimide hydrochloride (0.85 g, 4.4 mmol), 1-hydroxy-benzotriazole hydrate (0.6 g, 4.4 mmol), and triethylamine (1.1 ml; 8.0 mmol) was prepared in N,N-dimethylformamide (100 ml). This solution was added to each vial (1 ml per vial) and then the contents of each vial were transferred to a well of the OntoBlock (occasionally the vials were sonicated to achieve full solubility). The blocks were then shooked for 2 days. After this time the blocks were drained and washed using methanol and dichloromethane. The blocks were then placed in a vacuum dessicator for 2 h, after which 1 ml of a solution of imidazol-1-yl-oxo-acetic acid tert-butyl ester (0.2 M in dichloromethane) was added to each well. The blocks were then shooked for 16 h. Again the blocks were washed using the above method. After washing, 1 ml of a solution of 20% trifluoroacetic acid in dichloromethane was added to each well and allowed to sit for 45 minutes. The block was drained and the filtrates collected in a microtiter plate. The wells were treated with an additional 0.5 ml solution of 20% trifluoroacetic acid in dichloromethane and the filtrate again collected. The volatiles were evaporated in vacuo, yielding 80 compounds as solids in the microtiter plate. The plate was analyzed by Mass Spectrometry in which 66 of the wells showed the expected product as the molecular ion. The percentage means the area of the peak of the HPLC at 220 nm.

$X_1$ is point of attachment.

| R | Formula | Mw | LC/MS |
|---|---|---|---|
| 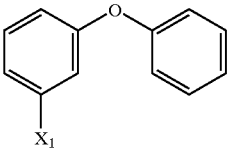 | $C_{24}H_{20}N_2O_8S$ | 496,50 | 495 (M − H, 21%) |

-continued
| R | Formula | Mw | LC/MS |
|---|---|---|---|
| 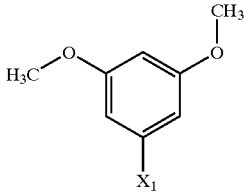 | C$_{20}$H$_{20}$N$_2$O$_9$S | 464,45 | 463 (M − H, 30%) |
| 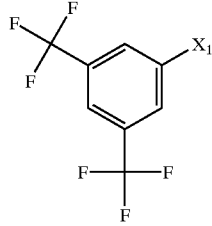 | C20H14F6N2O7S | 540,40 | 539 (M − H, 16%) |
| 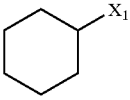 | C18H22N2O7S | 410,45 | 409 (M − H, 33%) |
| 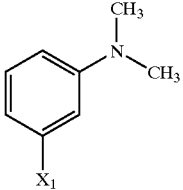 | C20H21N3O7S | 447,47 | 446 (M − H, 39%) |
| 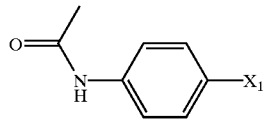 | C20H19N3O8S | 461,45 | 460 (M − H, 38%) |
| 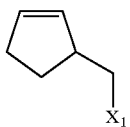 | C18H20N2O7S | 408,43 | 407 (M − H, 40%) |
| 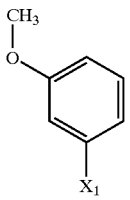 | C19H18N2O8S | 434,43 | 433 (M − H, 49%) |
| 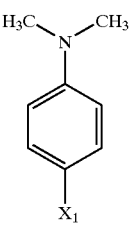 | C20H21N3O7S | 447,47 | 446 (M − H, 38%) |

-continued
| R | Formula | Mw | LC/MS |
|---|---|---|---|
| 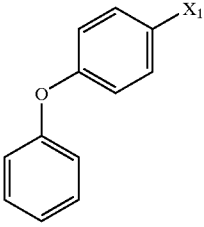 | C24H20N2O8S | 496,50 | 495 (M − H, 47%) |
| 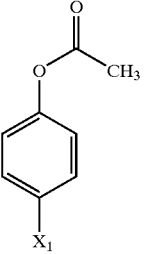 | C20H18N2O9S | 462,44 | 444 (M − H2O) |
| 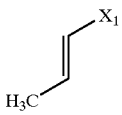 | C15H16N2O7S | 368,37 | 367 (M − H, 33%) |
| 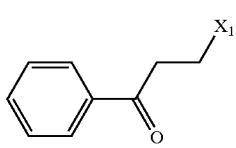 | C21H20N2O8S | 460,47 | 459 (M − H, 31%) |
| 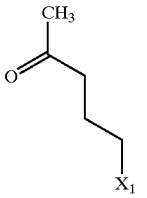 | C17H20N2O8S | 412,42 | 411 (M − H, 30%) |
| 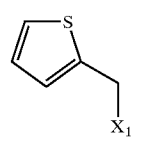 | C17H16N2O7S2 | 424,45 | 423 (M − H, 16%) |
| 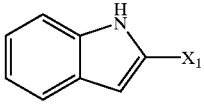 | C20H17N3O7S | 443,44 | 557 (M + TFA, 36%) |
| 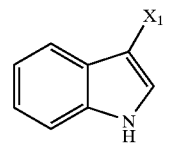 | C20H17N3O7S | 443,44 | 442 (M − H, 37%) |
| 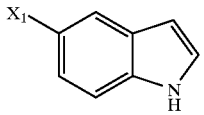 | C20H17N3O7S | 443,44 | 425 (M − H2O, 23%) |

-continued
| R | Formula | Mw | LC/MS |
|---|---|---|---|
| 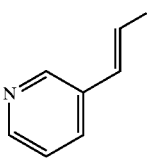 | C19H17N3O7S | 431,43 | 430 (M − H, 48%) |
| 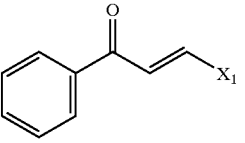 | C21H18N2O8S | 458,45 | 414 (M − CO$_2$, 24%) |
| 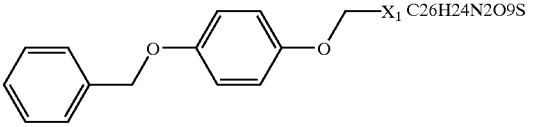 | C26H24N2O9S | 540,55 | 539 (M − H, 17%) |
| 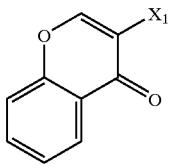 | C21H16N2O9S | 472,43 | 471 (M − H, 35%) |
| 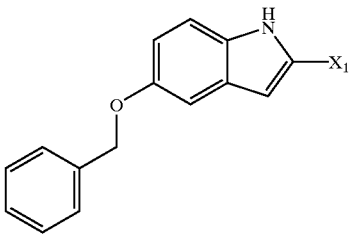 | C27H23N3O8S | 549,56 | 663 (M + TFA, 36%) |
| 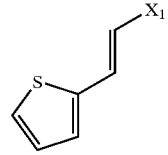 | C18H16N2O7S2 | 436,47 | 437 (M + H, 45%) |
| 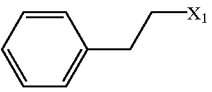 | C20H20N2O7S | 432,46 | 431 (M − H, 20%) |
| 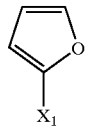 | C16H14N2O8S | 394,36 | 393 (M − H, 43%) |
| 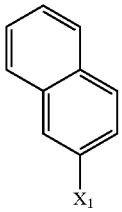 | C22H18N2O7S | 454,46 | 453 (M − H, 42%) |

-continued

| R | Formula | Mw | LC/MS |
|---|---------|----|----|
| phenoxymethyl | C19H18N2O8S | 434,43 | 433 (M − H, 22%) |
| benzyl | C19H18N2O7S | 418,43 | 417 (M − H, 28%) |
| 3,4-dimethoxybenzyl | C21H22N2O9S | 478,48 | 477 (M − H, 25%) |
| 4-ethoxybenzyl | C21H22N2O8S | 462,48 | 461 (M − H, 33%) |
| styryl | C20H18N2O7S | 430,44 | 429 (M − H, 57%) |
| 3,5-dimethoxystyryl | C22H22N2O9S | 490,49 | 446 (M − $CO_2$, 42%) |
| 5-oxopyrrolidin-2-yl | C16H17N3O8S | 411,39 | 410 (M − H, 14%) |
| furan-3-yl | C16H14N2O8S | 394,36 | 393 (M − H, 39%) |
| thiophen-2-yl | C16H14N2O7S2 | 410,43 | 409 (M − H, 51%) |
| phthalimidomethyl | C21H17N3O9S | 487,45 | 486 (M − H, 17%) |

-continued
| R | Formula | Mw | LC/MS |
|---|---|---|---|
|  | C16H14N4O7S | 406,38 | 405 (M − H, 17%) |
|  | C17H15N3O8S | 421,39 | 420 (M − H, 18%) |
|  | C17H15N3O7S | 405,39 | 404 (M − H, 43%) |
|  | C17H15N3O7S | 405,39 | 404 (M − H, 41%) |
|  | C21H16F6N2O7S | 554,43 | 553 (M − H, 18%) |
|  | C20H20N2O9S2 | 496,52 | 495 (M − H, 51%) |
|  | C20H16F2N2O7S | 466,42 | 465 (M − H, 43%) |
|  | C16H16N2O8S | 396,38 | 510 (M + TFA, 21%) |
|  | C22H19N3O9S | 501,48 | 500 (M − H, 23%) |

-continued

| R | Formula | Mw | LC/MS |
|---|---|---|---|
| (CH3-CO-CH2CH2CH2-X1) | C18H22N2O8S | 426,45 | 425 (M − H, 24%) |
| (4-(N,N-dimethylamino)benzyl-X1) | C21H23N3O7S | 461,50 | 460 (M − H, 23%) |
| (benzo[1,3]dioxol-5-yl-X1) | C19H16N2O9S | 448,41 | 447 (M − H, 42%) |
| (N-acetyl-phenylalanyl-X1) | C22H23N3O8S | 489,51 | 488 (M − H, 33%) |
| (2-acetoxyphenyl-X1) | C20H18N2O9S | 462,44 | 418 (M − CO2, 27%) |
| (phenylacetyl-X1) | C20H18N2O8S | 446,44 | 445 (M − H, 16%) |
| (benzoylaminomethyl-X1) | C20H19N3O8S | 461,45 | 460 (M − H, 21%) |
| (CH3-CO-CH2CH2-X1) | C16H18N2O8S | 398,39 | 380 (M − H2O, 25%) |
| (2-furyl-CH=CH-X1) | C18H16N2O8S | 420,40 | 421 (M + H, 39%) |

-continued

| R | Formula | Mw | LC/MS |
|---|---|---|---|
| (acetamidomethyl) | C15H17N3O8S | 399,38 | 398 (M − H, 19%) |
| (phenylthiomethyl) | C19H18N2O7S2 | 450,49 | 449 (M − H, 23%) |
| (benzylthiomethyl) | C20H20N2O7S2 | 464,52 | 463 (M − H, 31%) |
| (indol-3-ylcarbonyl) | C21H17N3O8S | 471,45 | 470 (M − H, 32%) |
| (indol-3-ylacetyl) | C22H19N3O8S | 485,48 | No hit |
| (2-nitrophenylacetyl) | C20H17N3O10S | 491,44 | No hit |
| (α-acetamidostyryl) | C22H21N3O8S | 487,49 | 486 (M − H, 17%) |
| (1-acetylpyrrolidin-2-yl) | C18H21N3O8S | 439,45 | 438 (M − H, 30%) |

| R | Formula | Mw | LC/MS |
|---|---|---|---|
| 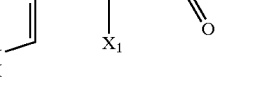 | C25H21N5O9S | 567,54 | 566 (M − H, 32%) |
| 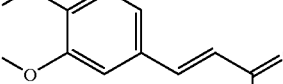 | C23H22N2O10S | 518,50 | 519 (M + H, 15%) |
| 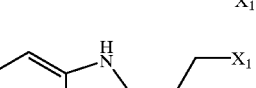 | C21H20N4O7S | 472,48 | 471 (M − H, 41%) |
| 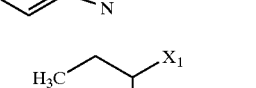 | C23H21N3O9S | 515,50 | 514 (M − H, 45%) |
| 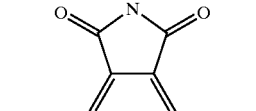 | C16H19N3O8S | 413,41 | 412 (M − H, 26%) |
| 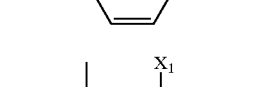 | C18H23N3O8S2 | 473,53 | 472 (M − H, 31%) |
| 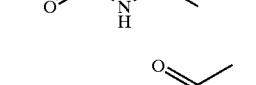 | C25H25N3O9S | 543,56 | 542 (M − H, 20%) |
| 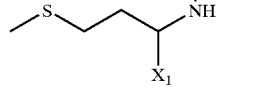 | C18H23N3O8S | 441,46 | 440 (M − H, 28%) |
| 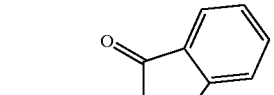 | C28H23N3O9S | 577,57 | 576 (M − H, 17%) |

-continued
| R | Formula | Mw | LC/MS |
|---|---|---|---|
| 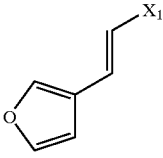 | C18H16N2O8S | 420,40 | 419 (M − H, 34%) |
| 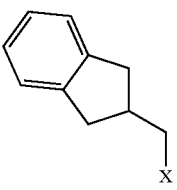 | C22H22N2O7S | 458,49 | 457 (M − H, 22%) |
| 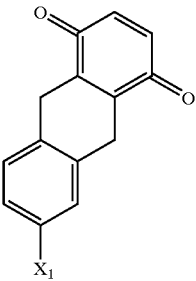 | C26H18N2O9S | 534,51 | No hit |
| 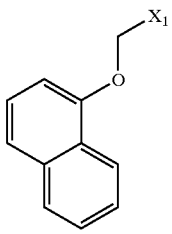 | C23H20N2O8S | 484,49 | No hit |
| 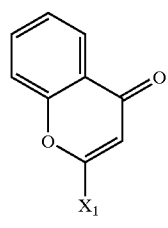 | C21H16N2O9S | 472,43 | 471 (M − H, 30%) |
| 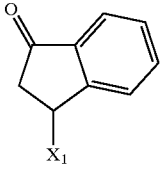 | C21H18N2O8S | 458,45 | 457 (M − H, 27%) |
| 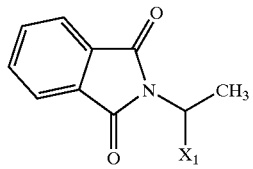 | C22H19N3O9S | 501,48 | 500 (M − H, 30%) |

What is claimed is:
1. A compound of Formula 1

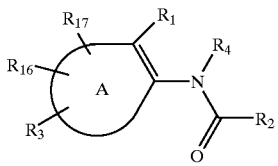

Formula 1 wherein
- A is together with the double bond in Formula 1 4,7-dihydro-5H-thieno[2,3-c]pyranyl, 4,7-dihydro-5H-thieno[2,3-c]thiopyranyl, 4,7-dihydro-5H-thieno[2,3-c]thiopyranyl-6-oxide, or 4,7-dihydro-5H-thieno[2,3-c]thiopyranyl-6,6-dioxide;
- $R_1$ is hydrogen, $COR_5$, $OR_6$, $CF_3$, nitro, $SO_3H$, $PO(OH)_2$, $C(=NH)NH_2$;
- $R_2$ is $COR_5$, $OR_6$, $CF_3$, nitro, cyano, $SO_3H$, $PO(OH)_2$, or $C(=NH)NH_2$;
- $R_3$, $R_{16}$ and $R_{17}$ are independently hydrogen, $C_1$–$C_6$alkyl, aryl, aryl$C_1$–$C_6$alkyl, oxo, $C_1$–$C_6$alkyloxycarbonyl, aryloxycarbonyl, aryl$C_1$–$C_6$alkyloxycarbonyl, aryl$C_1$–$C_6$alkyloxy, aryl$C_1$–$C_6$alkyloxy$C_1$–$C_6$alkyl, aryl$C_1$–$C_6$alkylthio, aryl$C_1$–$C_6$alkylthio$C_1$–$C_6$alkyl, aryl$C_1$–$C_6$alkylamino$C_1$–$C_6$alkyl, di(aryl$C_1$–$C_6$alkyl) amino$C_1$–$C_6$alkyl, aryl$C_1$–$C_6$alkylcarbonyl, aryl$C_1$–$C_6$alkylcarbonyl$C_1$–$C_6$alkyl, arylcarboxy$C_1$–$C_6$alkyl, aryl$C_1$–$C_6$alkylcarboxy, aryl$C_1$–$C_6$alkylcarboxy$C_1$–$C_6$alkyl, aryl$C_1$–$C_6$alkylcarbonylamino, aryl$C_1$–$C_6$alkylcarbonylamino$C_1$–$C_6$alkyl, wherein the alkyl and aryl groups are optionally substituted;
- $R_4$ is hydrogen, hydroxy, $C_1$–$C_6$alkyl, aryl, aryl$C_1$–$C_6$alkyl, $NR_7R_8$, $C_1$–$C_6$alkyloxy; wherein the alkyl and aryl groups are optionally substituted;
- $R_5$ is hydroxy $C_1$–$C_6$alkyloxy, $C_1$–$C_6$alkyloxy$C_1$–$C_6$alkyloxy, or aryl$C_1$–$C_6$alkyloxy; wherein the alkyl and aryl groups are optionally substituted;
- $R_6$ is hydrogen;
- $R_7$ and $R_8$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy wherein the alkyl and aryl groups are optionally substituted; or
- $R_7$ and $R_8$ are together with the nitrogen to which they are attached forming a saturated, partially saturated or aromatic cyclic, bicyclic or tricyclic ring system containing from 3 to 14 carbon atoms and from 0 to 3 additional heteroatoms selected from nitrogen, oxygen or sulfur, the ring system can optionally be substituted with at least one $C_1$–$C_6$alkyl, aryl, aryl$C_1$–$C_6$alkyl, hydroxy, oxo, $C_1$–$C_6$alkyloxy, aryl$C_1$–$C_6$alkyloxy, $C_1$–$C_6$alkyloxy$C_1$–$C_6$alkyl, $NR_9R_{10}$ or $C_1$–$C_6$alkylamino$C_1$–$C_6$alkyl, wherein $R_9$ and $R_{10}$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy; wherein the alkyl and aryl groups are optionally substituted; or
- $R_7$ and $R_8$ are independently a saturated or partial saturated cyclic 5, 6 or 7 membered amine, imide or lactam;

or a salt thereof with a pharmaceutically acceptable acid or base, or any optical isomer or mixture of optical isomers, racemic mixtures, or any tautomeric forms.

2. A compound according to claim 1 wherein A is 4,7-dihydro-5H-thieno[2,3-c]pyranyl.

3. A compound according to claim 1 wherein A is 4,7-dihydro-5H-thieno[2,3-c]thiopyranyl.

4. A compound according to claim 1 wherein A is 4,7-dihydro-5H-thieno[2,3-c]thiopyranyl-6,6-dioxide.

5. A pharmaceutical composition suitable for treating type I diabetes, type II diabetes, impaired glucose tolerance, insulin resistance or obesity comprising an effective amount of a compound of claim 1 together with one or more pharmaceutically acceptable carriers or diluents.

6. A method of treating type I diabetes, type II diabetes, impaired glucose tolerance, insulin resistance or obesity comprising administering to a subject in need thereof an effective amount of a compound of claim 1 to said subject.

7. A compound selected from the following:
- 2-(Oxalyl-amino)-4,7-dihydro-5H-thieno[2,3-c]pyran-3-carboxylic acid;
- 2-(Oxalyl-amino)-5-(((4-oxo-chromene-4H-2-carbonyl)amino)methyl)-4,7-dihydro-5H-thieno[2,3-c]pyran-3-carboxylic acid;
- 2-(Oxalyl-amino)-4,7-dihydro-5H-thieno[2,3-c]thiopyran-3-carboxylic acid;
- 2-(Oxalyl-amino)-6-oxo-4,7-dihydro-5H-thieno[2,3-c]thiopyran-3-carboxylic acid;
- 2-(Oxalyl-amino)-6,6-dioxo-4,7-dihydro-5H-thieno[2,3-c]thiopyran-3-carboxylic acid;
- 5-(Benzoylamino-methyl)-2-(oxalyl-amino)-4,7-dihydro-5H-thieno[2,3-c]pyran-3-carboxylic acid;
- 5-Benzoyloxymethyl-2-(oxalyl-amino)-4,7-dihydro-5H-thieno[2,3-c]pyran-3-carboxylic acid;
- N-(4-Carboxymethyl-4,7-dihydro-5H-thieno[2,3-c]pyran-2-yl)-oxalamic acid;
- N-(4-Carboxymethylene-4,7-dihydro-5H-thieno[2,3-c]pyran-2-yl)-oxalamic acid;
- N-(4-(2H-tetrazol-5-ylmethyl)-4,7-dihydro-5H-thieno[2,3-c]pyran-2-yl)-oxalamic acid;
- 2-(Oxalyl-amino)-5-((3-phenoxy-benzoylamino)-methyl)-4,7-dihydro-5H-thieno[2,3-c])pyran-3-carboxylic acid;
- 5-((3,5-Dimethoxy-benzoylamino)-methyl)-2-(oxalyl-amino)-4,7-dihydro-5H-thieno[2,3-c]pyran-3-carboxylic acid;
- 5-((3,5-Bis-trifluoromethyl-benzoylamino)-methyl)-2-(oxalyl-amino)-4,7-dihydro-5H-thieno[2,3-c]pyran-3-carboxylic acid;
- 5-((Cyclohexanecarbonyl-amino)-methyl)-2-(oxalyl-amino)-4,7-dihydro-5H-thieno[2,3-c]pyran-3-carboxylic acid;
- 5-((3-Dimethylamino-benzoylamino)-methyl)-2-(oxalyl-amino)-4,7-dihydro-5H-thieno[2,3-c]pyran-3-carboxylic acid;
- 5-((4-Acetylamino-benzoylamino)-methyl)-2-(oxalyl-amino)-4,7-dihydro-5H-thieno[2,3-c]pyran-3-carboxylic acid;
- 5-((2-Cyclopent-2-enyl-acetylamino)-methyl)-2-(Oxalyl-amino)-4,7-dihydro-5H-thieno[2,3-c]pyran-3-carboxylic acid;
- 5-((2-Acetylamino-benzoylamino)-methyl)-2-(oxalyl-amino)-4,7-dihydro-5H-thieno[2,3-c]pyran-3-carboxylic acid;

5-((3-Methoxy-benzoylamino)-methyl)-2-(oxalyl-amino)-4,7-dihydro-5H-thieno[2,3-c]pyran-3-carboxylic acid;
5-((4-Dimethylamino-benzoylamino)-methyl)-2-(oxalyl-amino)-4,7-dihydro-5H-thieno[2,3-c]pyran-3-carboxylic acid;
2-(Oxalyl-amino)-5-((4-phenoxy-benzoylamino)-methyl)-4,7-dihydro-5H-thieno[2,3-c]pyran-3-carboxylic acid;
5-((4-Acetoxy-benzoylamino)-methyl)-2-(oxalyl-amino)-4,7-dihydro-5H-thieno[2,3-c]pyran-3-carboxylic acid;
5-(But-2-enoylamino-methyl)-2-(oxalyl-amino)-4,7-dihydro-5H-thieno[2,3-c]pyran-3-carboxylic acid;
2-(Oxalyl-amino)-5-((4-oxo-4-phenyl-butyrylamino)-methyl)-4,7-dihydro-5H-thieno[2,3-c]pyran-3-carboxylic acid;
2-(Oxalyl-amino)-5-((5-oxo-hexanoylamino)-methyl)-4,7-dihydro-5H-thieno[2,3-c]pyran-3-carboxylic acid;
2-(Oxalyl-amino)-5-((4-oxo-4-phenyl-but-2-enoylamino)-methyl)-4,7-dihydro-5H-thieno[2,3-c]pyran-3-carboxylic acid;
5-((2-(4-Benzyloxy-phenoxy)-acetylainino)-methyl)-2-(oxalyl-amino)-4,7-dihydro-5H-thieno [2,3-c]pyran-3-carboxylic acid;
2-(Oxalyl-amino)-5-((3-phenyl-propionylamino)-methyl)-4,7-dihydro-5H-thieno[2,3-c]pyran-3-carboxylic acid;
5-(((Naphthalene-2-carbonyl)-amino)-methyl)-2-(oxalyl-amino)-4,7-dihydro-5H-thieno[2,3-c]pyran-3-carboxylic acid;
2-(Oxalyl-amino)-5-((2-phenoxy-acetylamino)-methyl)-4,7-dihydro-5H-thieno[2,3-c]pyran-3-carboxylic acid;
2-(Oxalyl-amino)-5-(phenylacetylamino-methyl)-4,7-dihydro-5H-thieno[2,3-c]pyran-3-carboxylic acid;
5-((2-(3,4-Dimethoxy-phenyl)-acetylamino)-methyl)-2-(oxalyl-amino)-4,7-dihydro-5H-thieno[2,3-c]pyran-3-carboxylic acid;
5-((2-(4-Ethoxy-phenyl)-acetylamino)-methyl)-2-(oxalyl-amino)-4,7-dihydro-5H-thieno[2,3-c]pyran-3-carboxylic acid;
2-(Oxalyl-amino)-5-((3-phenyl-acryloylamino)-methyl)-4,7-dihydro-5H-thieno[2,3-c]pyran-3-carboxylic acid;
5-((3-(3,5-Dimethoxy-phenyl)-acryloylamino)-methyl)-2-(oxalyl-amino)-4,7-dihydro-5H-thieno[2,3-c]pyran-3-carboxylic acid;
5-((2-(3,5-Bis-trifluoromethyl-phenyl)-acetylainino)-methyl)-2-(oxalyl-amino)-4,7-dihydro-5H-thieno[2,3-c]pyran-3-carboxylic acid;
5-((3-Benzenesulfonyl-propionylamino)-methyl)-2-(oxalyl-amino)-4,7-dihydro-5H-thieno[2,3-c]pyran-3-carboxylic acid;
5-((3-(3,5-Difluoro-phenyl)-acryloylamino)-methyl)-2-(oxalyl-amino)-4,7-dihydro-5H-thieno[2,3-c]pyran-3-carboxylic acid;
2-(Oxalyl-amino)-5-((4-oxo-pent-2-enoylamino)-methyl)-4,7-dihydro-5H-thieno[2,3-c]pyran-3-carboxylic acid;
2-(Oxalyl-amino)-5-((6-oxo-heptanoylamino)-methyl)-4,7-dihydro-5H-thieno[2,3-c]pyran-3-carboxylic acid;
5-((2-(4-Dimethylamino-phenyl)-acetylamino)-methyl)-2-(oxalyl-amino)-4,7-dihydro-5H-thieno[2,3-c]pyran-3-carboxylic acid;
5-(((Benzo(1,3)dioxole-5-carbonyl)-amino)-methyl)-2-(oxalyl-amino)-4,7-dihydro-5H-thieno[2,3-c]pyran-3-carboxylic acid;
5-((2-Acetylamino-3-phenyl-propionylamino)-methyl)-2-(oxalyl-amino)-4,7-dihydro-5H-thieno[2,3-c]pyran-3-carboxylic acid;
5-((2-Acetoxy-benzylamino)-methyl)-2-(oxalyl-amino)-4,7-dihydro-5H-thieno[2,3-c]pyran-3-carboxylic acid;
2-(Oxalyl-amino)-5-((2-oxo-3-phenyl-propionylamino)-methyl)-4,7-dihydro-5H-thieno[2,3-c]pyran-3-carboxylic acid;
5-((2-Benzoylamino-acetylamino)-methyl)-2-(oxalyl-amino)-4,7-dihydro-5H-thieno[2,3-c]pyran-3-carboxylic acid;
2-(Oxalyl-amino)-5-((4-oxo-pentanoylamino)-methyl)-4,7-dihydro-5H-thieno[2,3-c]pyran-3-carboxylic acid;
5-((2-Acetylamino-acetylamino)-methyl)-2-(oxalyl-amino)-4,7-dihydro-5H-thieno[2,3-c]pyran-3-carboxylic acid;
2-(Oxalyl-amino)-5-((2-phenylsulfanyl-acetylamino)-methyl)-4,7-dihydro-5H-thieno[2,3-c]pyran-3-carboxylic acid;
5-((2-Benzylsulfanyl-acetylamino)-methyl)-2-(oxalyl-amino)-4,7-dihydro-5H-thieno[2,3-c]pyran-3-carboxylic acid;
5-((3-(2-Nitro-phenyl)-2-oxo-propionylamino)-methyl)-2-(oxalyl-amino)-4,7-dihydro-5H-thieno[2,3-c]pyran-3-carboxylic acid;
5-((2-Acetylamino-3-phenyl-acryloylamino)-methyl)-2-(oxalyl-amino)-4,7-dihydro-5H-thieno[2,3-c]pyran-3-carboxylic acid;
5-((4-(3,4-Dimethoxy-phenyl)-2-oxo-but-3-enoylamino)-methyl)-2-(oxalyl-amino)-4,7-dihydro-5H-thieno[2,3-c]pyran-3-carboxylic acid;
5-((3-1H-Benzoimidazol-2-yl-propionylamino)-methyl)-2-(oxalyl-amino)-4,7-dihydro-5H-thieno[2,3-c]pyran-3-carboxylic acid;
5-((2-Acetylamino-propionylamino)-methyl)-2-(oxalyl-amino)-4,7-dihydro-5H-thieno[2,3-c]pyran-3-carboxylic acid;
5-((2-Acetylamino-4-methylsulfanyl-butyrylamino)-methyl)-2-(oxalyl-amino)-4,7-dihydro-5H-thieno[2,3-c]pyran-3-carboxylic acid;
5-((2-Acetylamino-3-methyl-butyrylamino)-methyl)-2-(oxalyl-amino)-4,7-dihydro-5H-thieno[2,3-c]pyran-3-carboxylic acid;
5-((2-Indan-2-yl-acetylamino)-methyl)-2-(oxalyl-amino)-4,7-dihydro-5H-thieno[2,3-c]pyran-3-carboxylic acid;
5-(((9,10-Dioxo-9,10-dihydro-anthracene-2-carbonyl)-amino)-methyl)-2-(oxalyl-amino)-4,7-dihydro-5H-thieno[2,3-c]pyran-3-carboxylic acid;
5-((2-(Naphthalen-1-yloxy)-acetylamino)-methyl)-2-(oxalyl-amino)-4,7-dihydro-5H-thieno[2,3-c]pyran-3-carboxylic acid;
2-(Oxalyl-amino)-5-(((4-oxo-4H-chromene-2-carbonyl)-amino)-methyl)-4,7-dihydro-5H-thieno[2,3-c]pyran-3-carboxylic acid;
2-(Oxalyl-amino)-5-(((3-oxo-indane-1-carbonyl)-amino)-methyl)-4,7-dihydro-5H-thieno[2,3-c]pyran-3-carboxylic acid;
7-(Acetylamino-methyl)-2-(oxalyl-amino)-4,7-dihydro-5H-thieno[2,3-c]pyran-3-carboxylic acid;
2-(Oxalyl-amino)-5-(((3-oxo-indane-1-carbonyl)amino)methyl)-4,7-dihydro-5H-thieno[2,3-c]pyran-3-carboxylic acid;
5-[(4-Methoxy-benzenesulfonylamino)-methyl]-2-(oxalyl-amino)-4,7-dihydro-5H-thieno[2,3-c]pyran-3-carboxylic acid;
or a pharmaceutically acceptable salt thereof.

* * * * *